United States Patent
Katayama et al.

(10) Patent No.: US 6,329,478 B1
(45) Date of Patent: Dec. 11, 2001

(54) TRANSITION METAL COMPLEX, PROCESS FOR PRODUCING THE SAME, OLEFIN POLYMERIZATION CATALYST CONTAINING THE TRANSITION METAL COMPLEX AND PROCESS FOR PRODUCING OLEFIN POLYMERS

(75) Inventors: Hiroaki Katayama; Masaaki Nabika; Akio Imai, all of Ichihara; Akira Miyashita, Ageo; Tsuyoshi Watanabe, Ichihara; Hirofumi Johohji, Ichihara; Yoshiaki Oda, Toyonaka; Hidenori Hanaoka, Osaka, all of (JP)

(73) Assignee: Sumitmo Chemical Company, Limited

( * ) Notice: Subject to any disclaimer, the term of this patent is extended or adjusted under 35 U.S.C. 154(b) by 0 days.

(21) Appl. No.: 08/983,536
(22) PCT Filed: Jul. 15, 1996
(86) PCT No.: PCT/JP96/01975
  § 371 Date: Apr. 30, 1999
  § 102(e) Date: Apr. 30, 1999
(87) PCT Pub. No.: WO97/03992
  PCT Pub. Date: Feb. 6, 1997

(30) Foreign Application Priority Data

Jul. 14, 1995 (JP) ................................. 7-178726

(51) Int. Cl.$^7$ ............... C08F 4/16; C08F 112/34; C07F 17/00; C07F 7/00
(52) U.S. Cl. ............. 526/127; 526/160; 526/161; 526/943; 526/348.6; 526/336; 502/152; 502/155; 556/11; 556/12; 556/52; 556/53
(58) Field of Search ............ 526/160, 161, 526/943, 127, 348.6, 336; 502/152; 556/53, 11, 52, 12

(56) References Cited

U.S. PATENT DOCUMENTS

| | | | |
|---|---|---|---|
| 5,055,438 | 10/1991 | Canich | 526/160 |
| 5,064,802 | 11/1991 | Stevens | 526/160 |
| 5,132,380 | 7/1992 | Stevens | 526/160 |
| 5,168,111 | 12/1992 | Canich | 526/160 |
| 5,321,106 | 6/1994 | LaPointe | 526/160 |
| 6,090,961 | * 7/2000 | Hanaoka et al. | 556/11 |

FOREIGN PATENT DOCUMENTS

| | | |
|---|---|---|
| 0 416 815 A2 | 3/1991 | (EP) . |
| 61-68436 | 4/1986 | (JP) . |
| 62-106050 | 5/1987 | (JP) . |
| 1-236205 | 9/1989 | (JP) . |
| 6-80683 | 3/1994 | (JP) . |
| WO 92/00333 | 1/1992 | (WO) . |
| WO 97/44389 | 11/1997 | (WO) . |

OTHER PUBLICATIONS

Chemical Abstracts 122: 10166k.

(List continued on next page.)

*Primary Examiner*—David W. Wu
*Assistant Examiner*—R. Harlan
(74) *Attorney, Agent, or Firm*—Fitch, Even, Tabin & Flannery

(57) ABSTRACT

The present invention relates to a transition metal complex, a process for producing the same, a polymerization catalsyt containing the transition metal complex and a process for producing polymers which uses the catalysts.

40 Claims, 1 Drawing Sheet

OTHER PUBLICATIONS

English translation of JP–A–62–106050.
English translation of JP–A–1–236205.
English translation of JP–A–61–68435.
Chemical Abstract No. 108696a, vol. 85, No. 15, Oct. 11, 1976.
Olivero, et al. "Nickel–Mediated Electrochemical Reductive Deprotection of Allyl Ethers", J. Chem. Soc., Chem. Commun., 1995, pp. 2497–2498.
Morgan, et al. "Mechanism of Arylation of Nucleophiles byt Aryllead Triacetates, Part 1. Exclusion of a Pathway Involving Aryl Free Radicals", J. Chem. Soc. Perkin Trans. 1, 1993, pp. 1673–1676.
Chemical Abstract No. 152354d, vol. 81, No. 23, Dec. 9, 1974, Qian, et al.
Chemical Abstract No. 24703, vol. 102, No. 3, Jan. 21, 1985, Qian, et al.
Chemical Abstract No. 255047, vol. 118, No. 25, Jun. 21, 1993, Qian, et al.
Chemical Abstract, vol. 122, No. 1, Jan. 2, 1995, Qian et al.
Chemical Abstract, vol. 121, No. 11, Sep. 12, 1994, Qian et al.
Chemical Abstract, vol. 102, No. 3, Jan. 1985, p. 703, Lapkin, I.I. et al.
Chemical Abstract, vol. 112, No. 5, Jan. 29, 1990, p. 529, Liu, Yulong et al.
Qian et al., Synthesis structure of some new titanoxacycle complexes, Chemical Abstracts, vol. 121, No. 11, 121: 134324, 1994.*

* cited by examiner

TRANSITION METAL COMPLEX, PROCESS FOR PRODUCING THE SAME, OLEFIN POLYMERIZATION CATALYST CONTAINING THE TRANSITION METAL COMPLEX AND PROCESS FOR PRODUCING OLEFIN POLYMERS

TECHNICAL FIELD

The present invention relates to a transition metal complex, a process for producing the same, a polymerization catalyst containing the transition metal complex and a process for producing polymers which uses the catalyst.

BACKGROUND ART

A number of reports have already been made on the process for producing olefin polymers using a metallocene complex. For example, JP-A-58-19309 discloses a process for producing olefin polymers which uses a metallocene complex and an aluminoxanone. The process has a problem in that when olefin is polymerized with the disclosed catalyst which uses bis(cyclopentadienyl)zirconium dichloride and methylaluminoxane, the molecular weight of the olefin polymer obtained is low. To improve this point, WO87/02370 discloses the use of a reaction product of an organic compound having at least two hydroxyl groups with a transition metal compound. However, the system disclosed in WO87/02370 which uses 2,2'-thiobis(6-tert-butyl-4-methylphenoxy)titanium dichloride and methylaluminoxane, and also a system disclosed in JP-A-5-230133 which uses 2,2'-thiobis(6-tert-butyl-4-methylphenoxy)titanium dichloride, triisobutylaluminum and triphenylmethyl tetrakis(pentafluorophenyl)borate involve a problem in that the catalytic activity is unsatisfactorily low from the industrial point of view although the molecular weight of the polymer produced is improved.

Moreover, known metallocene complexes, e.g., ethylenebis(indenyl)zirconium dichloride, isopropylidene (cyclopentadienyl) (fluorenyl)zirconium dichloride and dimethylsilyl(tert-butylamide)-(tetramethylcyclopentadienyl)titanium dichloride, have a problem in that they are insoluble in saturated hydrocarbon solvents although they are soluble in aromatic hydrocarbon solvents and resultantly polymerization catalysts containing such complexes cannot be used for producing polymers using saturated hydrocarbon solvents.

In recognition of the situation, the objects of the present invention are to provide a complex, important from the industrial viewpoint, which has a high activity at reaction temperatures efficient in the industrial process for olefin polymerization and is soluble in saturated hydrocarbon solvents, and to provide a highly active olefin polymerization catalyst containing the complex, and a process for producing olefin polymers which uses the catalyst.

DISCLOSURE OF THE INVENTION

The present inventors have made extensive study on transition metal complexes and olefin polymerization catalysts in order to attain the above-mentioned objects. As the result, the inventors have found a transition metal complex soluble in saturated hydrocarbon solvents which has a ligand comprising an aromatic ring having a hetero atom in the substituent and a cyclopentadienyl ring linked with each other through a covalent bonding group, and have accomplished the present invention on the basis of above finding.

Thus, according to the present invention, there are provided a transition metal complex represented by the formula (1) (hereinafter referred to as compound (1)) and a polymerization catalyst containing the complex:

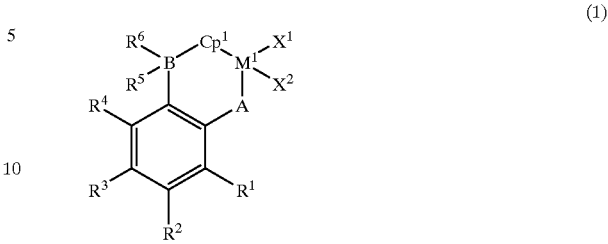

(1)

wherein $M^1$ is a transition metal atom of the group 4 of the periodic table of elements, A is an atom of the group 16 of the periodic table of elements and B is an atom of the group 14 of the periodic table of elements; $Cp^1$ is a group having a cyclopentadiene type anionic skeleton; and $X^1$, $X^2$, $R^1$, $R^2$, $R^3$, $R^4$, $R^5$ and $R^6$ are each independently a hydrogen atom, halogen atom, alkyl group with the number of carbon atoms of 1–20 optionally substituted with at least one halogen atom, aralkyl group with the number of carbon atoms of 7–20 optionally substituted with at least one halogen atom, aryl group with the number of carbon atoms of 6–20 optionally substituted with at least one halogen atom, substituted silyl group with the number of carbon atoms of 1–20 optionally substituted with at least one halogen atom, alkoxy group with the number of carbon atoms of 1–20 optionally substituted with at least one halogen atom, aralkyloxy group with the number of carbon atoms of 7–20 optionally substituted with at least one halogen atom, aryloxy group with the number of carbon atoms of 6–20 optionally substituted with at least one halogen atom, or di-substituted amino group with the number of carbon atoms of 2–20; provided that $R^1$, $R^2$, $R^3$, $R^4$, $R^5$ and $R^6$ may optionally combine with each other to form a ring.

[Transition metal complex]

In the compound [1], the transition metal atom represented by $M^1$ refers to a transition metal atom of the group 4 of the periodic table of elements (Nomenclature of Inorganic Chemistry, IUPAC, revised ed., 1989) and may be, for example, a titanium atom, zirconium atom and hafnium atom.

The atom of the group 16 of the periodic table of elements represented by A may be, for example, an oxygen atom, sulfur atom and selenium atom, and is preferably an oxygen atom.

The atom of the group 14 of the periodic table of elements represented by B may be, for example, a carbon atom, silicon atom and germanium atom.

The group having a cyclopentadiene type anionic skeleton represented as the substituent $Cp^1$ may be, for example, the $\eta^5$-cyclopentadienyl group, $\eta^5$-methylcyclopentadienyl group, $\eta^5$-dimethylcyclopentadienyl group, $\eta^5$-trimethylcyclopentadienyl group, $\eta^5$-tetramethylcyclopentadienyl group, $\eta^5$-ethylcyclopentadienyl group, $\eta^5$-n-propylcyclopentadienyl group, $\eta^5$-isopropylcyclopentadienyl group, $\eta^5$-n-butylcyclopentadienyl group, $\eta^5$-sec-butylcyclopentadienyl group, $\eta^5$-tert-butylcyclopentadienyl group, $\eta^5$-n-pentylcyclopentadienyl group, $\eta^5$-neopentylcyclopentadienyl group, $\eta^5$-n-hexylcyclopentadienyl group, $\eta^5$-n-octylcyclopentadienyl group, $\eta^5$-phenylcyclopentadienyl group, $\eta^5$-naphthylcyclopentadienyl group, $\eta^5$-trimethylsilylcyclopentadienyl group, $\eta^5$-triethylsilylcyclopentadienyl group, $\eta^5$-tert-butyldimethylsilylcyclopentadienyl group, $\eta^5$-indenyl group, $\eta^5$-methylindenyl group, $\eta^5$-dimethylindenyl group, $\eta^5$-ethylindenyl group, $\eta^5$-n-propylindenyl group, $\eta^5$-isopropylindenyl group, $\eta^5$-n-butylindenyl group, $\eta^5$-sec-butylindenyl group, $\eta^5$-tert-butylindenyl group, $\eta^5$-n-pentylindenyl group, $\eta^5$-neopentylindenyl group, $\eta^5$-n-hexylindenyl group, $\eta^5$-n-octylindenyl group, $\eta^5$-n-decylindenyl group, $\eta^5$-phenylindenyl group, $\eta^5$-methylphenylindenyl group, $\eta$5-naphthylindenyl group, $\eta^5$-trimethylsilylindenyl group, $\eta^5$-triethylsilylindenyl group, $\eta^5$-tert-butyldimethylsilylindenyl group, $\eta^5$-tetrahydroindenyl group, $\eta^5$-fluorenyl group, $\eta^5$-methylfluorenyl group, $\eta^5$-dimethylfluorenyl group, $\eta^5$-ethylfluorenyl group, $\eta^5$-diethylfluorenyl group, $\eta^5$-n-propylfluorenyl group, $\eta^5$-di-n-propylfluorenyl group, $\eta^5$-isopropylfluorenyl group, $\eta^5$-diisopropylfluorenyl group, $\eta^5$-n-butylfluorenyl group, $\eta^5$-sec-butylfluorenyl group, $\eta^5$-tert-butylfluorenyl group, $\eta^5$-di-n-butylfluorenyl group, $\eta^5$-di-sec-butylfluorenyl group, $\eta^5$-di-tert-butylfluorenyl group, $\eta^5$-n-pentyfluorenyl group, $\eta^5$-neopentylfluorenyl group, $\eta^5$-n-hexylfluorenyl group, $\eta^5$-n-octylfluorenyl group, $\eta^5$-n-decylfluorenyl group, $\eta^5$-n-dodecylfluorenyl group, $\eta^5$-phenylfluorenyl group, $\eta^5$-di-phenylfluorenyl group, $\eta^5$-methylphenylfluorenyl group, $\eta^5$-naphthylfluorenyl group, $\eta^5$-trimethylsilylfluorenyl group, $\eta^5$-bis-trimethylsilylfluorenyl group, $\eta^5$-triethylsilylfluorenyl group and $\eta^5$-tert-butyldimethylsilylfluorenyl group, preferred among them being, for example, the $\eta^5$-cyclopentadienyl group, $\eta^5$-methylcyclopentadienyl group, $\eta^5$-tert-butylcyclopentadienyl group, $\eta^5$-tetramethylcyclopentadienyl group, $\eta^5$-indenyl group and $\eta^5$-fluorenyl group.

The halogen atom in the substituents $X^1$, $X^2$, $R^1$, $R^2$, $R^3$, $R^4$, $R^5$ and $R^6$ may be, for example, a fluorine atom, chlorine atom, bromine atom and iodine atom.

The alkyl group with the number of carbon atoms of 1–20 in the substituents $X^1$, $X^2$, $R^1$, $R^2$, $R^3$, $R^4$, $R^5$ and $R^6$ may be, for example, the methyl group, ethyl group, n-propyl group, isopropyl group, n-butyl group, sec-butyl group, tert-butyl group, n-pentyl group, neopentyl group, amyl group, n-hexyl group, n-octyl group, n-decyl group, n-dodecyl group, n-pentadecyl group and n-eicosyl group, preferred among them being, the methyl group, ethyl group, isopropyl group, tert-butyl group and amyl group.

All of these alkyl groups may optionally be substituted with at least one halogen atom, e.g., fluorine atom, chlorine atom, bromine atom and iodine atom. The alkyl group with the number of carbon atoms of 1–20 substituted with at least one halogen atom may be, for example, the fluoromethyl group, difluoromethyl group, trifluoromethyl group, chloromethyl group, dichloromethyl group, trichloromethyl group, bromomethyl group, dibromomethyl group, tribromomethyl group, iodomethyl group, diiodomethyl group, triiodomethyl group, fluoroethyl group, difluoroethyl group, trifluoroethyl group, tetrafluoroethyl group, pentafluoroethyl group, chloroethyl group, dichloroethyl group, trichloroethyl group, tetrachloroethyl group, pentachloroethyl group, bromomethyl group, dibromoethyl group, tribromoethyl group, tetrabromoethyl group, pentabromoethyl group, perfluoropropyl group, perfluorobutyl group, perfluoropentyl group, perfluorohexyl group, perfluorooctyl group, perfluorododecyl group, perfluoropentadecyl group, perfluoroeicosyl group, perchloropropyl group, perchlorobutyl group, perchloropentyl group, perchlorohexyl group, perchlorooctyl group, perchlorododecyl group, perchloropentadecyl group, perchloroeicosyl group, perbromopropyl group, perbromobutyl group, perbromopentyl group, perbromohexyl group, perbromooctyl group, perbromododecyl group, perbromopentadecyl group and perbromoeicosyl group.

The aralkyl group with the number of carbon atoms of 7–20 in the substituents $X^1$, $X^2$, $R^1$, $R^2$, $R^3$, $R^4$, $R^5$ and $R^6$ may be, for example, the benzyl group, (2-methylphenyl)methyl group, (3-methylphenyl)methyl group, (4-methylphenyl)methyl group, (2,3-dimethylphenyl)methyl group, (2,4-dimethylphenyl)methyl group, (2,5-dimethylphenyl)methyl group, (2,6-dimethylphenyl)methyl group, (3,4-dimethylphenyl)methyl group, (4,6-dimethylphenyl)methyl group, (2,3,4-trimethylphenyl)methyl group, (2,3,5-trimethylphenyl)methyl group, (2,3,6-trimethylphenyl)methyl group, (3,4,5-trimethylphenyl)methyl group, (2,4,6-trimethylphenyl)methyl group, (2,3,4,5-tetramethylphenyl)methyl group, (2,3,4,6-tetramethylphenyl)methyl group, (2,3,5,6-tetramethylphenyl)methyl group, (pentamethylphenyl)methyl group, (ethylphenyl)methyl group, (n-propylphenyl)methyl group, (isopropylphenyl)methyl group, (n-butylphenyl)methyl group, (sec-butylphenyl)methyl group, (tert-butylphenyl)methyl group, (n-pentylphenyl)methyl group, (neopentylphenyl)methyl group, (n-hexylphenyl)methyl group, (n-octylphenyl)methyl group, (n-decylphenyl)methyl group, (n-decylphenyl)methyl group, (n-tetradecylphenyl)methyl group, naphthylmethyl group and anthracenylmethyl group, preferred of these being the benzyl group.

All of these aralkyl groups may optionally be substituted with at least one halogen atom, e.g., fluorine atom, chlorine atom, bromine atom and iodine atom.

The aryl group with the number of carbon atoms of 6–20 in the substituents $X^1$, $X^2$, $R^1$, $R^2$, $R^3$, $R^4$, $R^5$ and $R^6$ may be, for example, the phenyl group, 2-tolyl group, 3-tolyl group, 4-tolyl group, 2,3-xylyl group, 2,4-xylyl group, 2,5-xylyl group, 2,6-xylyl group, 3,4-xylyl group, 3,5-xylyl group, 2,3,4-trimethylphenyl group, 2,3,5-trimethylphenyl group, 2,3,6-trimethylphenyl group, 2,4,6-trimethylphenyl group, 3,4,5-trimethylphenyl group, 2,3,4,5-tetramethylphenyl group, 2,3,4,6-tetramethylphenyl group, 2,3,5,6-tetramethylphenyl group, pentamethylphenyl group, ethylphenyl group, n-propylphenyl group, isopropylphenyl group, n-butylphenyl group, sec-butylphenyl group, tert-butylphenyl group, n-pentylphenyl group, neopentylphenyl group, n-hexylphenyl group, n-octylphenyl group, n-decylphenyl group, n-dodecylphenyl group, n-tetradecylphenyl group, naphthyl group and anthracenyl group, preferred of these being the phenyl group.

All of these aryl groups may optionally be substituted with at least one halogen atom, e.g., fluorine atom, chlorine atom, bromine atom and iodine atom.

The substituted silyl group with the number of carbon atoms of 1–20 in the substituents $X^1$, $X^2$, $R^1$, $R^2$, $R^3$, $R^4$, $R^5$ and $R^6$ refers to a silyl group substituted with at least one hydrocarbon group. The hydrocarbon group may be, for example, an alkyl group with the number of carbon atoms of 1–10, such as the methyl group, ethyl group, n-propyl group, isopropyl group, n-butyl group, sec-butyl group, tert-butyl group, isobutyl group, n-pentyl group, n-hexyl group and cyclohexyl group, and an aryl group, such as phenyl group. Examples of the substituted silyl group with the number of carbon atoms of 1–20 include a monosubstituted silyl group with the number of carbon atoms of 1–20, such as the methylsilyl group, ethylsilyl group and phenylsilyl group, di-substituted silyl group with the number of carbon atoms of 2–20, such as the dimethylsilyl group, diethylsilyl group and diphenylsilyl group, and tri-substituted silyl groups with the number of carbon atoms of 3–20, such as trimethylsilyl group, triethylsilyl group, tri-n-propylsilyl group, triisopropylsilyl group, tri-n-butylsilyl group, tri-sec-butylsilyl group, tri-tert-butylsilyl group, tri-isobutylsilyl group, tert-butyl-dimethylsilyl group, tri-n-pentylsilyl group, tri-n-hexylsilyl group, tricyclohexylsilyl group and triphenylsilyl group, preferred of these being the trimethylsilyl group, tert-butyldimethylsilyl group and triphenylsilyl group.

The hydrocarbon groups of each of these substituted silyl groups may optionally be substituted with at least one halogen atom, e.g., fluorine atom, chlorine atom, bromine atom and iodine atom.

The alkoxy group with the number of carbon atoms of 1–20 in the substituents $X^1$, $X^2$, $R^1$, $R^2$, $R^3$, $R^4$, $R^5$ and $R^6$ may be, for example, the methoxy group, ethoxy group, n-propoxy group, isopropoxy group, n-butoxy group, sec-butoxy group, tert-butoxy group, n-pentoxy group, neopentoxy group, n-hexoxy group, n-octoxy group, n-dodecoxy group, n-pentadecoxy group and n-eicosoxy group, preferred of these being the methoxy group, ethoxy group and tert-butoxy group.

These alkoxy groups may each optionally be substituted with at least one halogen atom, e.g., fluorine atom, chlorine atom, bromine atom and iodine atom.

The aralkyloxy group with the number of carbon atoms of 7–20 in the substituents $X^1$, $X^2$, $R^1$, $R^2$, $R^3$, $R^4$, $R^5$ and $R^6$ may be, for example, the benzyloxy group, (2-methylphenyl)methoxy group, (3-methylphenyl)methoxy group, (4-methylphenyl)methoxy group, (2,3-dimethylphenyl)methoxy group, (2,4-dimethylphenyl)methoxy group, (2,,5-dimethylphenyl)methoxy group, (2,6-dimethylphenyl)methoxy group, (3,4-dimethylphenyl)methoxy group, (3,5-dimethylphenyl)methoxy group, (2,3,4-trimethylphenyl)methoxy group, (2,3,5-trimethylphenyl)methoxy group, (2,3,6-trimethylphenyl)methoxy group, (2,4,5-trimethylphenyl)methoxy group, (2,4,6-trimethylphenyl)methoxy group, (3,4,5-trimethylphenyl)methoxy group, (2,3,4,5-tetramethylphenyl)methoxy group, (2,3,4,6-tetramethylphenyl)methoxy group, (2,3,5,6-tetramethylphenyl)methoxy group, (pentamethylphenyl)methoxy group, (ethylphenyl)methoxy group, (n-propylphenyl)methoxy group, (isopropylphenyl)methoxy group, (n-butylphenyl)methoxy group, (sec-butylphenyl)methoxy group, (tert-butylphenyl)methoxy group, (n-hexylphenyl)methoxy group, (n-octylphenyl)methoxy group, (n-decylphenyl)methoxy group, (n-tetradecylphenyl)methoxy group, naphthylmethoxy group and anthracenylmethoxy group, preferred of these being the benzyloxy group.

These aralkyloxy groups may each optionally be substituted with at least one halogen atom, e.g., fluorine atom, chlorine atom, bromine atom and iodine atom.

The aryloxy group with the number of carbon atoms of 6–20 in the substituents $X^1$, $X^2$, $R^1$, $R^2$, $R^3$, $R^4$, $R^5$ and $R^6$ may be such an aryloxy group with the number of carbon atoms of 6–20 as the phenoxy group, 2-methylphenoxy group, 3-methylphenoxy group, 4-methylphenoxy group, 2,3-dimethylphenoxy group, 2,4-dimethylphenoxy group, 2,5-dimethylphenoxy group, 2,6-dimethylphenoxy group, 3,4-dimethylphenoxy group, 3,5-dimethylphenoxy group, 2,3,4-trimethylphenoxy group, 2,3,5-trimethylphenoxy group, 2,3,6-trimethylphenoxy group, 2,4,5-trimethylphenoxy group, 2,4,6-trimethylphenoxy group, 3,4,5-trimethylphenoxy group, 2,3,4,5-tetramethylphenoxy group, 2,3,4,6-tetramethylphenoxy group, pentamethylphenoxy group, ethylphenoxy group, n-propylphenoxy group, isopropylphenoxy group, n-butylphenoxy group, sec-butylphenoxy group, tert-butylphenoxy group, n-hexylphenoxy group, n-octylphenoxy group, n-decylphenoxy group, n-tetradecylphenoxy group, naphthoxy group and anthracenoxy group.

These aryloxy groups may each optionally be substituted with at least one halogen atom, e.g., fluorine atom, chlorine atom, bromine atom and iodine atom.

The di-substituted amino group with the number of carbon atoms of 2–20 in the substituents $X^1$, $X^2$, $R^1$, $R^2$, $R^3$, $R^4$, $R^5$ and $R^6$ refers to an amino group substituted with two hydrocarbon groups, the hydrocarbon group being, for example, an alkyl group with the number of carbon atoms of 1–10, such as the methyl group, ethyl group, n-propyl group, isopropyl group, n-butyl group, sec-butyl group, tert-butyl group, isobutyl group, n-pentyl group, n-hexyl group and cyclohexyl group, and an aryl group such as the phenyl group. Examples of such di-substituted amino group with the number of carbon atoms of 2–20 include the dimethylamino group, diethylamino group, di-n-propylamino group, diisopropylamino group, di-n-butylamino group, di-sec-butylamino group, di-tert-butylamino group, diisobutylamino group, tert-butylisopropylamino group, di-n-hexylamino group, di-n-octylamino group, di-n-decylamino group, diphenylamino group, bistrimethylsilylamino group and bis-tert-butyldimethylsilylamino group, preferred of these being the dimethylamino group and diethylamino group.

The substituents $R^1$, $R^2$, $R^3$, $R^4$, $R^5$ and $R^6$ may optionally combine with each other to form a ring.

$X^1$ and $X^2$ are each preferably a halogen atom, alkyl group and aralkyl group, more preferably a halogen atom.

$R^1$ is preferably an alkyl group with the number of carbon atoms of 1–20, aralkyl group, aryl group, halogenated alkyl group, halogenated aralkyl group, halogenated aryl group or substituted silyl group.

The compounds (1) include transition metal complexes wherein B in the formula (1) is a carbon atom, such as methylene(cyclopentadienyl)(3,5-dimethyl-2-phenoxy) titanium dichloride, methylene(cyclopentadienyl)(3-tert-butyl-2-phenoxy)titanium dichloride, methylene (cyclopentadienyl) (3-tert-butyl-5-methyl-2-phenoxy) titanium dichloride, methylene(cyclopentadienyl)(3-phenyl-2-phenoxy)titanium dichloride, methylene (cyclopentadienyl) (3-tert-butyldimethylsilyl-5-methyl-2-phenoxy)titanium dichloride, methylene(cyclopentadienyl) (3-trimethylsilyl-5-methyl-2-phenoxy)titanium dichloride, methylene(cyclopentadienyl)(3-tert-butyl-5-methoxy-2-phenoxy)titanium dichloride, methylene(cyclopentadienyl) (3-tert-butyl-5-chloro-2-phenoxy)titanium dichloride, methylene(methylcyclopentadienyl)(3,5-dimethyl-2-phenoxy)titanium dichloride, methylene (methylcyclopentadienyl)(3-tert-butyl-2-phenoxy)titanium dichloride, methylene(methylcyclopentadienyl)(3-tert-butyl-5-methyl-2-phenoxy)titanium dichloride, methylene (methylcyclopentadienyl)(3-phenyl-2-phenoxy)titanium dichloride, methylene(methylcyclopentadienyl)(3-tert-butyldimethylsilyl-5-methyl-2-phenoxy)titanium dichloride, methylene(methylcyclopentadienyl)(3-trimethylsilyl-5-methyl-2-phenoxy)titanium dichloride, methylene(methylcyclopentadienyl)(3-tert-butyl-5-methoxy-2-phenoxy)titanium dichloride, methylene (methylcyclopentadienyl)(3-tert-butyl-5-chloro-2-phenoxy) titanium dichloride, methylene(tert-butylcyclopentadienyl)(3,5-dimethyl-2-phenoxy)titanium dichloride, methylene(tert-butylcyclopentadienyl)(3-tert-butyl-2-phenoxy)titanium dichloride, methylene(tert-butylcyclopentadienyl)(3-tert-butyl-5-methyl-2-phenoxy)titanium dichloride, methylene(tert-butylcyclopentadienyl)(3-phenyl-2-phenoxy)titanium dichloride, methylene(tert-butylcyclopentadienyl)(3-tert-butyldimethylsilyl-5-methyl-2-phenoxy)titanium dichloride, methylene(tert-butylcyclopentadienyl)(3-trimethylsilyl-5-methyl-2-phenoxy)titanium dichloride, methylene(tert-butylcyclopentadienyl)(3-tert-butyl-5-methoxy-2-phenoxy)titanium dichloride, methylene(tert-butylcyclopentadienyl)(3-tert-butyl-5-chloro-2-phenoxy)titanium dichloride, methylene(tetramethylcyclopentadienyl)(3,5-dimethyl-2-phenoxy)titanium dichloride, methylene(tetramethylcyclopentadienyl)(3-tert-butyl-2-phenoxy)titanium dichloride, methylene(tetramethylcyclopentadienyl)(3-tert-butyl-5-methyl-2-phenoxy)titanium dichloride, methylene(tetramethylcyclopentadienyl)(3-phenyl-2-phenoxy)titanium dichloride, methylene(tetramethylcyclopentadienyl)(3-tert-butyldimethylsilyl-5-methyl-2-phenoxy)titanium dichloride, methylene(tetramethylcyclopentadienyl)(3-trimethylsilyl-5-methyl-2-phenoxy)titanium dichloride, methylene(tetramethylcyclopentadienyl)(3-tert-butyl-5-methoxy-2-phenoxy)titanium dichloride, methylene(tetramethylcyclopentadienyl)(3-tert-butyl-5-chloro-2-phenoxy)titanium dichloride, methylene(trimethylsilylcyclopentadienyl)(3,5-dimethyl-2-phenoxy)titanium dichloride, methylene(trimethylsilylcyclopentadienyl)(3-tert-butyl-2-phenoxy)titanium dichloride, methylene(trimethylsilylcyclopentadienyl)(3-tert-butyl-5-methyl-2-phenoxy)titanium dichloride, methylene(trimethylsilylcyclopentadienyl)(3-phenyl-2-phenoxy)titanium dichloride, methylene(trimethylsilylcyclopentadienyl)(3-tert-butyldimethylsilyl-5-methyl-2-phenoxy)titanium dichloride, methylene(trimethylsilylcyclopentadienyl)(3-trimethylsilyl-5-methyl-2-phenoxy)titanium dichloride, methylene(trimethylsilylcyclopentadienyl)(3-tert-butyl-5-methoxy-2-phenoxy)titanium dichloride, methylene(trimethylsilylcyclopentadienyl)(3-tert-butyl-5-chloro-2-phenoxy)titanium dichloride, methylene(fluorenyl)(3,5-dimethyl-2-phenoxy)titanium dichloride, methylene(fluorenyl)(3-tert-butyl-2-phenoxy)titanium dichloride, methylene(fluorenyl)(3-tert-butyl-5-methyl-2-phenoxy)titanium dichloride, methylene(fluorenyl)(3-phenyl-2-phenoxy)titanium dichloride, methylene(fluorenyl)(3-tert-butyldimethylsilyl-5-methyl-2-phenoxy)titanium dichloride, methylene(fluorenyl)(3-trimethylsilyl-5-methyl-2-phenoxy)titanium dichloride, methylene(fluorenyl)(3-tert-butyl-5-methoxy-2-phenoxy)titanium dichloride, methylene(fluorenyl)(3-tert-butyl-5-chloro-2-phenoxy)titanium dichloride, isopropylidene(cyclopentadienyl)(3,5-dimethyl-2-phenoxy)titanium dichloride, isopropylidene(cyclopentadienyl)(3-tert-butyl-2-phenoxy)titanium dichloride, isopropylidene(cyclopentadienyl)(3-tert-butyl-5-methyl-2-phenoxy)titanium dichloride, isopropylidene(cyclopentadienyl)(3-phenyl-2-phenoxy)titanium dichloride, isopropylidene(cyclopentadienyl)(3-tert-butyldimethylsilyl-5-methyl-2-phenoxy)titanium dichloride, isopropylidene(cyclopentadienyl)(3-trimethylsilyl-5-methyl-2-phenoxy)titanium dichloride, isopropylidene(cyclopentadienyl)(3-tert-butyl-5-methoxy-2-phenoxy)titanium dichloride, isopropylidene(cyclopentadienyl)(3-tert-butyl-5-chloro-2-phenoxy)titanium dichloride, isopropylidene(methylcyclopentadienyl)(3,5-dimethyl-2-phenoxy)titanium dichloride, isopropylidene(methylcyclopentadienyl)(3-tert-butyl-2-phenoxy)titanium dichloride, isopropylidene(methylcyclopentadienyl)(3-tert-butyl-5-methyl-2-phenoxy)titanium dichloride, isopropylidene(methylcyclopentadienyl)(3-phenyl-2-phenoxy)titanium dichloride, isopropylidene(methylcyclopentadienyl)(3-tert-butyldimethylsilyl-5-methyl-2-phenoxy)titanium dichloride, isopropylidene(methylcyclopentadienyl)(3-trimethylsilyl-5-methyl-2-phenoxy)titanium dichloride, isopropylidene(methylcyclopentadienyl)(3-tert-butyl-5-methoxy-2-phenoxy)titanium dichloride, isopropylidene(methylcyclopentadienyl)(3-tert-butyl-5-chloro-2-phenoxy)titanium dichloride, isopropylidene(tert-butylcyclopentadienyl)(3,5-dimethyl-2-phenoxy)titanium dichloride, isopropylidene(tert-butylcyclopentadienyl)(3-tert-butyl-2-phenoxy)titanium dichloride, isopropylidene(tert-butylcyclopentadienyl)(3-tert-butyl-5-methyl-2-phenoxy)titanium dichloride, isopropylidene(tert-butylcyclopentadienyl)(3-phenyl-2-phenoxy)titanium dichloride, isopropylidene(tert-butylcyclopentadienyl)(3-tert-butyldimethylsilyl-5-methyl-2-phenoxy)titanium dichloride, isopropylidene(tert-butylcyclopentadienyl)(3-trimethylsilyl-5-methyl-2-phenoxy)titanium dichloride, isopropylidene(tert-butylcyclopentadienyl)(3-tert-butyl-5-methoxy-2-phenoxy)titanium dichloride, isopropylidene(tert-butylcyclopentadienyl)(3-tert-butyl-5-chloro-2-phenoxy)titanium dichloride, isopropylidene(tetramethylcyclopentadienyl)(3,5-dimethyl-2-phenoxy)titanium dichloride, isopropylidene(tetramethylcyclopentadienyl)(3-tert-butyl-2-phenoxy)titanium dichloride, isopropylidene(tetramethylcyclopentadienyl)(3-tert-butyl-5-methyl-2-phenoxy)titanium dichloride, isopropylidene(tetramethylcyclopentadienyl)(3-phenyl-2-phenoxy)titanium dichloride, isopropylidene(tetramethylcyclopentadienyl)(3-tert-butyldimethylsilyl-5-methyl-2-phenoxy)titanium dichloride, isopropylidene(tetramethylcyclopentadienyl)(3-trimethylsilyl-5-methyl-2-phenoxy)titanium dichloride, isopropylidene(tetramethylcyclopentadienyl)(3-tert-butyl-5-methoxy-2-phenoxy)titanium dichloride, isopropylidene(tetramethylcyclopentadienyl)(3-tert-butyl-5-chloro-2-phenoxy)titanium dichloride, isopropylidene(trimethylsilylcyclopentadienyl)(3,5-dimethyl-2-phenoxy)titanium dichloride, isopropylidene(trimethylsilylcyclopentadienyl)(3-tert-butyl-2-phenoxy)titanium dichloride, isopropylidene(trimethylsilylcyclopentadienyl)(3-tert-butyl-5-methyl-2-phenoxy)titanium dichloride, isopropylidene(trimethylsilylcyclopentadienyl)(3-phenyl-2-phenoxy)titanium dichloride, isopropylidene(trimethylsilylcyclopentadienyl)(3-tert-butyldimethylsilyl-5-methyl-2-phenoxy)titanium dichloride, isopropylidene(trimethylsilylcyclopentadienyl)(3-trimethylsilyl-5-methyl-2-phenoxy)titanium dichloride, isopropylidene(trimethylsilylcyclopentadienyl)(3-tert-butyl-5-methoxy-2-phenoxy)titanium dichloride, isopropylidene(trimethylsilylcyclopentadienyl)(3-tert-butyl-5-chloro-2-phenoxy)titanium dichloride, isopropylidene(fluorenyl)(3,5-dimethyl-2-phenoxy)titanium dichloride, isopropylidene(fluorenyl)(3-tert-butyl- 2-phenoxy)titanium dichloride, isopropylidene(fluorenyl)(3-tert-butyl-5-methyl-2-phenoxy)titanium dichloride, isopropylidene(fluorenyl)(3-phenyl-2-phenoxy)titanium dichloride, isopropylidene(fluorenyl)(3-tert-butyldimethylsilyl-5-methyl-2-phenoxy)titanium dichloride, isopropylidene(fluorenyl)(3-trimethylsilyl-5-methyl-2-phenoxy)titanium dichloride, isopropylidene(fluorenyl)(3-tert-butyl-5-methoxy-2-phenoxy)titanium dichloride, isopropylidene(fluorenyl)(3-tert-butyl-5-chloro-2-phenoxy)titanium dichloride, diphenylmethylene(cyclopentadienyl)(3,5-dimethyl-2-phenoxy)titanium dichloride, diphenylmethylene(cyclopentadienyl)(3-tert-butyl-2-phenoxy)titanium dichloride, diphenylmethylene(cyclopentadienyl)(3-tert-butyl-5-methyl-2-phenoxy)titanium dichloride, diphenylmethylene(cyclopentadienyl)(3-phenyl-2-phenoxy)titanium dichloride, diphenylmethylene(cyclopentadienyl)(3-tert-butyldimethylsilyl-5-methyl-2-phenoxy)titanium dichloride, diphenylmethylene(cyclopentadienyl)(3-trimethylsilyl-5-methyl-2-phenoxy)titanium dichloride, diphenylmethylene(cyclopentadienyl)(3-tert-butyl-5-methoxy-2-phenoxy)titanium dichloride, diphenylmethylene(cyclopentadienyl)(3-tert-butyl-5-chloro-2-phenoxy)titanium dichloride, diphenylmethylene(methylcyclopentadienyl)(3,5-dimethyl-2-phenoxy)titanium dichloride, diphenylmethylene(methylcyclopentadienyl)(3-tert-butyl-2-phenoxy)titanium dichloride, diphenylmethylene(methylcyclopentadienyl)(3-tert-butyl-5-methyl-2-phenoxy)titanium dichloride, diphenylmethylene(methylcyclopentadienyl)(3-phenyl-2-phenoxy)titanium dichloride, diphenylmethylene(methylcyclopentadienyl)(3-tert-butyldimethylsilyl-5-methyl-2-phenoxy)titanium dichloride, diphenylmethylene(methylcyclopentadienyl)(3-trimethylsilyl-5-methyl-2-phenoxy)titanium dichloride, diphenylmethylene(methylcyclopentadienyl)(3-tert-butyl-5-methoxy-2-phenoxy)titanium dichloride, diphenylmethylene(methylcyclopentadienyl)(3-tert-butyl-5-chloro-2-phenoxy)titanium dichloride, diphenylmethylene(tert-butylcyclopentadienyl)(3,5-dimethyl-2-phenoxy)titanium dichloride, diphenylmethylene(tert-butylcyclopentadienyl)(3-tert-butyl-2-phenoxy)titanium dichloride, diphenylmethylene(tert-butylcyclopentadienyl)(3-tert-butyl-5-methyl-2-phenoxy)titanium dichloride, diphenylmethylene(tert-butylcyclopentadienyl)(3-phenyl-2-phenoxy)titanium dichloride, diphenylmethylene(tert-butylcyclopentadienyl)(3-tert-butyldimethylsilyl-5-methyl-2-phenoxy)titanium dichloride, diphenylmethylene(tert-butylcyclopentadienyl)(3-trimethylsilyl-5-methyl-2-phenoxy)titanium dichloride, diphenylmethylene(tert-butylcyclopentadienyl)(3-tert-butyl-5-methoxy-2-phenoxy)titanium dichloride, diphenylmethylene(tert-butylcyclopentadienyl)(3-tert-butyl-5-chloro-2-phenoxy)titanium dichloride, diphenylmethylene(tetramethylcyclopentadienyl)(3,5-dimethyl-2-phenoxy)titanium dichloride, diphenylmethylene(tetramethylcyclopentadienyl)(3-tert-butyl-2-phenoxy)titanium dichloride, diphenylmethylene(tetramethylcyclopentadienyl)(3-tert-butyl-5-methyl-2-phenoxy)titanium dichloride, diphenylmethylene(tetramethylcyclopentadienyl)(3-phenyl-2-phenoxy)titanium dichloride, diphenylmethylene(tetramethylcyclopentadienyl)(3-tert-butyldimethylsilyl-5-methyl-2-phenoxy)titanium dichloride, diphenylmethylene(tetramethylcyclopentadienyl)(3-trimethylsilyl-5-methyl-2-phenoxy)titanium dichloride, diphenylmethylene(tetramethylcyclopentadienyl)(3-tert-butyl-5-methoxy-2-phenoxy)titanium dichloride, diphenylmethylene(tetramethylcyclopentadienyl)(3-tert-butyl-5-chloro-2-phenoxy)titanium dichloride, diphenylmethylene(trimethylsilylcyclopentadienyl)(3,5-dimethyl-2-phenoxy)titanium dichloride, diphenylmethylene(trimethylsilylcyclopentadienyl)(3-tert-butyl-2-phenoxy)titanium dichloride, diphenylmethylene(trimethylsilylcyclopentadienyl)(3-tert-butyl-5-methyl-2-phenoxy)titanium dichloride, diphenylmethylene(trimethylsilylcyclopentadienyl)(3-phenyl-2-phenoxy)titanium dichloride, diphenylmethylene(trimethylsilylcyclopentadienyl)(3-tert-butyldimethylsilyl-5-methyl-2-phenoxy)titanium dichloride, diphenylmethylene(trimethylsilylcyclopentadienyl)(3-tert-trimethylsilyl-5-methyl-2-phenoxy)titanium dichloride, diphenylmethylene(trimethylsilylcyclopentadienyl)(3-tert-butyl-5-methoxy-2-phenoxy)titanium dichloride, diphenylmethylene(trimethylsilylcyclopentadienyl)(3-tert-butyl-5-chloro-2-phenoxy)titanium dichloride, diphenylmethylene(fluorenyl)(3,5-dimethyl-2-phenoxy)titanium dichloride, diphenylmethylene(fluorenyl)(3-tert-butyl-2-phenoxy)titanium dichloride, diphenylmethylene(fluorenyl)(3-tert-butyl-5-methyl-2-phenoxy)titanium dichloride, diphenylmethylene(fluorenyl)(3-phenyl-2-phenoxy)titanium dichloride, diphenylmethylene(fluorenyl)(3-tert-butyldimethylsilyl-5-methyl-2-phenoxy)titanium dichloride, diphenylmethylene(fluorenyl)(3-trimethylsilyl-5-methyl-2-phenoxy)titanium dichloride, diphenylmethylene(fluorenyl)(3-tert-butyl-5-methoxy-2-phenoxy)titanium dichloride and diphenylmethylene(fluorenyl)(3-tert-butyl-5-chloro-2-phenoxy)titanium dichloride; compounds resulting from changing the "titanium" in the above-mentioned compounds to zirconium or hafnium, compounds resulting from changing the "chloride" in the above-mentioned compounds to bromide, iodide, dimethylamide, diethylamide, n-butoxide or isopropoxide, compounds resulting from changing the "(cyclopentadienyl)" in the above-mentioned compounds to (dimethylcyclopentadienyl), (trimethylcyclopentadienyl), (n-butylcyclopentadienyl), (tert-butyldimethylsilylcyclopentadienyl) or (indenyl); compounds resulting from changing the "3,5-dimethyl-2-phenoxy" in the above-mentioned compounds to 2-phenoxy, 3-methyl-2-phenoxy, 3,5-di-tert-butyl-2-phenoxy, 3-phenyl-5-methyl-2-phenoxy, 3-tert-butyldimethylsilyl-2-phenoxy or 3-trimethylsilyl-2-phenoxy and compounds resulting from changing the "methylene" in the above-mentioned compounds to diethylmethylene; and transition metal complexes wherein B in the formula (1) is an atom of the group 14 of the periodic table of elements other than carbon atom, such as dimethylsilyl(cyclopentadienyl)(2-phenoxy)titanium dichloride, dimethylsilyl(cyclopentadienyl)(3-methyl-2-phenoxy)titanium dichloride, dimethylsilyl(cyclopentadienyl)(3,5-dimethyl-2-phenoxy)titanium dichloride, dimethylsilyl(cyclopentadienyl)(3-tert-butyl-2-phenoxy)titanium dichloride, dimethylsilyl(cyclopentadienyl)(3-tert-butyl-5-methyl-2-phenoxy)titanium dichloride, dimethylsilyl(cyclopentadienyl)(3,5-di-tert-butyl-2-phenoxy)titanium dichloride, dimethylsilyl(cyclopentadienyl)(5-methyl-3-phenyl-2-phenoxy)titanium dichloride, dimethylsilyl(cyclopentadienyl)(3-tert-butyldimethylsilyl-5-methyl-2-phenoxy)titanium dichloride, dimethylsilyl(cyclopentadienyl)(5-methyl-3-trimethylsilyl-2-phenoxy)titanium dichloride, dimethylsilyl(cyclopentadienyl)(3-tert-butyl-5-methoxy-2-phenoxy)titanium dichloride, dimethylsilyl(cyclopentadienyl)(3-tertbutyl-5-chloro-2-phenoxy)titanium dichloride, dimethylsilyl(cyclopentadienyl)(3,5-diamyl-2-phenoxy)titanium dichloride, dimethylsilyl(methylcyclopentadienyl)(2-phenoxy)titanium dichloride, dimethylsilyl(methylcyclopentadienyl)(3-methyl-2-phenoxy)titanium dichloride, dimethylsilyl(methylcyclopentadienyl)(3,5-dimethyl-2-phenoxy)titanium dichloride, dimethylsilyl(methylcyclopentadienyl)(3-tert-butyl-2-phenoxy)titanium dichloride, dimethylsilyl(methylcyclopentadienyl)(3-tert-butyl-5-methyl-2-phenoxy)titanium dichloride, dimethylsilyl(methylcyclopentadienyl)(3,5-di-tert-butyl-2-phenoxy)titanium dichloride, dimethylsilyl(methylcyclopentadienyl)(5-methyl-3-phenyl-2-phenoxy)titanium dichloride, dimethylsilyl(methylcyclopentadienyl)(3-tert-butyldimethylsilyl-5-methyl-2-phenoxy)titanium dichloride, dimethylsilyl(methylcyclopentadienyl)(5-methyl-3-trimethylsilyl-2-phenoxy)titanium dichloride, dimethylsilyl(methylcyclopentadienyl)(3-tert-butyl-5-methoxy-2-phenoxy)titanium dichloride, dimethylsilyl(methylcyclopentadienyl)(3-tert-butyl-5-chloro-2-phenoxy)titanium dichloride, dimethylsilyl(methylcyclopentadienyl)(3,5-diamyl-2-phenoxy)titanium dichloride, dimethylsilyl(n-butylcyclopentadienyl)(2-phenoxy)titanium dichloride, dimethylsilyl(n-butylcyclopentadienyl)(3-methyl-2-phenoxy)titanium dichloride, dimethylsilyl(n-butylcyclopentadienyl)(3,5-dimethyl-2-phenoxy)titanium dichloride, dimethylsilyl(n-butylcyclopentadienyl)(3-tert-butyl-2-phenoxy)titanium dichloride, dimethylsilyl(n-butylcyclopentadienyl)(3-tert-butyl-5-methyl-2-phenoxy)titanium dichloride, dimethylsilyl(n-butylcyclopentadienyl)(3,5-di-tert-butyl-2-phenoxy)titanium dichloride, dimethylsilyl(n-butylcyclopentadienyl)(5-methyl-3-phenyl-2-phenoxy)titanium dichloride, dimethylsilyl(n-butylcyclopentadienyl)(3-tert-butyldimethylsilyl-5-methyl-2-phenoxy)titanium dichloride, dimethylsilyl(n-butylcyclopentadienyl)(5-methyl-3-trimethylsilyl-2-phenoxy)titanium dichloride, dimethylsilyl(n-butylcyclopentadienyl)(3-tert-butyl-5-methoxy-2-phenoxy)titanium dichloride, dimethylsilyl(n-butylcyclopentadienyl)(3-tert-butyl-5-chloro-2-phenoxy)titanium dichloride, dimethylsilyl(n-butylcyclopentadienyl)(3,5-diamyl-2-phenoxy)titanium dichloride, dimethylsilyl(tert-butylcyclopentadienyl)(2-phenoxy)titanium dichloride, dimethylsilyl(tert-butylcyclopentadienyl)(3-methyl-2-phenoxy)titanium dichloride, dimethylsilyl(tert-butylcyclopentadienyl)(3,5-dimethyl-2-phenoxy)titanium dichloride, dimethylsilyl(tert-butylcyclopentadienyl)(3-tert-butyl-2-phenoxy)titanium dichloride, dimethylsilyl(tert-butylcyclopentadienyl)(3-tert-butyl-5-methyl-2-phenoxy)titanium dichloride, dimethylsilyl(tert-butylcyclopentadienyl)(3,5-di-tert-butyl-2-phenoxy)titanium dichloride, dimethylsilyl(tert-butylcyclopentadienyl)(5-methyl-3-phenyl-2-phenoxy)titanium dichloride, dimethylsilyl(tert-butylcyclopentadienyl)(3-tert-butyldimethylsilyl-5-methyl-2-phenoxy)titanium dichloride, dimethylsilyl(tert-butylcyclopentadienyl)(5-methyl-3-trimethylsilyl-2-phenoxy)titanium dichloride, dimethylsilyl(tert-butylcyclopentadienyl)(3-tert-butyl-5-methoxy-2-phenoxy)titanium dichloride, dimethylsilyl(tert-butylcyclopentadienyl)(3-tert-butyl-5-chloro-2-phenoxy)titanium dichloride, dimethylsilyl(tert-butylcyclopentadienyl)(3,5-diamyl-2-phenoxy)titanium dichloride, dimethylsilyl(tetramethylcyclopentadienyl)(2-phenoxy)titanium dichloride, dimethylsilyl(tetramethylcyclopentadienyl)(3-methyl-2-phenoxy)titanium dichloride, dimethylsilyl(tetramethylcyclopentadienyl)(3,5-dimethyl-2-phenoxy)titanium dichloride, dimethylsilyl(tetramethylcyclopentadienyl)(3-tert-butyl-2-phenoxy)titanium dichloride, dimethylsilyl(tetramethylcyclopentadienyl)(3-tert-butyl-5-methyl-2-phenoxy)titanium dichloride, dimethylsilyl(tetramethylcyclopentadienyl)(3,5-di-tert-butyl-2-phenoxy)titanium dichloride, dimethylsilyl(tetramethylcyclopentadienyl)(5-methyl-3-phenyl-2-phenoxy)titanium dichloride, dimethylsilyl(tetramethylcyclopentadienyl)(3-tert-butyldimethylsilyl-5-methyl-2-phenoxy)titanium dichloride, dimethylsilyl(tetramethylcyclopentadienyl)(5-methyl-3-trimethylsilyl-2-phenoxy)titanium dichloride, dimethylsilyl(tetramethylcyclopentadienyl)(3-tert-butyl-5-methoxy-2-phenoxy)titanium dichloride, dimethylsilyl(tetramethylcyclopentadienyl)(3-tert-butyl-5-chloro-2-phenoxy)titanium dichloride, dimethylsilyl(tetramethylcyclopentadienyl)(3,5-diamyl-2-phenoxy)titanium dichloride, dimethylsilyl(trimethylsilylcyclopentadienyl)(2-phenoxy)titanium dichloride, dimethylsilyl(trimethylsilylcyclopentadienyl)(3-methyl-2-phenoxy)titanium dichloride, dimethylsilyl(trimethylsilylcyclopentadienyl)(3,5-dimethyl-2-phenoxy)titanium dichloride, dimethylsilyl(trimethylsilylcyclopentadienyl)(3-tert-butyl-2-phenoxy)titanium dichloride, dimethylsilyl(trimethylsilylcyclopentadienyl)(3-tert-butyl-5-methyl-2-phenoxy)titanium dichloride, dimethylsilyl(trimethylsilylcyclopentadienyl)(3,5-di-tert-butyl-2-phenoxy)titanium dichloride, dimethylsilyl(trimethylsilylcyclopentadienyl)(5-methyl-3-phenyl-2-phenoxy)titanium dichloride, dimethylsilyl(trimethylsilylcyclopentadienyl)(3-tert-butyldimethylsilyl-5-methyl-2-phenoxy)titanium dichloride, dimethylsilyl(trimethylsilylcyclopentadienyl)(5-methyl-3-trimethylsilyl-2-phenoxy)titanium dichloride, dimethylsilyl(trimethylsilylcyclopentadienyl)(3-tert-butyl-5-methoxy-2-phenoxy)titanium dichloride, dimethylsilyl(trimethylsilylcyclopentadienyl)(3-tert-butyl-5-chloro-2-phenoxy)titanium dichloride, dimethylsilyl(trimethylsilylcyclopentadienyl)(3,5-diamyl-2-phenoxy)titanium dichloride, dimethylsilyl(indenyl)(2-phenoxy)titanium dichloride, dimethylsilyl(indenyl)(3-methyl-2-phenoxy)titanium dichloride, dimethylsilyl(indenyl)(3,5-dimethyl-2-phenoxy)titanium dichloride, dimethylsilyl(indenyl)(3-tert-butyl-2-phenoxy)titanium dichloride, dimethylsilyl(indenyl)(3-tert-butyl-5-methyl-2-phenoxy)titanium dichloride, dimethylsilyl(indenyl)(3,5-di-tert-butyl-2-phenoxy)titanium dichloride, dimethylsilyl(indenyl)(5-methyl-3-phenyl-2-phenoxy)titanium dichloride, dimethylsilyl(indenyl)(3-tert-butyldimethylsilyl-5-methyl-2-phenoxy)titanium dichloride, dimethylsilyl(indenyl)(5-methyl-3-trimethylsilyl-2-phenoxy)titanium dichloride, dimethylsilyl(indenyl)(3-tert-butyl-5-methoxy-2-phenoxy)titanium dichloride, dimethylsilyl(indenyl)(3-tert-butyl-5-chloro-2-phenoxy)titanium dichloride, dimethylsilyl(indenyl)(3,5-diamyl-2-phenoxy)titanium dichloride, dimethylsilyl(fluorenyl)(2-phenoxy)titanium dichloride, dimethylsilyl(fluorenyl)(3-methyl-2-phenoxy)titanium dichloride, dimethylsilyl(fluorenyl)(3,5-dimethyl-2-phenoxy)titanium dichloride, dimethylsilyl(fluorenyl)(3-tert-butyl-2-phenoxy)titanium dichloride, dimethylsilyl (fluorenyl)(3-tert-butyl-5-methyl-2-phenoxy)titanium dichloride, dimethylsilyl(fluorenyl)(3,5-di-tert-butyl-2-phenoxy)titanium dichloride, dimethylsilyl(fluorenyl)(5-methyl-3-phenyl-2-phenoxy)titanium dichloride, dimethylsilyl(fluorenyl)(3-tert-butyldimethylsilyl-5-methyl-2-phenoxy)titanium dichloride, dimethylsilyl (fluorenyl)(5-methyl-3-trimethylsilyl-2-phenoxy)titanium dichloride, dimethylsilyl(fluorenyl)(3-tert-butyl-5-methoxy-2-phenoxy)titanium dichloride, dimethylsilyl(fluorenyl)(3-tert-butyl-5-chloro-2-phenoxy)titanium dichloride, dimethylsilyl(fluorenyl)(3,5-diamyl-2-phenoxy)titanium dichloride and dimethylsilyl(tetramethylcyclopentadienyl)(1-naphthoxy-2-yl)titanium dichloride; and compounds resulting from changing, in the above-mentioned compounds, "(cyclopentadienyl)" to (dimethylcyclopentadienyl), (trimethylcyclopentadienyl), (ethylcyclopentadienyl), (n-propylcyclopentadienyl), (isopropylcyclopentadienyl), (sec-butylcyclopentadienyl), (isobutylcyclopentadienyl), (tert-butyldimethylsilylcyclopentadienyl), (phenylcyclopentadienyl), (methylindenyl) or (phenylindenyl), compounds resulting from changing, in the above-mentioned compounds, "2-phenoxy" to 3-phenyl-2-phenoxy, 3-trimethylsilyl-2-phenoxy or 3-tert-butyldimethylsilyl-2-phenoxy, compounds resulting from changing, in the above-mentioned compounds, "dimethylsilyl" to diethylsilyl, diphenylsilyl or dimethoxysilyl, compounds resulting from changing, in the above-mentioned compounds, "titanium" to zirconium or hafnium, and compounds resulting from changing, in the above-mentioned compounds, "chloride" to bromide, iodide, dimethylamide, diethylamide, n-butoxide or isopropoxide.

The compound [1] can be prepared by a process comprising the following 3 steps or 4 steps using as the starting material a halogenated aryl compound represented by the formula (10) (hereinafter referred to as compound [10]):

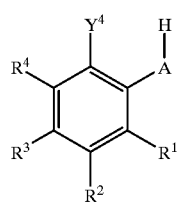

(10)

wherein $Y^4$ is a halogen atom, and $R^1$, $R^2$, $R^3$ and $R^4$ are respectively the same as defined above.

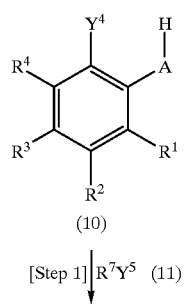

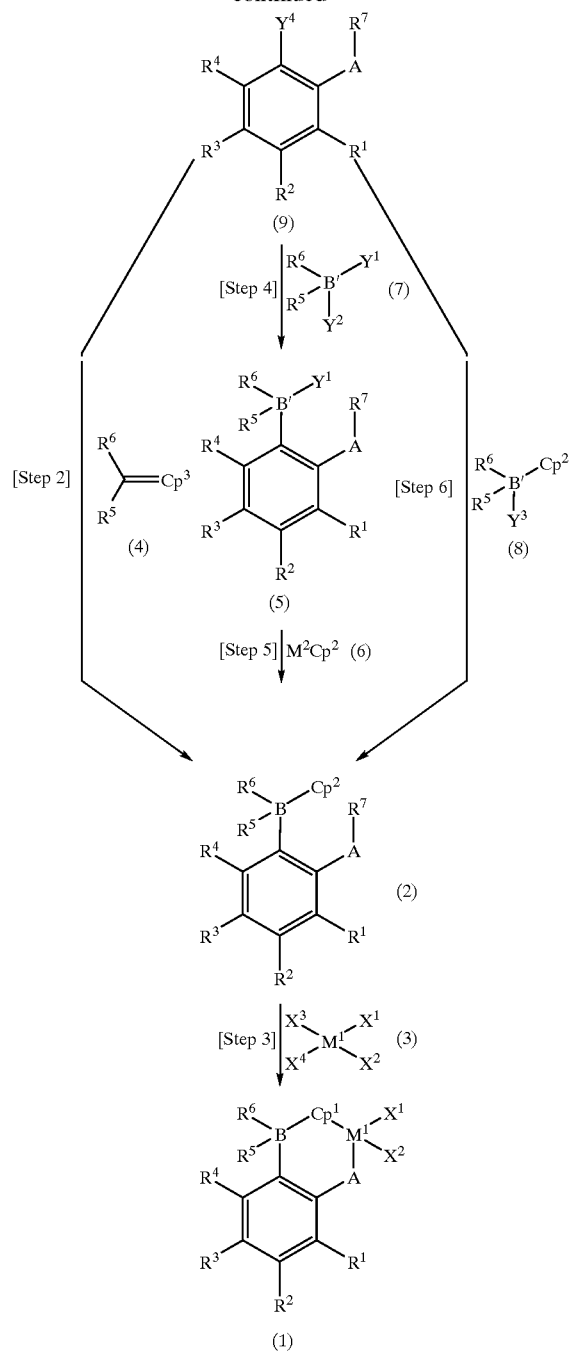

The halogen atom represented as the substituent $Y^4$ in the compound [10] may be, for example, a chlorine atom, bromine atom and iodine atom.

Examples of the compound [10] include 2-bromophenol, 2-bromo-6-methylphenol, 2-bromo-4,6-dimethylphenol, 2-bromo-6-tert-butylphenol, 2-bromo-6-tert-butyl-4-methylphenol, 2-bromo-4,6-di-tert-butylphenol, 2-bromo-6-trimethylsilylphenol, 2-bromo-4-methyl-6-trimethylsilylphenol, 2-bromo-6-tert-butyl-dimethylsilylphenol, 2-bromo-6-tert-butyldimethylsilyl-4-methylphenol, 2-bromo-6-phenylphenol, 2-bromo-4-methyl-6-phenylphenol, 4,6-diamyl-2-bromophenol, 2-bromo-6-tert-butyl-4-methoxyphenol, 2-bromo-6-tert-butyl-4-chlorophenol, and compounds resulting from changing, in the respective compounds described above, "bromo" to chloro or iodo.

The respective process steps are described in detail below.

[Step 3]

The step of producing the compound [1] by reacting a substituted cyclopentadienyl compound (hereinafter referred to as compound [2]) represented by the formula (2)

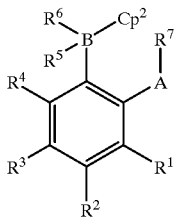

(2)

wherein $Cp^2$ is a group having a cyclopentadiene skeleton, $R^7$ is a hydrocarbon group optionally substituted with at least one halogen atom or a tri-substituted silyl group, and A, B, $R^1$, $R^2$, $R^3$, $R^4$, $R^5$ and $R^6$ are respectively the same as defined above, with a base, and then reacting the resulting reaction product with a transition metal compound represented by the formula (3) (hereinafter referred to as compound [3])

(3)

wherein $X^3$ and $X^4$ are each independently a hydrogen atom, a halogen atom, or a $C_1$–$C_{20}$ alkyl group, aralkyl group, aryl group, substituted silyl group, alkoxy group, aralkyloxy group or aryloxy group each optionally substituted with at least one halogen atom, or $C_2$–$C_{20}$ di-substituted amino group; $M^1$, $X^1$ and $X^2$ are respectively the same as defined above.

The group having a cyclopentadiene skeleton represented by the substituent $Cp^2$ in the compound [2] may be, for example, cyclopentadienyl group, methylcyclopentadienyl group, dimethylcyclopentadienyl group, trimethylcyclopentadienyl group, tetramethylcyclopentadienyl group, ethylcyclopentadienyl group, n-propylcyclopentadienyl group, isopropylcyclopentadienyl group, n-butylcyclopentadienyl group, sec-butylcyclopentadienyl group, tert-butylcyclopentadienyl group, n-pentylcyclopentadienyl group, neopentylcyclopentadienyl group, n-hexylcyclopentadienyl group, n-octylcyclopentadienyl group, phenylcyclopentadienyl group, naphthylcyclopentadienyl group, trimethylsilylcyclopentadienyl group, triethylsilylcyclopentadienyl group, tert-butyldimethylsilylcyclopentadienyl group, indenyl group, methylindenyl group, dimethylindenyl group, ethylindenyl group, n-propylindenyl group, isopropylindenyl group, n-butylindenyl group, sec-butylindenyl group, tert-butylindenyl group, n-pentylindenyl group, neopentylindenyl group, n-hexylindenyl group, n-octylindenyl group, n-decylindenyl group, phenylindenyl group, methylphenylindenyl group, naphthylindenyl group, trimethylsilylindenyl group, triethylsilylindenyl group, tert-butyldimethylsilylindenyl group, tetrahydroindenyl group, fluorenyl group, methylfluorenyl group, dimethylfluorenyl group, ethylfluorenyl group, diethylfluorenyl group, n-propylfluorenyl group, di-n-propylfluorenyl group, isopropylfluorenyl group, diisopropylfluorenyl group, n-butylfluorenyl group, sec-butylfluorenyl group, tert-butylfluorenyl group, di-n-butylfluorenyl group, di-sec-butylfluorenyl group, di-tert-butylfluorenyl group, n-pentylfluorenyl group, neopentylfluorenyl group, n-hexylfluorenyl group, n-octylfluorenyl group, n-decylfluorenyl group, n-dodecylfluorenyl group, phenylfluorenyl group, diphenylfluorenyl group, methylphenylfluorenyl group, naphthylfluorenyl group, trimethylsilylfluorenyl group, bis-trimethylsilylfluorenyl group, triethylsilylfluorenyl group and tert-butyldimethylsilylfluorenyl group, preferred of these being the cyclopentadienyl group, methylcyclopentadienyl group, tert-butylcyclopentadienyl group, tetramethylcyclopentadienyl group, fluorenyl group, indenyl group, etc.

The hydrocarbon group denoted as the substituent $R^7$ may be, for example, an alkyl group with the number of carbon atoms of 1–10, such as the methyl group, ethyl group, propyl group, hexyl group and decyl group, an alkenyl group with the number of carbon atoms of 2–10, such as the vinyl group, allyl group, propenyl group, 2-methyl-2-propenyl group, homoallyl group, hexenyl group and decenyl group, an alkoxyalkyl group, such as the methoxymethyl group and methoxyethoxymethyl group, and an aralkyl group with the number of carbon atoms of 7–12, such as the benzyl group, (4-methylphenyl)methyl group and (2,4,6-trimethylphenyl) methyl group. These hydrocarbon groups may each optionally be substituted with at least one halogen atom. Examples of the hydrocarbon group substituted with a halogen atom include the 2-chloro-2-propenyl group. The trisubstituted silyl group may be, for example, the trimethylsilyl group, triethylsilyl group, tri-n-propylsilyl group, triisopropylsilyl group, tri-n-butylsilyl group, tri-sec-butylsilyl group, tri-tert-butylsilyl group, triisobutylsilyl group, tert-butyldimethylsilyl group, tri-n-pentylsilyl group, tri-n-hexylsilyl group, tricyclohexylsilyl group and triphenylsilyl group. Among these substituents $R^7$, an alkenyl group, particularly the allyl group, is preferred because it can give the compound [1] with a good yield.

Such compounds [2] include a substituted cyclopentadienyl compound represented by the formula (2a) (hereinafter referred to as compound [2a]):

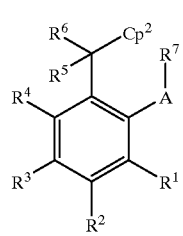

(2a)

wherein $Cp^2$, A, $R^1$, $R^2$, $R^3$, $R^4$, $R^5$, $R^6$ and $R^7$ are respectively the same as defined above, for example, 2-[(cyclopenta-1,4-dienyl)methyl]-1-methoxybenzene, 2-[(cyclopenta-1,4-dienyl)methyl]-1-methoxy-4,6-dimethylbenzene, 2-tert-butyl-6-[(cyclopenta-1,4-dienyl)methyl]-1-methoxy-4-methylbenzene, 6-[(cyclopenta-1,4-dienyl)methyl]-1-methoxy-2-phenylbenzene, 1-tert-butyldimethylsilyl-3-[(cyclopenta-1,4-dienyl)methyl]-2-methoxy-5-methylbenzene, 3-[(cyclopenta-1,4-dienyl)methyl]-2-methoxy-5-methyl-1-trimethylsilylbenzene, 2-tert-butyl-6-[(cyclopenta-1,4-dienyl)methyl]-1,4-dimethoxybenzene, 3-tert-butyl-1-chloro-5-

[(cyclopenta-1,4-dienyl)methyl]-4-methoxybenzene, 2-tert-butyl-6-[(cyclopenta-1,4-dienyl)methyl]-1-methoxybenzene, 2-[-(cyclopenta-1,4-dienyl)-1-methyl-ethyl]-1-methoxybenzene, 2-[1-(cyclopenta-1,4-dienyl)-1-methyl-ethyl]-1-methoxy-4,6-dimethylbenzene, 6-tert-butyl-2-[1-(cyclopenta-1,4-dienyl)-1-methyl-ethyl]-1-methoxy-4-methylbenzene, 6-[1-(cyclopenta-1,4-dienyl)-1-methyl-ethyl]-1-methoxy-2-phenylbenzene, 1-tert-butyldimethylsilyl-3-[1-(cyclopenta-1,4-dienyl)-1-methyl-ethyl]-2-methoxy-5-methylbenzene, 3-[1-(cyclopenta-1,4-dienyl)-1-methyl-ethyl]-2-methoxy-5-methyl-1-trimethylsilylbenzene, 6-tert-butyl-2-[1-(cyclopenta-1,4-dienyl)-1-methyl-ethyl]-1,4-dimethoxybenzene, 5-tert-butyl-1-chloro-3-[1-(cyclopenta-1,4-dienyl)-1-methyl-ethyl]-4-methoxybenzene, 6-tert-butyl-2-[1-(cyclopenta-1,4-dienyl)-1-methyl-ethyl]-1-methoxybenzene, 1-methoxy-2-[1-(4-methyl-cyclopenta-1,4-dienyl)-1-methyl-ethyl]benzene, 1-methoxy-4,6-dimethyl-2-[1-(4-methyl-cyclopenta-1,4-dienyl)-1-methyl-ethyl]benzene, 6-tert-butyl-1-methoxy-4-methyl-2-[1-(4-methyl-cyclopenta-1,4-dienyl)-1-methyl-ethyl]benzene, 1-methoxy-6-[-(4-methyl-cyclopenta-1,4-dienyl)-1-methyl-ethyl]-2-phenylbenzene, 1-tert-butyldimethylsilyl-2-methoxy-5-methyl-3-[1-(4-methyl-cyclopenta-1,4-dienyl)-1-methyl-ethyl]benzene, 2-methoxy-5-methyl-3-[1-(4-methyl-cyclopenta-1,4-dienyl)-1-methyl-ethyl]-1-trimethylsilylbenzene, 6-tert-butyl-1,4-dimethoxy-2-[1-(4-methyl-cyclopenta-1,4-dienyl)-1-methyl-ethyl]benzene, 5-tert-butyl-1-chloro-4-methoxy-3-[1-(4-methyl-cyclopenta-1,4-dienyl)-1-methyl-ethyl]benzene, 6-tert-butyl-1-methoxy-2-[1-(4-methyl-cyclopenta-1,4-dienyl)-1-methyl-ethyl]benzene, 2-[1-(4-tert-butyl-cyclopenta-1,4-dienyl)-1-methyl-ethyl]-1-methoxybenzene, 2-[1-(4-tert-butyl-cyclopenta-1,4-dienyl)-1-methyl-ethyl]-1-methoxy-4,6-dimethylbenzene, 6-tert-butyl-2-[1-(4-tert-butyl-cyclopenta-1,4-dienyl)-1-methyl-ethyl]-1-methoxy-4-methylbenzene, 6-[1-(4-tert-butyl-cyclopenta-1,4-dienyl)-1-methyl-ethyl]-1-methoxy-2-phenylbenzene, 1-tert-butyldimethylsilyl-3-[1-(4-tert-butyl-cyclopenta-1,4-dienyl)-1-methyl-ethyl]-2-methoxy-5-methylbenzene, 3-[1-(4-tert-butyl-cyclopenta-1,4-dienyl)-1-methyl-ethyl]-2-methoxy-5-methyl-1-trimethylsilylbenzene, 6-tert-butyl-2-[1-(4-tert-butyl-cyclopenta-1,4-dienyl)-1-methyl-ethyl]-1,4-dimethoxybenzene, 5-tert-butyl-1-chloro-3-[1-(4-tert-butyl-cyclopenta-1,4-dienyl)-1-methyl-ethyl]-4-methoxybenzene, 6-tert-butyl-2-[1-(4-tert-butyl-cyclopenta-1,4-dienyl)-1-methyl-ethyl]-1-methoxybenzene, 1-methoxy-2-[1-(2,3,4,5-tetramethyl-cyclopenta-1,4-dienyl)-1-methyl-ethyl]benzene, 1-methoxy-4,6-dimethyl-2-[1-(2,3,4,5-tetramethyl-cyclopenta-1,4-dienyl)-1-methyl-ethyl]benzene, 6-tert-butyl-1-methoxy-4-methyl-2-[1-(2,3,4,5-tetramethyl-cyclopenta-1,4-dienyl)-1-methyl-ethyl]benzene, 1-methoxy-2-phenyl-6-[1-(2,3,4,5-tetramethyl-cyclopenta-1,4-dienyl)-1-methyl-ethyl]benzene, 1-tert-butyldimethylsilyl-2-methoxy-5-methyl-3-[1-(2,3,4,5-tetramethyl-cyclopenta-1,4-dienyl)-1-methyl-ethyl]benzene, 2-methoxy-5-methyl-3-[1-(2,3,4,5-tetra-methyl-cyclopenta-1,4-dienyl)-1-methyl-ethyl]-1-trimethylsilylbenzene, 6-tert-butyl-1,4-dimethoxy-2-[1-(2,3,4,5-tetramethyl-cyclopenta-1,4-dienyl)-1-methyl-ethyl]benzene, 5-tert-butyl-1-chloro-4-methoxy-3-[1-(2,3,4,5-tetramethyl-cyclopenta-1,4-dienyl)-1-methyl-ethyl]benzene, 6-tert-butyl-1-methoxy-2-[1-(2,3,4,5-tetramethyl-cyclopenta-1,4-dienyl)-1-methyl-ethyl]benzene, 1-methoxy-2-[1-(3-trimethylsilyl-cyclopenta-1,4-dienyl)-1-methyl-ethyl]benzene, 1-methoxy-4,6-dimethyl-2-[1-(3-trimethylsilyl-cyclopenta-1,4-dienyl)-1-methyl-ethyl]benzene, 6-tert-butyl-1-methoxy-4-methyl-2-[1-(3-trimethylsilyl-cyclopenta-1,4-dienyl)-1-methyl-ethyl]benzene, 1-methoxy-2-phenyl-6-[1-(3-trimethylsilyl-cyclopenta-1,4-dienyl)-1-methyl-ethyl]benzene, 1-tert-butyldimethylsilyl-2-methoxy-5-methyl-3-[1-(3-trimethylsilyl-cyclopenta-1,4-dienyl)-1-methyl-ethyl]benzene, 2-methoxy-5-methyl-1-trimethylsilyl-3-[1-(3-trimethylsilyl-cyclopenta-1,4-dienyl)-1-methyl-ethyl]benzene, 6-tert-butyl-1,4-dimethoxy-2-[1-(3-trimethylsilyl-cyclopenta-1,4-dienyl)-1-methyl-ethyl]benzene, 5-tert-butyl-1-chloro-4-methoxy-3-[1-(3-trimethylsilyl-cyclopenta-1,4-dienyl)-1-methyl-ethyl]benzene, 6-tert-butyl-1-methoxy-2-[1-(3-trimethylsilyl-cyclopenta-1,4-dienyl)-1-methyl-ethyl]benzene, 2-[1-(cyclopenta-1,4-dienyl)-1-ethyl-propyl]-1-methoxybenzene, 2-[1-(cyclopenta-1,4-dienyl)-1-ethyl-propyl]-1-methoxy-4,6-dimethylbenzene, 6-tert-butyl-2-[1-(cyclopenta-1,4-dienyl)-1-ethyl-propyl]-1-methoxy-4-methylbenzene, 6-[1-(cyclopenta-1,4-dienyl)-1-ethyl-propyl]-1-methoxy-2-phenylbenzene, 1-tert-butyldimethylsilyl-3-[1-(cyclopenta-1,4-dienyl)-1-ethyl-propyl]-2-methoxy-5-methylbenzene, 3-[1-(cyclopenta-1,4-dienyl)-1-ethyl-propyl]-2-methoxy-5-methyl-1-trimethylsilylbenzene, 6-tert-butyl-2-[1-(cyclopenta-1,4-dienyl)-1-ethyl-propyl]-1,4-dimethoxybenzene, 5-tert-butyl-1-chloro-3-[1-(cyclopenta-1,4-dienyl)-1-ethyl-propyl]-4-methoxybenzene, 6-tert-butyl-2-[1-(cyclopenta-1,4-dienyl)-1-ethyl-propyl]-1-methoxybenzene, 2-[1-(cyclopenta-1,4-dienyl)-1,1-diphenylmethyl]-1-methoxybenzene, 2-[1-(cyclopenta-1,4-dienyl)-1,1-diphenylmethyl]-1-methoxy-4,6-dimethylbenzene, 6-tert-butyl-2-[1-(cyclopenta-1,4-dienyl)-1,1-diphenylmethyl]-1-methoxy-4-methylbenzene, 2-[1-(cyclopenta-1,4-dienyl)-1,1-diphenylmethyl]-1-methoxy-6-phenylbenzene, 1-tert-butyldimethylsilyl-3-[1-(cyclopenta-1,4-dienyl)-1,1-diphenylmethyl]-2-methoxy-5-methylbenzene, 3-[(cyclopenta-1,4-dienyl)-1,1-diphenylmethyl]-2-methoxy-5-methyl-1-trimethylsilylbenzene, 6-tert-butyl-2-[(cyclopenta-1,4-dienyl)-1,1-diphenylmethyl]-1,4-dimethoxybenzene, 5-tert-butyl-1-chloro-3-[(cyclopenta-1,4-dienyl)-1,1-diphenylmethyl]-4-methoxybenzene, 6-tert-butyl-2-[(cyclopenta-1,4-dienyl)-1,1-diphenylmethyl]-1-methoxybenzene, 1-allyloxy-2-[(cyclopenta-1,4-dienyl)methyl]benzene, 1-allyloxy-2-[(cyclopenta-1,4-dienyl)methyl]-4,6-dimethylbenzene, 1-allyloxy-2-tert-butyl-6-[(cyclopenta-1,4-dienyl)methyl]-4-methylbenzene, 1-allyloxy-6-[(cyclopenta-1,4-dienyl)methyl]-2-phenylbenzene, 2-allyloxy-1-tert-butyldimethylsilyl-3-[(cyclopenta-1,4-dienyl)methyl]-5-methylbenzene, 2-allyloxy-3-[(cyclopenta-1,4-dienyl)methyl]-5-methyl-1-trimethylsilylbenzene, 1-allyloxy-2-tert-butyl-6-[(cyclopenta-1,4-dienyl)methyl]-4-methoxybenzene, 4-allyloxy-3-tert-butyl-1-chloro-5-[(cyclopenta-1,4-dienyl)methyl]benzene, 1-allyloxy-2-tert-butyl-6-[(cyclopenta-1,4-dienyl)methyl]benzene, 1-allyloxy-2-[1-(cyclopenta-1,4-dienyl)-1-methyl-ethyl]benzene, 1-allyloxy-2-[1-(cyclopenta-1,4-dienyl)-1-methyl-ethyl]-4,6-dimethylbenzene, 1-allyloxy-6-tert-butyl-2-[1-(cyclopenta-1,4-dienyl)-1-methyl-ethyl]-4-methylbenzene, 1-allyloxy-6-[1-(cyclopenta-1,4-dienyl)-1-methyl-ethyl]-2-phenylbenzene, 2-allyloxy-1-tert-butyldimethylsilyl-3-[1-(cyclopenta-1,4-dienyl)-1-methyl-ethyl]-5-methylbenzene, 2-allyloxy-3-[1-(cyclopenta-1,4-dienyl)-1-methyl-ethyl]-5-methyl-1-trimethylsilylbenzene, 1-allyloxy-6-tert-butyl-2-[1-(cyclopenta-1,4-dienyl)-1-methyl-ethyl]-4- methoxybenzene, 4-allyloxy-5-tert-butyl-1-chloro-3-[1-(cyclopenta-1,4-dienyl)-1-methyl-ethyl]benzene, 1-allyloxy-6-tert-butyl-2-[1-(cyclopenta-1,4-dienyl)-1-methyl-ethyl]benzene, 1-allyloxy-2-[1-(4-methyl-cyclopenta-1,4-dienyl)-1-methyl-ethyl)benzene, 1-allyloxy-4,6-dimethyl-2-[1-(4-methyl-cyclopenta-1,4-dienyl)-1-methyl-ethyl]benzene, 1-allyloxy-6-tert-butyl-4-methyl-2-[1-(4-methyl-cyclopenta-1,4-dienyl)-1-methyl-ethyl]benzene, 1-allyloxy-6-[1-(4-methyl-cyclopenta-1,4-dienyl)-1-methyl-ethyl]-2-phenylbenzene, 2-allyloxy-1-tert-butyldimethylsilyl-5-methyl-3-[1-(4-methyl-cyclopenta-1,4-dienyl)-1-methyl-ethyl]benzene, 2-allyloxy-5-methyl-3-[1-(4-methyl-cyclopenta-1,4-dienyl)-1-methyl-ethyl]-1-trimethylsilylbenzene, 1-allyloxy-6-tert-butyl-4-methoxy-2-[1-(4-methyl-cyclopenta-1,4-dienyl)-1-methyl-ethyl]benzene, 4-allyloxy-5-tert-butyl-1-chloro-3-[1-(4-methyl-cyclopenta-1,4-dienyl)-1-methyl-ethyl]benzene, 1-allyloxy-6-tert-butyl-2-[1-(4-methyl-cyclopenta-1,4-dienyl)-1-methyl-ethyl]benzene, 1-allyloxy-2-[1-(4-tert-butyl-cyclopenta-1,4-dienyl)-1-methyl-ethyl]benzene, 1-allyloxy-2-[1-(4-tert-butyl-cyclopenta-1,4-dienyl)-1-methyl-ethyl]-4,6-dimethylbenzene, 1-allyloxy-6-tert-butyl-2-[1-(4-tert-butyl-cyclopenta-1,4-dienyl)-1-methyl-ethyl]-4-methylbenzene, 1-allyloxy-6-[1-(4-tert-butyl-cyclopenta-1,4-dienyl)-1-methyl-ethyl]-2-phenylbenzene, 2-allyloxy-1-tert-butyldimethylsilyl-3-[1-(4-tert-butyl-cyclopenta-1,4-dienyl)-1-methyl-ethyl]-5-methylbenzene, 2-allyloxy-3-[1-(4-tert-butyl-cyclopenta-1,4-dienyl)-1-methyl-ethyl]-5-methyl-1-trimethylsilylbenzene, 1-allyloxy-6-tert-butyl-2-[1-(4-tert-butyl-cyclopenta-1,4-dienyl)-1-methyl-ethyl]-4-methoxybenzene, 4-allyloxy-5-tert-butyl-1-chloro-3-[1-(4-tert-butyl-cyclopenta-1,4-dienyl)-1-methyl-ethyl]benzene, 1-allyloxy-6-tert-butyl-2-[1-(4-tert-butyl-cyclopenta-1,4-dienyl)-1-methyl-ethyl]benzene, 1-allyloxy-2-[1-(2,3,4,5-tetramethyl-cyclopenta-1,4-dienyl)-1-methyl-ethyl]benzene, 1-allyloxy-4,6-dimethyl-2-[1-(2,3,4,5-tetramethyl-cyclopenta-1,4-dienyl)-1-methyl-ethyl]benzene, 1-allyloxy-6-tert-butyl-4-methyl-2-[1-(2,3,4,5-tetramethyl-cyclopenta-1,4-dienyl)-1-methyl-ethyl]benzene, 1-allyloxy-2-phenyl-6-[1-(2,3,4,5-tetramethyl-cyclopenta-1,4-dienyl)-1-methyl-ethyl]benzene, 2-allyloxy-1-tert-butyldimethylsilyl-5-methyl-3-[1-(2,3,4,5-tetramethyl-cyclopenta-1,4-dienyl)-1-methyl-ethyl]benzene, 2-allyloxy-5-methyl-3-[1-(2,3,4,5-tetramethyl-cyclopenta-1,4-dienyl)-1-methyl-ethyl]-1-trimethylsilylbenzene, 1-allyloxy-6-tert-butyl-4-methoxy-2-[1-(2,3,4,5-tetramethyl-cyclopenta-1,4-dienyl)-1-methyl-ethyl]benzene, 4-allyloxy-5-tert-butyl-1-chloro-3-[1-(2,3,4,5-tetramethyl-cyclopenta-1,4-dienyl)-1-methyl-ethyl]benzene, 1-allyloxy-6-tert-butyl-2-[1-(2,3,4,5-tetramethyl-cyclopenta-1,4-dienyl)-1-methyl-ethyl]benzene, 1-allyloxy-2-[1-(3-trimethylsilyl-cyclopenta-1,4-dienyl)-1-methyl-ethyl]benzene, 1-allyloxy-4,6-dimethyl-2-[1-(3-trimethylsilyl-cyclopenta-1,4-dienyl)-1-methyl-ethyl]benzene, 1-allyloxy-6-tert-butyl-4-methyl-2-[1-(3-trimethylsilyl-cyclopenta-1,4-dienyl)-1-methyl-ethyl]benzene, 1-allyloxy-2-phenyl-6-[1-(3-trimethylsilyl-cyclopenta-1,4-dienyl)-1-methyl-ethyl]benzene, 2-allyloxy-1-tert-butyldimethylsilyl-5-methyl-3-[1-(3-trimethylsilyl-cyclopenta-1,4-dienyl)-1-methyl-ethyl]benzene, 2-allyloxy-5-methyl-1-trimethylsilyl-3-[1-(3-trimethylsilyl-cyclopenta-1,4-dienyl)-1-methyl-ethyl]benzene, 1-allyloxy-6-tert-butyl-4-methoxy-2-[1-(3-trimethylsilyl-cyclopenta-1,4-dienyl)-1-methyl-ethyl]benzene, 4-allyloxy-5-tert-butyl-1-chloro-3-[1-(3-trimethylsilyl-cyclopenta-1,4-dienyl)-1-methyl-ethyl]benzene, 1-allyloxy-6-tert-butyl-2-[1-(3-trimethylsilyl-cyclopenta-1,4-dienyl)-1-methyl-ethyl]benzene, 1-allyloxy-2-1-(cyclopenta-1,4-dienyl)-1-ethyl-propyl]benzene, 1-allyloxy-2-[1-(cyclopenta-1,4-dienyl)-1-ethyl-propyl]-4,6-dimethylbenzene, 1-allyloxy-6-tert-butyl-2-[1-(cyclopenta-1,4-dienyl)-1-ethyl-propyl]-4-methylbenzene, 1-allyloxy-6-[1-(cyclopenta-1,4-dienyl)-1-ethyl-propyl]-2-phenylbenzene, 2-allyloxy-1-tert-butyldimethylsilyl-3-[1-(cyclopenta-1,4-dienyl)-1-ethyl-propyl]-5-methylbenzene, 2-allyloxy-3-[1-(cyclopenta-1,4-dienyl)-1-ethyl-propyl]-5-methyl-1-trimethylsilylbenzene, 1-allyloxy-6-tert-butyl-2-[1-(cyclopenta-1,4-dienyl)-1-ethyl-propyl]-4-methoxybenzene, 4-allyloxy-5-tert-butyl-1-chloro-3-[1-(cyclopenta-1,4-dienyl)-1-ethyl-propyl]benzene, 1-allyloxy-6-tert-butyl-2-[1-(cyclopenta-1,4-dienyl)-1-ethyl-propyl]benzene, 1-allyloxy-2-[1-(cyclopenta-1,4-dienyl)-1,1-diphenylmethyl]benzene, 1-allyloxy-2-[1-(cyclopenta-1,4-dienyl)-1,1-diphenylmethyl]-4,6-dimethylbenzene, 1-allyloxy-6-tert-butyl-2-[1-(cyclopenta-1,4-dienyl)-1,1-diphenylmethyl]-4-methylbenzene, 1-allyloxy-2-[1-(cyclopenta-1,4-dienyl)-1,1-diphenylmethyl]-6-phenylbenzene, 2-allyloxy-1-tert-butyldimethylsilyl-3-[1-(cyclopenta-1,4-dienyl)-1,1-diphenylmethyl]-5-methylbenzene, 2-allyloxy-3-[(cyclopenta-1,4-dienyl)-1,1-diphenylmethyl]-5-methyl-1-trimethylsilylbenzene, 1-allyloxy-6-tert-butyl-2-[(cyclopenta-1,4-dienyl)-1,1-diphenylmethyl]-4-methoxybenzene, 4-allyloxy-5-tert-butyl-1-chloro-3-[(cyclopenta-1,4-dienyl)-1,1-diphenylmethyl]benzene, 1-allyloxy-6-tert-butyl-2-[(cyclopenta-1,4-dienyl)-1,1-diphenylmethyl]benzene; compounds resulting from changing, in the above-mentioned compounds, "methoxy" or "allyloxyl" to ethoxy, benzyloxy, trimethylsilyloxy, tert-butyldimethylsilyloxy or methoxymethoxy, compounds resulting from changing "cyclopenta-1,4-dienyl" to dimethylcyclopenta-1,4-dienyl, trimethylcyclopenta-1,4-dienyl, n-butylcyclopenta-1,4-dienyl, tert-butyldimethylsilylcyclopenta-1,4-dienyl, indenyl or fluorenyl, compounds resulting from changing "1-methoxybenzene" to 1-methoxy-6-methylbenzene, 1-methoxy-4,6-di-tert-butylbenzene, 1-methoxy-4-methyl-6-phenylbenzene, 1-tert-butyldimethylsilyl-2-methoxybenzene, or 2-methoxy-1-trimethylsilylbenzene, and a substituted cyclopentadienyl compound represented by the formula (2b) (hereinafter referred to as compound [2b]):

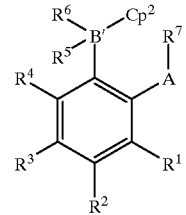

(2b)

wherein B' is an element of the group 14 of the periodic table of elements other than carbon atom, and A, $Cp^2$, $R^1$, $R^2$, $R^3$, $R^4$, $R^5$, $R^6$ and $R^7$ are respectively the same as defined above, for example, (cyclopenta-1,3-dienyl)(2-methoxyphenyl)dimethylsilane, (cyclopenta-1,3-dienyl)(2-methoxy-3-methylphenyl)dimethylsilane, (cyclopenta-1,3-dienyl)(2-methoxy-3,5-dimethylphenyl)dimethylsilane, (3-tert-butyl-2- methoxyphenyl)(cyclopenta-1,3-dienyl) dimethylsilane, (3-tert-butyl-2-methoxy-5-methylphenyl)(cyclopenta-1,3-dienyl)dimethylsilane, (3,5-di-tert-butyl-2-methoxyphenyl)(cyclopenta-1,3-dienyl)dimethylsilane, (cyclopenta-1,3-dienyl)(2-methoxy-5-methyl-3-phenylphenyl)dimethylsilane, (cyclopenta-1,3-dienyl)(2-methoxy-5-methyl-3-trimethylsilylphenyl)dimethylsilane, 3-(tert-butyl-dimethylsilyl-2-methoxy-5-methylphenyl)(cyclopenta-1,3-dienyl)dimethylsilane, (3,5-diamyl-2-methoxyphenyl)(cyclopenta-1,3-dienyl) dimethylsilane, (3-tert-butyl-2,5-dimethoxyphenyl)(cyclopenta-1,3-dienyl)dimethylsilane, (5-tert-butyl-3-chloro-6-methoxyphenyl)(cyclopenta-1,3-dienyl)dimethylsilane, (2-methoxyphenyl)(methylcyclopenta-1,3-dienyl)dimethylsilane, (2-methoxy-3-methylphenyl)(methylcyclopenta-1,3-dienyl)dimethylsilane, (2-methoxy-3,5-dimethylphenyl)(methylcyclopenta-1,3-dienyl) dimethyl-silane, (3-tert-butyl-2-methoxyphenyl)(methylcyclopenta-1,3-dienyl)dimethylsilane, (3-tert-butyl-2-methoxy-5-methylphenyl)(methylcyclopenta-1,3-dienyl)dimethylsilane, (3,5-di-tert-butyl-2-methoxyphenyl)(methylcyclopenta-1,3-dienyl)dimethylsilane, (2-methoxy-5-methyl-3-phenylphenyl)(methylcyclopenta-1,3-dienyl) dimethylsilane, (2-methoxy-5-methyl-3-trimethylsilylphenyl)(methylcyclopenta-1,3-dienyl)dimethylsilane, (3-tert-butyldimethylsilyl-2-methoxy-5-methylphenyl)(methylcyclopenta-1,3-dienyl) dimethylsilane, (3,5-diamyl-2-methoxyphenyl)(methylcyclopenta-1,3-dienyl)dimethylsilane, (3-tert-butyl-2,5-dimethoxyphenyl)(methylcyclopenta-1,3-dienyl)dimethylsilane, (5-tert-butyl-3-chloro-6-methoxyphenyl)(methylcyclopenta-1,3-dienyl)dimethylsilane, (2-methoxyphenyl)(2,3,4,5-tetramethylcyclopenta-1,3-dienyl)dimethylsilane, (2-methoxy-3-methylphenyl)(2,3,4,5-tetramethylcyclopenta-1,3-dienyl)dimethylsilane, (2-methoxy-3,5-dimethylphenyl)(2,3,4,5-tetramethylcyclopenta-1,3-dienyl)dimethylsilane, (3-tert-butyl-2-methoxyphenyl)(2,3,4,5-tetramethylcyclopenta-1,3-dienyl)dimethylsilane, (3-tert-butyl-2-methoxy-5-methylphenyl)(2,3,4,5-tetramethylcyclopenta-1,3-dienyl)dimethylsilane, (3,5-di-tert-butyl-2-methoxyphenyl)(2,3,4,5-tetramethylcyclopenta-1,3-dienyl)dimethylsilane, (2-methoxy-5-methyl-3-phenylphenyl)(2,3,4,5-tetramethylcyclopenta-1,3-dienyl)dimethylsilane, (2-methoxy-5-methyl-3-trimethylsilylphenyl)(2,3,4,5-tetramethylcyclopenta-1,3-dienyl)dimethylsilane, (3-tert-butyldimethylsilyl-2-methoxy-5-methylphenyl)(2,3,4,5-tetramethylcyclopenta-1,3-dienyl)dimethylsilane, (3,5-diamyl-2-methoxyphenyl)(2,3,4,5-tetramethylcyclopenta-1,3-dienyl)dimethylsilane, (3-tert-butyl-2,5-dimethoxyphenyl)(2,3,4,5-tetramethylcyclopenta-1,3-dienyl )dimethylsilane, (5-tert-butyl-3-chloro-6-methoxyphenyl)(2,3,4,5-tetramethylcyclopenta-1,3-dienyl)dimethylsilane, (tert-butylcyclopenta-1,3-dienyl)(2-methoxyphenyl) dimethylsilane, (tert-butylcyclopenta-1,3-dienyl)(2-methoxy-3-methylphenyl)dimethylsilane, (tert-butylcyclopenta-1,3-dienyl)(2-methoxy-3,5-dimethylphenyl)dimethylsilane, (tert-butylcyclopenta-1,3-dienyl)(3-tert-butyl-2-methoxyphenyl)dimethylsilane, (tert-butylcyclopenta-1,3-dienyl)(3-tert-butyl-2-methoxy-5-methylphenyl)dimethylsilane, (tert-butylcyclopenta-1,3-dienyl)(3,5-di-tert-butyl-2-methoxyphenyl)dimethylsilane, (tert-butylcyclopenta-1,3-dienyl)(2-methoxy-5-methyl-3-phenylphenyl)dimethylsilane, (tert-butylcyclopenta-1,3-dienyl)(2-methoxy-5-methyl-3-trimethylsilylphenyl)dimethylsilane, (tert-butylcyclopenta-1,3-dienyl)(3-tert-butyldimethylsilyl-2-methoxy-5-methylphenyl)dimethylsilane, (3,5-diamyl-2-methoxyphenyl)(tert-butylcyclopenta-1,3-dienyl)dimethylsilane, (tert-butylcyclopenta-1,3-dienyl)(3-tert-butyl-2,5-dimethoxyphenyl)dimethylsilane, (5-tert-butyl-3-chloro-6-methoxyphenyl)(tert-butylcyclopenta-1,3-dienyl) dimethylsilane, (2-methoxyphenyl)(trimethylsilylcyclopenta-1,3-dienyl)dimethylsilane, (2-methoxy-3-methylphenyl)(trimethylsilylcyclopenta-1,3-dienyl)dimethylsilane, (2-methoxy-3,5-dimethylphenyl)(trimethylsilylcyclopenta-1,3-dienyl)dimethylsilane, (3-tert-butyl-2-methoxyphenyl)(trimethylsilylcyclopenta-1,3-dienyl)dimethylsilane, (3-tert-butyl-2-methoxy-5-methylphenyl)(trimethylsilylcyclopenta-1,3-dienyl)dimethylsilane, (3,5-di-tert-butyl-2-methoxyphenyl)(trimethylsilylcyclopenta-1,3-dienyl)dimethylsilane, (2-methoxy-5-methyl-3-phenylphenyl)(trimethylsilylcyclopenta-1,3-dienyl)dimethylsilane, (2-methoxy-5-methyl-3-trimethylsilylphenyl)(trimethylsilylcyclopenta-1,3-dienyl)dimethylsilane, (3-tert-butyldimethylsilyl-2-methoxy-5-methylphenyl)(trimethylsilylcyclopenta-1,3-dienyl)dimethylsilane, (3,5-diamyl-2-methoxyphenyl)(trimethylsilylcyclopenta-1,3-dienyl)dimethylsilane, (3-tert-butyl-2,5-dimethoxyphenyl)(trimethylsilylcyclopenta-1,3-dienyl)dimethylsilane, (5-tert-butyl-3-chloro-6-methoxyphenyl)(trimethylsilylcyclopenta-1,3-dienyl)dimethylsilane, (inden-1-yl)(2-methoxyphenyl)dimethylsilane, (inden-2-yl)(2-methoxyphenyl)dimethylsilane, (inden-1-yl)(2-methoxy-3-methylphenyl)dimethylsilane, (inden-2-yl)(2-methoxy-3-methylphenyl)dimethylsilane, (inden-1-yl)(2-methoxy-3,5-dimethylphenyl)dimethylsilane, (inden-2-yl)(2-methoxy-3,5-dimethylphenyl)dimethylsilane, (3-tert-butyl-2-methoxyphenyl)(inden-1-yl)dimethylsilane, (3-tert-butyl-2-methoxyphenyl)(inden-2-yl)dimethylsilane, (3-tert-butyl-2-methoxy-5-methylphenyl)(inden-1-yl) dimethylsilane, (3-tert-butyl-2-methoxy-5-methylphenyl)(inden-2-yl)dimethylsilane, (3,5-di-tert-butyl-2-methoxyphenyl)(inden-1-yl)dimethylsilane, (3,5-di-tert-butyl-2-methoxyphenyl)(inden-2-yl)dimethylsilane, (inden-1-yl)(2-methoxy-5-methyl-3-phenylphenyl)dimethylsilane, (inden-2-yl)(2-methoxy-5-methyl-3-phenylphenyl) dimethylsilane, (inden-1-yl)(2-methoxy-5-methyl-3-trimethylsilylphenyl)dimethylsilane, (inden-2-yl)(2-methoxy-5-methyl-3-trimethylsilylphenyl)dimethylsilane, (3-tert-butyldimethylsilyl-2-methoxy-5-methylphenyl) (inden-1-yl)dimethylsilane, (3-tert-butyldimethylsilyl-2-methoxy-5-methylphenyl)(inden-2-yl)dimethylsilane, (3,5-diamyl-2-methoxyphenyl)(inden-1-yl)dimethylsilane, (3,5-diamyl-2-methoxyphenyl)(inden-2-yl)dimethylsilane, (3-tert-butyl-2,5-dimethoxyphenyl)(inden-1-yl) dimethylsilane, (3-tert-butyl-2,5-dimethoxyphenyl)(inden-2-yl)dimethylsilane, (5-tert-butyl-3-chloro-6-methoxyphenyl)(inden-1-yl)dimethylsilane, (5-tert-butyl-3-chloro-6-methoxyphenyl)(inden-2-yl)dimethylsilane, (9H-fluoren-9-yl)(2-methoxyphenyl)dimethylsilane, (9H-fluoren-9-yl)(2-methoxy-3-methylphenyl)dimethylsilane, (9H-fluoren-9-yl)(2-methoxy-3,5-dimethylphenyl) dimethylsilane, (3-tert-butyl-2-methoxyphenyl)(9H-fluoren-9-yl)dimethylsilane, (3-tert-butyl-2-methoxy-5-methylphenyl)(9H-fluoren-9-yl)dimethylsilane, (3,5-di-tert-butyl-2-methoxyphenyl)(9H-fluoren-9-yl)dimethylsilane, (9H-fluoren-9-yl)(2-methoxy-5-methyl-3-phenylphenyl) dimethylsilane, (9H-fluoren-9-yl)(2-methoxy-5-methyl-3- trimethylsilylphenyl)dimethylsilane, (3-tert-butyldimethylsilyl-2-methoxy-5-methylphenyl)(9H-fluoren-9-yl)dimethylsilane, (3,5-diamyl-2-methoxyphenyl)(9H-fluoren-9-yl)dimethylsilane, (3-tert-butyl-2,5-dimethoxyphenyl)(9H-fluoren-9-yl)dimethylsilane, (5-tert-butyl-3-chloro-6-methoxyphenyl)(9H-fluoren-9-yl)dimethylsilane, (2-allyloxyphenyl)(cyclopenta-1,3-dienyl)dimethylsilane, (2-allyloxy-3-methylphenyl)(cyclopenta-1,3-dienyl)dimethylsilane, (2-allyloxy-3,5-dimethylphenyl)(cyclopenta-1,3-dienyl)dimethylsilane, (2-allyloxy-3-tert-butylphenyl)(cyclopenta-1,3-dienyl)dimethylsilane, (2-allyloxy-3-tert-butyl-5-methylphenyl)(cyclopenta-1,3-dienyl)dimethylsilane, (2-allyloxy-3,5-di-tert-butylphenyl)(cyclopenta-1,3-dienyl)dimethylsilane, (2-allyloxy-5-methyl-3-phenylphenyl)(cyclopenta-1,3-dienyl)dimethylsilane, (2-allyloxy-5-methyl-3-trimethylsilylphenyl)(cyclopenta-1,3-dienyl)dimethylsilane, (2-allyloxy-3-tert-butyldimethylsilyl-5-methylphenyl)(cyclopenta-1,3-dienyl)dimethylsilane, (2-allyloxy-3,5-diamylphenyl)(cyclopenta-1,3-dienyl)dimethylsilane, (2-allyloxy-3-tert-butyl-5-methoxyphenyl)(cyclopenta-1,3-dienyl)dimethylsilane, (6-allyloxy-5-tert-butyl-3-chlorophenyl)(cyclopenta-1,3-dienyl)dimethylsilane, (2-allyloxyphenyl)(methylcyclopenta-1,3-dienyl)dimethylsilane, (2-allyloxy-3-methylphenyl)(methylcyclopenta-1,3-dienyl)dimethylsilane, (2-allyloxy-3,5-dimethylphenyl)(methylcyclopenta-1,3-dienyl)dimethylsilane, (2-allyloxy-3-tert-butylphenyl)(methylcyclopenta-1,3-dienyl)dimethylsilane, (2-allyloxy-3-tert-butyl-5-methylphenyl)(methylcyclopenta-1,3-dienyl)dimethylsilane, (2-allyloxy-3,5-di-tert-butylphenyl)(methylcyclopenta-1,3-dienyl)dimethylsilane, (2-allyloxy-5-methyl-3-phenylphenyl)(methylcyclopenta-1,3-dienyl)dimethylsilane, (2-allyloxy-5-methyl-3-trimethylsilylphenyl)(methylcyclopenta-1,3-dienyl)dimethylsilane, (2-allyloxy-3-tert-butyldimethylsilyl-5-methylphenyl)(methylcyclopenta-1,3-dienyl)dimethylsilane, (2-allyloxy-3,5-diamylphenyl)(methylcyclopenta-1,3-dienyl)dimethylsilane, (2-allyloxy-3-tert-butyl-5-methoxyphenyl)(methylcyclopenta-1,3-dienyl)dimethylsilane, (6-allyloxy-5-tert-butyl-3-chlorophenyl)(methylcyclopenta-1,3-dienyl)dimethylsilane, (2-allyloxyphenyl)(2,3,4,5-tetramethylcyclopenta-1,3-dienyl)dimethylsilane, (2-allyloxy-3-methylphenyl)(2,3,4,5-tetramethylcyclopenta-1,3-dienyl)dimethylsilane, (2-allyloxy-3,5-dimethylphenyl)(2,3,4,5tetramethylcyclopenta-1,3-dienyl)dimethylsilane, (2-allyloxy-3-tert-butylphenyl)(2,3,4,5-tetramethylcyclopenta-1,3-dienyl)dimethylsilane, (2-allyloxy-3-tert-butyl-5-methylphenyl)(2,3,4,5-tetramethylcyclopenta-1,3-dienyl)dimethylsilane, (2-allyloxy-3,5-di-tert-butylphenyl)(2,3,4,5-tetramethylcyclopenta-1,3-dienyl)dimethylsilane, (2-allyloxy-5-methyl-3-phenylphenyl)(2,3,4,5-tetramethylcyclopenta-1,3-dienyl)dimethylsilane, (2-allyloxy-5-methyl-3-trimethylsilylphenyl)(2,3,4,5-tetramethylcyclopenta-1,3-dienyl)dimethylsilane, (2-allyloxy-3-tert-butyldimethylsilyl-5-methylphenyl)(2,3,4,5-tetramethylcyclopenta-1,3-dienyl)dimethylsilane, (2-allyloxy-3,5-diamylphenyl)(2,3,4,5-tetramethylcyclopenta-1,3-dienyl)dimethylsilane, (2-allyloxy-3-tert-butyl-5-methoxyphenyl)(2,3,4,5-tetramethylcyclopenta-1,3-dienyl)dimethylsilane, (6-allyloxy-5-tert-butyl-3-chlorophenyl)(2,3,4,5-tetramethylcyclopenta-1,3-dienyl)dimethylsilane, (2-allyloxyphenyl)(tert-butylcyclopenta-1,3-dienyl)dimethylsilane, (2-allyloxy-3-methylphenyl)(tert-butylcyclopenta-1,3-dienyl)dimethylsilane, (2-allyloxy-3,5-dimethylphenyl)(tert-butylcyclopenta-1,3-dienyl)dimethylsilane, (2-allyloxy-3-tert-butylphenyl)(tert-butylcyclopenta-1,3-dienyl)dimethylsilane, (2-allyloxy-3-tert-butyl-5-methylphenyl)(tert-butylcyclopenta-1,3-dienyl)dimethylsilane, (2-allyloxy-3,5-di-tert-butylphenyl)(tert-butylcyclopenta-1,3-dienyl)dimethylsilane, (2-allyloxy-5-methyl-3-phenylphenyl)(tert-butylcyclopenta-1,3-dienyl)dimethylsilane, (2-allyloxy-5-methyl-3-trimethylsilylphenyl)(tert-butylcyclopenta-1,3-dienyl)dimethylsilane, (2-allyloxy-3-tert-butyldimethylsilyl-5-methylphenyl)(tert-butylcyclopenta-1,3-dienyl)dimethylsilane, (2-allyloxy-3,5-diamylphenyl)(tert-butylcyclopenta-1,3-dienyl)dimethylsilane, (2-allyloxy-3-tert-butyl-5-methoxyphenyl)(tert-butylcyclopenta-1,3-dienyl)dimethylsilane, (6-allyloxy-5-tert-butyl-3-chlorophenyl)(tert-butylcyclopenta-1,3-dienyl)dimethylsilane, (2-allyloxyphenyl)(trimethylsilylcyclopenta-1,3-dienyl)dimethylsilane, (2-allyloxy-3-methylphenyl)(trimethylsilylcyclopenta-1,3-dienyl)dimethylsilane, (2-allyloxy-3,5-dimethylphenyl)(trimethylsilylcyclopenta-1,3-dienyl)dimethylsilane, (2-allyloxy-3-tert-butylphenyl)(trimethylsilylcyclopenta-1,3-dienyl)dimethylsilane, silane, (2-allyloxy-3-tert-butyl-5-methylphenyl)(trimethylsilylcyclopenta-1,3-dienyl)dimethylsilane, (2-allyloxy-3,5-di-tert-butylphenyl)(trimethylsilylcyclopenta-1,3-dienyl)dimethylsilane, (2-allyloxy-5-methyl-3-phenylphenyl)(trimethylsilylcyclopenta-1,3-dienyl)dimethylsilane, (2-allyloxy-5-methyl-3-trimethylsilylphenyl)(trimethylsilylcyclopenta-1,3-dienyl)dimethylsilane, (2-allyloxy-3-tert-butyldimethylsilyl-5-methylphenyl)(trimethylsilylcyclopenta-1,3-dienyl)dimethylsilane, (2-allyloxy-3,5-diamylphenyl)(trimethylsilylcyclopenta-1,3-dienyl)dimethylsilane, (2-allyloxy-3-tert-butyl-5-methoxyphenyl)(trimethylsilylcyclopenta-1,3-dienyl)dimethylsilane, (6-allyloxy-5-tert-butyl-3-chlorophenyl)(trimethylsilylcyclopenta-1,3-dienyl)dimethylsilane, (2-allyloxyphenyl)(inden-1-yl)dimethylsilane, (2-allyloxyphenyl)(inden-2-yl)dimethylsilane, (2-allyloxy-3-methylphenyl)(inden-1-yl)dimethylsilane, (2-allyloxy-3-methylphenyl)(inden-2-yl)dimethylsilane, (2-allyloxy-3,5-dimethylphenyl)(inden-1-yl)dimethylsilane, (2-allyloxy-3,5-dimethylphenyl)(inden-2-yl)dimethylsilane, (2-allyloxy-3-tert-butylphenyl)(inden-1-yl)dimethylsilane, (2-allyloxy-3-tert-butylphenyl)(inden-2-yl)dimethylsilane, (2-allyloxy-3-tert-butyl-5-methylphenyl)(inden-1-yl)dimethylsilane, (2-allyloxy-3-tert-butyl-5-methylphenyl)(inden-2-yl)dimethylsilane, (2-allyloxy-3,5-di-tert-butylphenyl)(inden-1-yl)dimethylsilane, (2-allyloxy-3,5-di-tert-butylphenyl)(inden-2-yl)dimethylsilane, (2-allyloxy-5-methyl-3-phenylphenyl)(inden-1-yl)dimethylsilane, (2-allyloxy-5-methyl-3-phenylphenyl)(inden-2-yl)dimethylsilane, (2-allyloxy-5-methyl-3-trimethylsilylphenyl)(inden-1-yl)dimethylsilane, (2-allyloxy-5-methyl-3-trimethylsilylphenyl)(inden-2-yl)dimethylsilane, (2-allyloxy-3-tert-butyldimethylsilyl-5-methylphenyl)(inden-1-yl)dimethylsilane, (2-allyloxy-3-tert-butyldimethylsilyl-5-methylphenyl)(inden-2-yl)dimethylsilane, (2-allyloxy-3,5-diamylphenyl)(inden-1-yl)dimethylsilane, (2-allyloxy-3,5-diamylphenyl)(inden-2-yl)dimethylsilane, (2-allyloxy-3-tert-butyl-5-methoxyphenyl)(inden-1-yl)dimethylsilane, (2-allyloxy-3-tert-butyl-5-methoxyphenyl)(inden-2-yl)dimethylsilane, (6-allyloxy-5-tert-butyl-3-chlorophenyl)(inden-1-yl)dimethylsilane, (6-allyloxy-5-tert-butyl-3-chlorophenyl)(inden-2-yl) dimethylsilane, (2-allyloxyphenyl)(9H-fluoren-9-yl)dimethylsilane, (2-allyloxy-3-methylphenyl)(9H-fluoren-9-yl) dimethylsilane, (2-allyloxy-3,5-dimethylphenyl)(9H-fluoren-9-yl)dimethylsilane, (2-allyloxy-3-tert-butylphenyl) (9H-fluoren-9-yl)dimethylsilane, (2-allyloxy-3-tert-butyl-5-methylphenyl)(9H-fluoren-9-yl)dimethylsilane, (2-allyloxy-3,5-di-tert-butylphenyl)(9H-fluoren-9-yl)dimethylsilane, (2-allyloxy-5-methyl-3-phenylphenyl)(9H-fluoren-9-yl) dimethylsilane, (2-allyloxy-5-methyl-3-trimethylsilylphenyl)(9H-fluoren-9-yl)dimethylsilane, (2-allyloxy-3-tert-butyldimethylsilyl-5-methylphenyl)(9H-fluoren-9-yl)dimethylsilane, (2-allyloxy-3,5diamylphenyl) (9H-fluoren-9-yl)dimethylsilane, (2-allyloxy-3tert-butyl-5-methoxyphenyl)(9H-fluoren-9yl)dimethylsilane, (6-allyloxy-5-tert-butyl-3-chlorophenyl)(9H-fluoren-9-yl) dimethylsilane, and (1-allyloxynaphthalene-2-yl)dimethyl (1,2,3,4-tetramethylcyclopentadienyl)silane; compounds resulting from changing, in the above mentioned compounds, "methoxyn" or "allyloxy" to benzyloxy, ethoxy, trimethylsilyloxy, tert-butyldimethylsilyloxy or methoxymethoxy, compounds resulting from changing "dimethylsilane" to diethylsilane, diphenylsilane or dimethoxysilane, compounds resulting from changing "cyclopentadienyl" to dimethylcyclopentadienyl, trimethylcyclopentadienyl, n-propylcyclopentadienyl, isopropylcyclopentadienyl, n-butylcyclopentadienyl, isobutylcyclopentadienyl, sec-butylcyclopentadienyl, tert-butyldimethylsilylcyclopentadienyl, phenylcyclopentadienyl or methylindenyl and compounds resulting from changing "2-methoxyphenyl" to 3-phenyl-2-methoxyphenyl, 3-trimethylsilyl-2-methoxyphenyl or 3-tert-butyldimethylsilyl-2-methoxyphenyl.

These compounds [2] sometimes have a plural number of isomers originating from difference in the position of a substituent or in the position of a double bond in the cyclopentadiene skeleton of the substituent $Cp^2$. The compounds [2] in the present invention include all of these isomers.

In the compound [3], the hydrogen atom, halogen atom, alkyl group with the number of carbon atoms of 1–20 optionally substituted with at least one halogen atom, aralkyl group with the number of carbon atoms of 7–20 optionally substituted with at least one halogen atom, aryl group with the number of carbon atoms of 6–20 optionally substituted with at least one halogen atom, substituted silyl group with the number of carbon atoms of 1–20 optionally substituted with at least one halogen atom, alkoxy group with the number of carbon atoms of 1–20 optionally substituted with at least one halogen atom, aralkyloxy group with the number of carbon atoms of 1–20 optionally substituted with at least one halogen atom, aryloxy group with the number of carbon atoms of 1–20 optionally substituted with at least one halogen atom, and di-substituted amino group with the number of carbon atoms of 2–20 which are represented as the substituents $X^3$ and $X^4$ may respectively be the same as those represented as the substituents $X^1$ and $X^2$ in the compound [1].

Examples of the compound [3] include titanium halides, e.g., titanium tetrachloride, titanium tetrabromide and titanium tetraiodide, amidotitanium, e.g., tetrakis (dimethylamino)titanium, dichlorobis(dimethylamino) titanium, trichloro(dimethylamino)titanium and tetrakis (diethylamino)titanium, alkoxytitanium, e.g., tetraisopropoxytitanium, tetra-n-butoxytitanium, dichlorodiisopropoxytitanium and trichloroisopropoxytitanium, and compounds resulting from changing the "titanium" of the respective compounds mentioned above to zirconium or hafnium. The amount of the compound [3] to be used is in the range of usually 0.5–3 times by mole, preferably 0.7–1.5 times by mole the amount of the compound [2].

The base may be, for example, an organoalkali metal compound, e.g., an organolithium compound, such as methyllithium, ethyllithium, n-butyllithium, sec-butyllithium, tert-butyllithium, lithium trimethylsilylacetylide, lithium acetylide, trimethylsilylmethylyllithium, vinyllithium, phenyllithium and allyllithium. The amount of the base to be used is in the range of usually 0.5–5 times by mole the amount of the compound [2].

Further, an amine compound may be used together with the base. The amine compound may be, for example, a primary amine compound, such as methylamine, ethylamine, n-propylamine, isopropylamine, n-butylamine, tert-butylamine, n-octylamine, n-decylamine, aniline and ethylenediamine, secondary amine compound, such as dimethylamine, diethylamine, di-n-propylamine, di-n-propylamine, di-n-butylamine, di-tert-butylamine, di-n-octylamine, di-n-decylamine, pyrrolidine, hexamethyldisilazane, and diphenylamine, and tertiary amine compound, such as trimethylamine, triethylamine, tri-n-propylamine, tri-n-butylamine, diisopropylethylamine, tri-n-octylamine, tri-n-decylamine, triphenylamine, N,N-dimethylaniline, N,N,N',N'-tetramethylethylenediamine, N-methylpyrrolidine and 4-dimethylaminopyridine. The amount of the amine compound to be used is in the range of usually 10 times by mole or less, preferably 0.5–10 times by mole, more preferably 1–3 times by mole the amount of the base.

The reaction is usually conducted in a solvent inert to the reaction. Such a solvent is, for example, an aprotic solvent, e.g., aromatic hydrocarbon solvent, such as benzene and toluene, aliphatic hydrocarbon solvent, such as hexane and heptane, ether type solvent, such as diethyl ether, tetrahydrofuran and 1,4-dioxane, amide type solvent, such as hexamethylphosphoric amide and dimethylformamide, polar solvent, such as acetonitrile, propionitrile, acetone, diethyl ketone, methyl isobutyl ketone and cyclohexanone, halogen-containing solvent, such as dichloromethane, dichloroethane, chlorobenzene and dichlorobenzene. These solvents may be used each alone or as a mixture of two or more thereof. The amount of the solvent to be used is in the range of usually 1–200 times by weight, preferably 3–50 times by weight the amount of the compound [2].

The present step may usually be conducted by adding the compound [2] and the base to the solvent and then adding the compound [3] thereto. Sometimes a solid will precipitate out after the addition of the compound (2) and the base. In such a case, the solid taken out from the reaction system may be added to a solvent and then the compound [3] is added thereto. Further, the compound [2], the base and the compound [3] may simultaneously be added to the solvent. The reaction temperature is in the range of usually from not lower than −100° C. to not higher than the boiling point of the solvent, preferably from −80° C. to +100° C.

The reaction system is preferably shielded from light to obtain a better yield of the compound [1].

The intended compound [1] can be obtained from the resulting reaction mixture by a conventional method, for example, by filtering off the precipitate formed, concentrating the filtrate to precipitate the compound [1] and then collecting the compound [1] by filtration.

As described above, the compound [2] used in the above [step 1] include the compounds [2a] and the compounds

[2b]. The compound [2a] can be prepared through the [step 2] as described below.

[Step 2]

The step of preparing the compound [2a] by reacting a halogenated aryl compound represented by the formula (9) (hereinafter referred to as compound [9]):

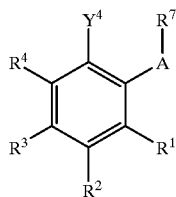

(9)

wherein A, $R^1$, $R^2$, $R^3$, $R^4$, $R^7$ and $Y^4$ are respectively the same as defined above, with an organoalkali metal salt or metallic magnesium, then reacting the reaction product with a cyclopentadienylidene compound represented by the formula (4) (hereinafter referred to as compound [4]):

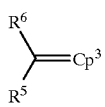

(4)

wherein $Cp^3$ is a group having a cyclopentadienylidene skeleton, and $R^5$ and $R^6$ are respectively the same as defined above, and then reacting the resulting reaction product with water.

The compound [9] may be, for example, 1-bromo-2-methoxybenzene, 1-bromo-3-methyl-2-methoxybenzene, 1-bromo-3,5-dimethyl-2-methoxybenzene, 1-bromo-3-tert-butyl-2-methoxybenzene, 1-bromo-3-tert-butyl-2-methoxy-5-methylbenzene, 1-bromo-3,5-di-tert-butyl-2-methoxybenzene, 1-bromo-2-methoxy-3-phenylbenzene, 1-bromo-2-methoxy-5-methyl-3-phenylbenzene, 1-bromo-2-methoxy-3-trimethylsilylbenzene, 1-bromo-2-methoxy-5-methyl-3-trimethylsilylbenzene, 1-bromo-3-tert-butyldimethylsilyl-2-methoxybenzene, 1-bromo-3-tert-butyldimethylsilyl-2-methoxy-5-methylbenzene, 1-bromo-3-tert-butyl-2,5-dimethoxybenzene, 1-bromo-3-tert-butyl-5-chloro-2-methoxybenzene, 3,5-diamyl-1-bromo-2-methoxybenzene,
2-allyloxy-1-bromobenzene, 2-allyloxy-1-bromo-3-methylbenzene, 2-allyloxy-1-bromo-3,5-dimethylbenzene, 2-allyloxy-1-bromo-3-tert-butylbenzene, 2-allyloxy-1-bromo-3-tert-butyl-5-methylbenzene, 2-allyloxy-1-bromo-3,5-di-tert-butylbenzene, 2-allyloxy-1-bromo-3-phenylbenzene, 2-allyloxy-1-bromo-5-methyl-3-phenylbenzene, 2-allyloxy-1-bromo-3-trimethylsilylbenzene, 2-allyloxy-1-bromo-5-methyl-3-trimethylsilylbenzene, 2-allyloxy-1-bromo-3-tert-butyldimethylsilylbenzene, 2-allyloxy-1-bromo-3-tert-butyldimethylsilyl-5-methylbenzene, 2-allyloxy-1-bromo-3-tert-butyl-5-methoxybenzene, 2-allyloxy-1-bromo-3-tert-butyl-5-chlorobenzene, 2-allyloxy-3,5-diamyl-1-bromobenzene and 1-allyloxy-2-bromonaphthalene.

Examples of the compound [9] further include compounds resulting from changing the "methoxy" or "allyloxy" of the above-mentioned compounds to benzyloxy, ethoxy, tert-butyldimethylsilyloxy, trimethylsilyloxy or methoxymethoxy, and compounds resulting from changing the "bromo" to chloro or iodo.

In the compound [4], the group having a cyclopentadienylidene skeleton represented as the substituent $Cp^3$ may be, for example, the cyclopentadienylidene group, methylcyclopentadienylidene group, dimethylcyclopentadienylidene group, trimethylcyclopentadienylidene group, tetramethylcyclopentadienylidene group, ethylcyclopentadienylidene group, n-propylcyclopentadienylidene group, isopropylcyclopentadienylidene group, n-butylcyclopentadienylidene group, sec-butylcyclopentadienylidene group, tert-butylcyclopentadienylidene group, n-pentylcyclopentadienylidene group, neopentylcyclopentadienylidene group, n-hexylcyclopentadienylidene group, n-octylcyclopentadienylidene group, phenylcyclopentadienylidene group, naphthylcyclopentadienylidene group, trimethylsilylcyclopentadienylidene group, triethylsilylcyclopentadienylidene group, tert-butyldimethylsilylcyclopentadienylidene group, indenylidene group, methylindenylidene group, dimethylindenylidene group, ethylindenylidene group, n-propylindenylidene group, isopropylindenylidene group, n-butylindenylidene group, sec-butylindenylidene group, tert-butylindenylidene group, n-pentylindenylidene group, neopentylindenylidene group, n-hexylindenylidene group, n-octylindenylidene group, n-decylindenylidene group, phenylindenylidene group, methylphenylindenylidene group, naphthylindenylidene group, trimethylsilylindenylidene group, triethylsilylindenylidene group, tert-butyldimethylsilylindenylidene group, tetrahydroindenylidene group, fluorenylidene group, methylfluorenylidene group, dimethylfluorenylidene group, ethylfluorenylidene group, diethylfluorenylidene group, n-propylfluorenylidene group, di-n-propylfluorenylidene group, isopropylfluorenylidene group, diisopropylfluorenylidene group, n-butylfluorenylidene group, sec-butylfluorenylidene group, tert-butylfluorenylidene group, di-n-butylfluorenylidene group, di-sec-butylfluorenylidene group, di-tert-butylfluorenylidene group, n-pentylfluorenylidene group, neopentylfluorenylidene group, n-hexylfluorenylidene group, n-octylfluorenylidene group, n-decylfluorenylidene group, n-dodecylfluorenylidene group, phenylfluorenylidene group, diphenylfluorenylidene group, methylphenylfluorenylidene group, naphthylfluorenylidene group, trimethylsilylfluorenylidene group, bis-trimethylsilylfluorenylidene group, triethylsilylfluorenylidene group and tert-butyldimethylsilylfluorenylidene group, preferred of these being cyclopentadienylidene group, methylcyclopentadienylidene group, tert-butylcyclopentadienylidene group, tetramethylcyclopentadienylidene group, indenylidene group, fluorenylidene group, etc.

Examples of the compound [4] include 5-methylidene-cyclopenta-1,3-diene, 2-tert-butyl-5-methylidene-cyclopenta-1,3-diene, 2-methyl-5-methylidene-cyclopenta-1,3-diene, 2-tert-butyldimethylsilyl-5-methylidene-cyclopenta-1,3-diene, 2-trimethylsilyl-5-methylidene-cyclopenta-1,3-diene, 5-isopropylidene-cyclopenta-1,3-diene, 2-tert-butyl-5-isopropylidene-cyclopenta-1,3-diene, 2-methyl-5-isopropylidene-cyclopenta-1,3-diene, 2-tert-butyldimethylsilyl-5-isopropylidene-cyclopenta-1,3-diene, 2-trimethylsilyl-5-isopropylidene-cyclopenta-1,3-diene, 5-(1-ethylpropylidene)-cyclopenta-1,3-diene, 2-tert-butyl-5-(1-ethylpropylidene)-cyclopenta-1,3-diene, 2-methyl-5-(1-ethylpropylidene)-cyclopenta-1,3-diene, 2-tert-butyldimethylsilyl-5-(1-ethylpropylidene)-cyclopenta-1,3-diene, 2-trimethylsilyl-5-(1-ethylpropylidene)cyclopenta-1,3-diene, 5-diphenylmethylidene-cyclopenta-1,3-diene, 2-tert-butyl-5-diphenylmethylidene-cyclopenta-1,3-diene, 2-methyl-5-diphenylmethylidene-cyclopenta-1,3-diene, 2-tert-butyldimethylsilyl-5-diphenylmethylidene-cyclopenta-1,3-diene and 2-trimethylsilyl-5-diphenylmethylidene-cyclopenta-1,3-diene.

The amount of the compound [4] to be used is in the range of usually 0.5–3 moles, preferably 0.7–1.5 moles per 1 mole of the compound [9].

Examples of the organoalkali metal compound include organolithium compounds, e.g., methyllithium, ethyllithium, n-butyllithium, sec-butyllithium, tert-butyllithium, lithium trimethylsilyl acetylide, lithium acetylide, trimethylsilylmethyllithium, vinyllithium, phenyllithium and allyllithium.

The amount of the organoalkali metal compound or metallic magnesium to be used per mole of the compound [9] is usually in the range of 0.5–5 moles, the amount of the organoalkali metal compound being preferably in the range of 0.9–2.2 moles and that of metallic magnesium being preferably in the range of 0.9–1.2 moles.

The reaction is usually conducted in a solvent inert to the reaction. Examples of the solvent include aprotic solvents, e.g., aromatic hydrocarbon solvents, such as benzene and toluene, aliphatic hydrocarbon solvents, such as hexane and heptane, ether type solvents, such as diethyl ether, tetrahydrofuran and 1,4-dioxane, amide type solvents, such as hexamethylphosphoric amide and dimethylformamide, polar solvents, such as acetonitrile, propionitrile, acetone, diethyl ketone, methyl isobutyl ketone and cyclohexanone, and halogen-containing solvents, such as dichloromethane, dichloroethane, chlorobenzene and dichlorobenzene. These solvents may be used each alone or as a mixture of two or more thereof. The amount of the solvent to be used is in the range of usually 1–200 times by weight, preferably 3–50 times by weight the amount of the compound [9].

The present step may usually be conducted by adding the compound [9] and the organoalkali metal compound or metallic magnesium to the solvent, then adding the compound [4] thereto, and thereafter adding water or an acidic aqueous solution or the like thereto, but it may also be conducted by adding the compound [9], the compound [4] and the organoalkali metal compound or metallic magnesium simultaneously to the solvent and then adding water or an acidic aqueous solution thereto. The reaction temperature is usually in the range from not lower than −100° C. to not higher than the boiling point of the solvent. The temperature is preferably in the range from −80° C. to +40° C. when the organoalkali metal compound is used, and preferably in the range from 10° C. to 100° C. when metallic magnesium is used.

Examples of the acidic aqueous solution include aqueous ammonium chloride solution and hydrochloric acid. The amount of water or acidic aqueous solution used is in the range of usually 1–200 times by weight, preferably 3–50 times by weight the amount of the compound [9] used.

When metallic magnesium is used, the initiation of the reaction can be promoted by using an initiator in combination therewith. Examples of the initiator include molecular halogens, such as bromine and iodine, alkyl halides, such as methyl iodide, ethyl iodide and ethyl bromide, and alkyl dihalides, such as 1,2-dichloroethane and 1,2-dibromoethane. The amount of the initiator to be used per mole of metallic magnesium is usually in the range of 0.00001–0.1 mole.

The reaction mixture obtained is separated into an organic layer and an aqueous layer, the solution of the compound [2a] being obtained as the organic layer. When a solvent compatible with water was used in the above-mentioned reaction, or when the organic layer and the aqueous layer cannot be easily separated from each other owing to the use of an insufficient amount of the solvent in the above-mentioned reaction, the layer separation is advantageously conducted after adding an organic solvent insoluble in water, such as toluene, ethyl acetate and chlorobenzene, to the reaction mixture.

The compound [2a] may be used in the next [step 3] either as the solution thus obtained as it is or after taken out from the solution.

The compound [2a] can be taken out from the solution of the compound [2a], for example, by washing the solution with water, then drying the solution and removing the solvent by distillation. The compound [2a] thus obtained may be further purified by such means as recrystallization, distillation and column chromatography.

When a solid precipitates out after addition of the compound [9] and the organoalkali metal compound or metallic magnesium to the solvent, followed by addition of the compound [4] thereto, or after addition of the compound [9], the compound [4] and the organoalkali metal compound or metallic magnesium to the solvent, the compound [1] can also be prepared by taking out the solid from the reaction system, adding the solid to a solvent which can be used in the step [3], and then adding the compound [3] thereto.

The compound [9] used in the above-mentioned [step 2] can be prepared through the [step 1] as described below.
[Step 1]

The step of preparing the compound [9] by reacting the compound [10] with a halide represented by the formula (11) (hereinafter referred to as compound [11]):

$$R^7Y^5 \tag{11}$$

wherein $Y^5$ is a halogen atom and $R^7$ is the same as defined above, in the presence of a base.

The halogen atoms represented as the substituent $Y^5$ in the compound [11] include the chlorine, bromine and iodine atom.

The compound [11] may be, for example, methyl bromide, ethyl bromide, vinyl bromide, allyl bromide, 2-chloro-2-propenyl bromide, 2-bromo-2-propenyl bromide, 2-methyl-2-propenyl bromide, homoallyl bromide, hexenyl bromide and decenyl bromide, and compounds resulting from changing the "bromide" of the above-mentioned compounds to chloride or iodide. The amount of the compound [11] to be used per mole of the compound [10] is in the range of usually 0.5–5 moles, preferably 0.9–3.3 moles.

The base may be, for example, inorganic bases, such as lithium hydroxide, lithium carbonate, lithium hydrogen carbonate, lithium hydride, lithium methoxide, lithium ethoxide, sodium hydroxide, sodium carbonate, sodium hydrogen carbonate, sodium hydride, sodium methoxide, potassium hydroxide, potassium carbonate, potassium hydrogen carbonate, potassium hydride, potassium methoxide and potassium ethoxide, amine compounds, e.g., primary amine compounds, such as methylamine, ethylamine, n-propylamine, isopropylamine, n-butylamine, tert-butylamine, n-octylamine, n-decylamine, aniline and ethylenediamine, secondary amine compounds, such as dimethylamine, diethylamine, di-n-propylamine, di-n-propylamine, di-n-butylamine, di-tert-butylamine, di-n-octylamine, di-n-decylamine, pyrrolidine, hexamethyldisilazane, and diphenylamine, and tertiary amine compounds, such as trimethylamine, triethylamine, tri-n-propylamine, tri-n- butylamine, diisopropylethylamine, tri-n-octylamine, tri-n-decylamine, triphenylamine, N,N-dimethylaniline, N,N,N',N'-tetramethylethylenediamine, N-methylpyrrolidine, and 4-dimethylaminopyridine, and such organoalkali metal compounds as organolithium compounds, e.g., methyllithium, ethyllithium, n-butyllithium, sec-butyllithium, tert-butyllithium, lithium trimethylsilylacetylide, lithium acetylide, trimethylsilylmethyllithium, vinyllithium, phenyllithium and allyllithium. The amount of the base to be used per mole of the compound [10] is in the range of usually 0.5–3 moles, preferably 0.9–1.5 moles.

A catalyst may be used in the reaction. The catalyst may be, for example, quaternary ammonium salts, e.g., benzyltrimethylammonium chloride, benzyltriethylammonium chloride, benzyltri-n-propylammonium chloride, benzyltri-n-butylammonium chloride, tetramethylammonium chloride, tetraethylammonium chloride, tetra-n-propylammonium chloride, and tetra-n-butylammonium chloride, and compounds resulting from changing the "chloride" of the above-mentioned compounds to bromide or iodide. The amount of the catalyst to be used per mole of the compound [10] is in the range of usually 0.00001–0.5 mole, preferably 0.0001–0.1 mole.

The reaction is usually conducted in a solvent inert to the reaction. Examples of the solvent include aprotic solvents, e.g., aromatic hydrocarbon solvents, such as benzene, toluene and xylene, aliphatic hydrocarbon solvents, such as hexane and heptane, ether type solvents, such as diethyl ether, tetrahydrofuran and 1,4-dioxane, amide type solvents such as hexamethylphosphoric amide and dimethylformamide, polar solvents, such as acetonitrile, propionitrile, acetone, diethyl ketone, methyl isobutyl ketone and cyclohexanone, and halogen-containing solvents, such as dichloromethane, dichloroethane, chlorobenzene and dichlorobenzene, and such protic solvents as alcoholic solvents, such as methanol, ethanol, isopropanol and n-butanol. These solvents may be used each alone or as a mixture of two or more thereof. The amount of the solvent to be used is in the range of usually 1–200 times by weight, preferably 5–30 times by weight the amount of the compound [10].

The present step can be conducted, for example, by adding the base to the solvent, then adding the compound [10] thereto and thereafter adding the compound [11] thereto. When the catalyst is used, the reaction is conducted by adding the base and the catalyst to the solvent, then adding the compound [10] thereto and thereafter adding the compound [11] thereto. The reaction temperature is in the range of usually from not lower than −100° C. to not higher than the boiling point of the solvent, preferably 0–100° C.

The reaction mixture obtained is mixed with water and then separated into an organic layer and an aqueous layer, the solution of the compound [9] being obtained as the organic layer. When a solvent compatible with water was used in the aforesaid reaction or when the organic layer and aqueous layer cannot be easily separated from each other owing to the use of an insufficient amount of the solvent in the aforesaid reaction, the layer separation is advantageously conducted after adding an organic solvent insoluble in water, such as toluene, ethyl acetate and chlorobenzene, to the reaction mixture.

Though the compound [9] may be used in the next step as the solution thus obtained as it is, the compound is usually employed after taken out from the solution.

The compound [9] can be taken out from the solution thereof, for example, by washing the solution with water, then drying the solution, and removing the solvent by distillation. The compound [9] thus obtained may be further purified by such means as recrystallization, distillation and column chromatography.

The compound [2b] can be prepared through the [step 5] as described below.

[Step 5]

The step of preparing the compound [2b] by reacting a halide compound represented by the formula (5) (hereinafter referred to as compound [5]):

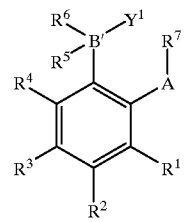

(5)

wherein $Y^1$ is a halogen atom, and A, B', $R^1$, $R^2$, $R^3$, $R^4$, $R^5$, $R^6$ and $R^7$ are respectively the same as defined above, with a cyclopentadienyl metal salt represented by the formula (6) (hereinafter referred to as compound [6]):

$$M^2Cp^2 \qquad (6)$$

wherein $M^2$ is an alkali metal atom and $Cp^2$ is the same as defined above.

The halogen atom represented as the substituent $Y^1$ in the compound [5] is, for example, the chlorine, bromine or iodine atom.

Examples of the compound [5] include chloro(2-methoxyphenyl)dimethylsilane, chloro(2-methoxy-3-methylphenyl)dimethylsilane, chloro(2-methoxy-3,5-dimethylphenyl)dimethylsilane, (3-tert-butyl-2-methoxyphenyl)chlorodimethylsilane, (3-tert-butyl-2-methoxy-5-methylphenyl)chlorodimethylsilane, (3,5-di-tert-butyl-2-methoxyphenyl)chlorodimethylsilane, chloro(2-methoxy-3-phenylphenyl)dimethylsilane, chloro(2-methoxy-5-methyl-3-phenylphenyl)dimethylsilane, (3-tert-butyldimethylsilyl-2-methoxyphenyl)chlorodimethylsilane, (3-tert-butyldimethylsilyl-2-methoxy-5-methylphenyl)chlorodimethylsilane, chloro(2-methoxy-3-trimethylsilylphenyl)dimethylsilane, chloro(2-methoxy-5-methyl-3-trimethylsilylphenyl)dimethylsilane, (3,5-diamyl-2-methoxyphenyl)chlorodimethylsilane, (3-tert-butyl-2,5-dimethoxyphenyl)chlorodimethylsilane, (3-tert-butyl-5-chloro-2-methoxyphenyl)chlorodimethylsilane, (2-allyloxy-phenyl)chlorodimethylsilane, (2-allyloxy-3-methylphenyl)chlorodimethylsilane, (2-allyloxy-3,5-dimethylphenyl)chlorodimethylsilane, (2-allyloxy-3-tert-butylphenyl)chlorodimethylsilane, (2-allyloxy-3-tert-butyl-5-methylphenyl)chlorodimethylsilane, (2-allyloxy-3,5-di-tert-butylphenyl)chlorodimethylsilane, (2-allyloxy-3-phenylphenyl)chlorodimethylsilane, (2-allyloxy-5-methyl-3-phenylphenyl)chlorodimethylsilane, (2-allyloxy-3-tert-butyldimethylsilylphenol)chlorodimethylsilane, (2-allyloxy-3-tert-butyldimethylsilyl-4-methylphenyl)chlorodimethylsilane, (2-allyloxy-3-trimethylsilylphenyl)chlorodimethylsilane, (2-allyloxy-5-methyl-3-trimethylsilylphenyl)chlorodimethylsilane, (2-allyloxy-3,5-diamylphenyl)chlorodimethylsilane, (2-allyloxy-3-tert-butyl-5-methoxyphenyl)chlorodimethylsilane, (2-allyloxy-3-tert-butyl-5-chlorophenyl)chlorodimethylsilane and (1-allyloxynaphthalen-2-yl)chlorodimethylsilane.

Examples of the compound [5] further include compounds resulting from changing the "methoxy" or "allyloxy" of the above-mentioned compounds to benzyloxy, ethoxy, trimethylsilyloxy, tert-butyldimethylsilyloxy or methoxymethoxy, and compounds resulting from changing the "chlorodimethylsilane" to chlorodiethylsilane, chlorodiphenylsilane, chlorodimethoxysilane, bromodimethylsilane or dimethyliodosilane.

The alkali metal represented as the substituent $M^2$ in the compound [6] is, for example, lithium, potassium and sodium.

Examples of the compound [6] include cyclopentadienyllithium, methylcyclopentadienyllithium, dimethylcyclopentadienyllithium, trimethylcyclopentadienyllithium, tetramethylcyclopentadienyllithium, ethylcyclopentadienyllithium, n-propylcyclopentadienyllithium, isopropylcyclopentadienyllithium, tert-butylcyclopentadienyllithium, n-butylcyclopentadienyllithium, sec-butylcyclopentadienyllithium, isobutylcyclopentadienyllithium, di-tert-butylcyclopentadienyllithium, n-hexylcyclopentadienyllithium, phenylcyclopentadienyllithium, trimethylsilylcyclopentadienyllithium, tert-butyldimethylsilylcyclopentadienyllithium, indenyllithium, methylindenyllithium, pehnylindenyllithium, fluorenyllithium, cyclopentadienylsodium, methylcyclopentadienylsodium, tetramethylcyclopentadienylsodium, tert-butylcyclopentadienylsodium, n-butylcyclopentadienylsodium, trimethylsilylcyclopentadienylsodium, tert-butyldimethylsilylcyclopentadienylsodium, indenylsodium, fluorenylsodium, cyclopentadienylpotassium, methylcyclopentadienylpotassium, tetramethylcyclopentadienylpotassium, tert-butylcyclopentadienylpotassium, n-butylcyclopentadienylpotassium, trimethylsilylcyclopentadienylpotassium, tert-butyldimethylsilylcyclopentadienylpotassium, indenylpotassium and fluorenylpotassium.

The amount of the compound [6] to be used per mole of the compound [5] is in the range of usually 0.5–3 moles, preferably 0.9–1.1 moles.

The reaction is usually conducted in a solvent inert to the reaction. Examples of the solvent include aprotic solvents, e.g., aromatic hydrocarbon solvents, such as benzene, toluene and xylene, aliphatic hydrocarbon solvents, such as hexane and heptane, ether type solvents, such as diethyl ether, tetrahydrofuran and 1,4-dioxane, amide type solvents, such as hexamethylphosphoric amide and dimethylformamide, and halogen-containing solvent, such as dichloromethane, dichloroethane, chlorobenzene and dichlorobenzene. These solvents may be used each alone or as a mixture of two or more thereof. The amount of the solvent to be used is in the range of usually 1–200 times by weight, preferably 5–30 times by weight the amount of the compound [5].

The present step can be conducted, for example, by mixing the compound [5] and the compound [6] in the solvent. The reaction temperature is in the range of usually from not lower than –100° C. to not higher than the boiling point of the solvent, preferably from –80° C. to +35° C.

The reaction mixture obtained is mixed with water or an acidic aqueous solution, such as aqueous ammonium chloride solution or hydrochloric acid, and then separated into an organic layer and an aqueous layer, the solution of the compound [2b] being obtained as the organic layer. When a solvent compatible with water was used in the aforesaid reaction or when the organic layer and the aqueous layer cannot be easily separated from each other owing to the use of an insufficient amount of the solvent in the aforesaid reaction, the layer separation is advantageously conducted after adding an organic solvent insoluble in water, such as toluene, ethyl acetate and chlorobenzene, to the reaction mixture.

The compound [2b] may be used in the next [step 3] as the solution thus obtained as it is or it may be used after taken out from the solution.

The compound [2b] can be taken out from the solution thereof, for example, by washing the solution with water, then drying the solution and removing the solvent by distillation. The compound [2b] thus obtained may be further purified by such means as recrystallization, distillation and column chromatography.

The compound [5] used in the above-mentioned [step 5] can be prepared through the [step 4] as described below.

[Step 4]

The step of preparing the compound [5] by reacting the compound [9] with a dihalide compound represented by the formula (7) (hereinafter referred to as compound [7]):

(7)

wherein $Y^2$ is a halogen atom, and B', $R^5$, $R^6$ and $Y^1$ are respectively the same as defined above, in the presence of an organoalkali metal compound or metallic magnesium.

The compound [9] can be prepared through the [step 1] as described above. In this instance, the compound [9] obtained may be used as the solution obtained as an organic layer by layer separation as it is, or it may be used after taken out from the solution.

The halogen atom represented as the substituent $Y^2$ in the compound [7] is, for example, the chlorine, bromine or iodine atom.

Examples of the compound [7] include dichlorodimethylsilane, dichlorodiphenylsilane, dichlorodiethylsilane, dichloro-di-n-propylsilane, dichlorodimethoxysilane, diallyldichlorosilane, dichlorodivinylsilane, dichloromethylvinylsilane, dichlorodibenzylsilane, dichlorochloromethylmethylsilane, dibromodimethylsilane and diiododimethylsilane.

The amount of the compound [7] to be used per mole of the compound [9] is in the range of usually 0.5–50 moles, preferably 0.9–5 moles.

Examples of the organoalkali metal compounds include organolithium compounds, for example, organolithium compounds, such as methyllithium, ethyllithium, n-butyllithium, sec-butyllithium, tert-butyllithium, lithium trimethylsilyl acetylide, lithium acetylide, trimethylsilylmethyllithium, vinyllithium, phenyllithium and allyllithium.

The amount of the organoalkali metal compound or metallic magnesium to be used per mole of the compound [9] is in the range of usually 0.5–5 moles, preferably 0.9–2.2 moles.

The reaction is usually conducted in a solvent inert to the reaction. Examples of the solvent include aprotic solvents, e.g., aromatic hydrocarbon solvents, such as benzene, toluene and xylene, aliphatic hydrocarbon solvents, such as hexane and heptane, ether type solvents, such as diethyl ether, tetrahydrofuran and 1,4-dioxane, amide type solvents, such as hexamethylphosphoric amide and dimethylformamide, polar solvents, such as acetonitrile, propionitrile, acetone, diethyl ketone, methyl isobutyl ketone and cyclohexanone, and halogen-containing solvents, such as dichloromethane, dichloroethane, chlorobenzene and dichlorobenzene. These solvents may be used each alone or as a mixture of two or more thereof. The amount of the solvent to be used is in the range of usually 1–200 times by weight, preferably 5–30 times by weight the amount of the compound [9].

The present step may be conducted, for example, by adding the compound [9] and the organoalkali metal compound or metallic magnesium to the solvent, and then adding the compound [7] thereto, or it may also be conducted by adding the compound [9], the compound [7] and the organoalkali metal compound or metallic magnesium simultaneously to the solvent. The reaction temperature is not lower than −100° C. and not higher than the boiling point of the solvent. The temperature is preferably in the range from −80° C. to +40° C. when the organoalkali metal compound is used and preferably in the range from 10° C. to 100° C. when metallic magnesium is used.

When metallic magnesium is used, the initiation of the reaction can be promoted by using an initiator in combination therewith. Examples of the initiator include molecular halogens, such as bromine and iodine, alkyl halides, such as methyl iodide, ethyl iodide and ethyl bromide and alkyl dihalides, such as 1,2-dichloroethane and 1,2-dibromoethane. The amount of the initiator to be used per mole of metallic magnesium is usually in the range of 0.00001–0.1 mole.

The compound [5] thus obtained may be used in the next [step 5] either as the reaction mixture obtained as it is, or as the residue obtained by concentrating the reaction mixture, or after taken out from the reaction mixture.

The compound [5] can be taken out from the reaction mixture, for example, by concentrating the reaction mixture to obtain a residue, dissolving the residue in a hydrophobic solvent, e.g., an aromatic hydrocarbon solvent, such as toluene, or an aliphatic hydrocarbon solvent, such as hexane or heptane, filtering off the insolubles, and then removing the solvent by distillation. The compound [5] thus obtained may be further purified by such means as recrystallization, distillation and column chromatography.

The compound [2b] can also be prepared through the [step 6] as described below.

[Step 6]

The step of preparing the compound [2b] by reacting the compound [9] with a halide compound represented by the formula (8) (hereinafter referred to as compound [8]):

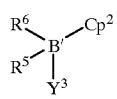

(8)

wherein $Y^3$ is a halogen atom, and B', $Cp^2$, $R^5$ and $R^6$ are respectively the same as defined above, in the presence of an organoalkali metal compound or metallic magnesium.

The compound [9] can be prepared through the [step 1] as mentioned above. In this instance, the resulting compound [9] may be used as it is the solution obtained as an organic layer by layer separation, or it may be used after taken out from the solution.

The halogen atom represented as the substituent $Y^3$ in the compound [8] is, for example, the chlorine, bromine or iodine atom.

Examples of the compound [8] include chloro(cyclopentadienyl)dimethylsilane, chlorodimethyl(methylcyclopentadienyl)silane, chlorodimethyl(tetramethylcyclopentadienyl)silane, chlorodimethyl(tetramethylcyclopentadienyl)silane, chloro(tert-butylcyclopentadienyl)dimethylsilane, chlorodimethyl(trimethylsilylcyclopentadienyl)silane, (inden-1-yl)chlorodimethylsilane, (inden-2-yl)chlorodimethylsilane and chloro(9H-fluoren-9-yl)dimethylsilane, and further, compounds resulting from changing the "cyclopentadienyl" of the above-mentioned compounds to dimethylcyclopentadienyl, n-butylcyclopentadienyl, sec-butylcyclopentadienyl, tert-butyldimethylsilylcyclopentadienyl, trimethylcyclopentadienyl, ethylcyclopentadienyl, n-propylcyclopentadienyl, isopropylcyclopentadienyl, isobutylcyclopentadienyl, phenylcyclopentadienyl, methylinden-1-yl or methylinden-2-yl, compounds resulting from changing the "dimethyl" to diethyl, diphenyl or dimethoxy, and compounds resulting from changing the "chloro" to bromo or iodo.

The amount of the compound [8] to be used per mole of the compound [9] is in the range of usually 0.5–3 moles, preferably 0.9–1.2 moles.

Examples of the organoalkali metal compound include organolithium compounds, such as methyllithium, ethyllithium, n-butyllithium, sec-butyllithium, tert-butyllithium, lithium trimethylsilyl acetylide, lithium acetylide, trimethylsilylmethyllithium, vinyllithium, phenyllithium and allyllithium.

The amount of the organoalkali metal salt or metallic magnesium to be used per mole of the compound [9] is usually 0.5–5 moles, the amount of the organoalkali metal compound being preferably in the range of 0.9–2.2 moles and that of metallic magnesium being preferably in the range of 0.9–1.2 moles.

The reaction is usually conducted in a solvent inert to the reaction. Examples of the solvent include aprotic solvents, e.g., aromatic hydrocarbon solvents, such as benzene, toluene and xylene, aliphatic hydrocarbon solvents, such as hexane and heptane, ether type solvents, such as diethyl ether, tetrahydrofuran and 1,4-dioxane, amide type solvents, such as hexamethylphosphoric amide and dimethylformamide, polar solvents, such as acetonitrile, propionitrile, acetone, diethyl ketone, methyl isobutyl ketone and cyclohexanone, and halogen-containing solvents, such as dichloromethane, dichloroethane, chlorobenzene and dichlorobenzene. These solvents may be used each alone or as a mixture of two or more thereof. The amount of the solvent to be used is in the range of usually 1–200 times by weight, preferably 5–30 times by weight the amount of the compound [9].

The present step can be conducted, for example, by adding the compound [9] and the organoalkali metal salt or metallic magnesium to the solvent and then adding the compound [8] thereto or alternatively by adding the compound [9], the compound [8] and the organoalkali metal salt or metallic magnesium simultaneously to the solvent. The reaction temperature is usually not lower than −100° C. and not higher than the boiling point of the solvent, the temperature being preferably in the range from −78° C. to +40° C. when the organoalkali metal compound is used and preferably in the range from 10° C. to 100° C. when metallic magnesium is used.

When metallic magnesium is used, the initiation of the reaction can be promoted by using an initiator in combination therewith. Examples of the initiator include molecular halogens, such as bromine and iodine, alkyl halides, such as methyl iodide, ethyl iodide and ethyl bromide, and alkyl dihalides, such as 1,2-dichloroethane and 1,2-dibromoethane. The amount of the initiator to be used per mole of metallic magnesium is usually in the range of 0.00001–0.1 mole.

The reaction mixture obtained is mixed with water or an acidic aqueous solution, such as aqueous ammonium chloride solution or hydrochloric acid, and then separated into an organic layer and an aqueous layer, the solution of the compound [2b] being obtained as the organic layer. When a solvent compatible with water was used in the aforesaid reaction or when the organic layer and the aqueous layer cannot be easily separated from each other owing to the use of an insufficient amount of solvent in the aforesaid reaction, the layer separation is advantageously conducted after adding an organic solvent insoluble in water, such as toluene, ethyl acetate and chlorobenzene, to the reaction mixture.

The compound [2b] may be used in the next [step 3] either as the solution thus obtained as it is or after taken out from the solution.

The compound [2b] can be taken out from the solution thereof, for example, by washing the solution with water, then drying the solution, and removing the solvent by distillation. The compound [2b] thus obtained may be further purified by such means as recrystallization, distillation and column chromatography.

[Organoaluminum Compound (A)]

The compound (A) used in the present invention may be known organoaluminum compounds. Preferred examples thereof include any one compound selected from (A1) an organoaluminum compound represented by the formula $E^1{}_aAlZ_{3-a}$, (A2) a cyclic aluminoxane having the structure represented by the formula $\{-Al(E^2)-O-\}_b$, and (A3) a linear aluminoxane having the structure represented by the formula $E^3\{-Al(E^3)-O-\}_cAlE^3{}_2$ (wherein $E^1$, $E^2$ and $E^3$ are each a hydrocarbon group with the number of carbon atoms of 1–8 and all $E^1$, all $E^2$ and all $E^3$ may be the same with or different from each other; Z is a hydrogen atom or a halogen atom and all Z may be the same with or different from each other; a is the number specified by 0<a≦3, b is an integer of 2 or greater, and c is an integer of 1 or greater, and mixtures of two or three kinds thereof.

Specific examples of the organoaluminum compound (A1) represented by the formula $E^1{}_aAlZ_{3-a}$ include trialkylaluminums, such as trimethylaluminum, triethylaluminum, tripropylaluminum, triisobutylaluminum, and trihexylaluminum; dialkylaluminum chlorides, such as dimethylaluminum chloride, diethylaluminum chloride, dipropylaluminum chloride, diisobutylaluminum chloride, and dihexylaluminum chloride; alkylaluminum dichlorides such as methylaluminum dichloride, ethylaluminum dichloride, propylaluminum dichloride, isobutylaluminum dichloride, and hexylaluminum dichloride; and dialkylaluminum hydrides, such as dimethylaluminum hydride, diethylaluminum hydride, dipropylaluminum hydride, diisobutylaluminum hydride and dihexylaluminum hydride. Preferred of these is a trialkylaluminum, more preferred being triethylaluminum and triisobutylaluminum.

Specific examples of $E^2$ and $E^3$ in the cyclic aluminoxane (A2) having the structure represented by the formula $\{-Al(E^2)-O-\}_b$ and in the linear aluminoxane (A3) having the structure represented by the formula $E^3\{-Al(E^3)-O-\}_cAlE^3{}_2$ include alkyl groups, such as the methyl group, ethyl group, normal propyl group, isopropyl group, normal butyl group, isobutyl group, normal pentyl group and neopentyl group; b is an integer of 2 or greater and c is an integer of 1 or greater. Preferably $E^2$ and $E^3$ are methyl group and isobutyl group, b is 2–40 and c is 1–40.

The above-mentioned aluminoxanes can be prepared by various methods. These is no particular limitation as to the method and known methods may be used for preparation. For example, the aluminoxane is prepared by dissolving a trialkylaluminum (e.g., trimethylaluminum) in a suitable organic solvent (e.g., benzene, or aliphatic hydrocarbon) and then contacting the resulting solution with water; or it may be prepared by contacting a trialkylaluminum (e.g., trimethylaluminum) with a metal salt containing water of crystallization (e.g., copper sulfate hydrate).

[Compound (B)]

In the present invention, any one compound selected from (B1) a boron compound represented by the formula $BQ^1Q^2Q^3$, (B2) a boron compound represented by the formula $Z^+(BQ^1Q^2Q^3Q^4)^-$ and (B3) a boron compound represented by the formula $(L-H)^+(BQ^1Q^2Q^3Q^4)^-$ is used as the compound (B).

In the boron compound (B1) represented by the formula $BQ^1Q^2Q^3$, B is a boron atom in the trivalent valence state, $Q_1-Q_3$ are each a halogen atom, hydrocarbon group containing 1–20 carbon atoms, halogenated hydrocarbon group containing 1–20 carbon atoms, substituted silyl group containing 1–20 carbon atoms, alkoxy group containing 1–20 carbon atoms or di-substituted amino group containing 2–20 carbon atoms, which may be the same with or different from each other. Preferred $Q_1-Q_3$ each independently a halogen atom, hydrocarbon group containing 1–20 carbon atoms and halogenated hydrocarbon group containing 1–20 carbon atoms.

Specific examples of the Lewis acid (B1) include tris (pentafluorophenyl)borane, tris(2,3,5,6-tetrafluorophenyl) borane, tris(2,3,4,5-tetrafluorophenyl)borane, tris(3,4,5-trifluorophenyl)borane, tris(2,3,4-trifluorophenyl)borane and phenylbis(pentafluorophenyl)borane, most preferred of these being tris(pentafluorophenyl)borane.

In the boron compound (B2) represented by the formula $Z^+(BQ^1Q^2Q^3Q^4)^-$, $Z^+$ is an inorganic or organic cation, B is a boron atom in the trivalent valence state, and $Q^1-Q^4$ are the same as defined for $Q^1-Q^3$ in the above-mentioned compound (B1).

As to specific examples of the compound represented by the formula $Z^+(BQ^1Q^2Q^3Q^4)^-$, $Z^+$ of the inorganic cation is, for example, a ferrocenium cation, alkyl-substituted ferrocenium cation and silver cation, and $Z^+$ of the organic cation is, for example, a triphenylmethyl cation; $(BQ^1Q^2Q^3Q^4)^-$ is, for example, tetrakis(pentafluorophenyl)borate, tetrakis(2,3, 5,6-tetrafluorophenyl)borate, tetrakis(2,3,4,5-tetrafluorophenyl)borate, tetrakis(3,4,5-trifluorophenyl) borate, tetrakis(2,2,4-trifluorophenyl)borate, phenylbis (pentafluorophenyl)borate and tetrakis(3,5-bistrifluoromethylphenyl)borate.

Examples of the specific combination of these include ferrocenium tetrakis(pentafluorophenyl)borate, 1,1'-dimethylferrocenium tetrakis(pentafluorophenyl)borate, silver tetrakis(pentafluorophenyl)borate, triphenylmethyl tetrakis(pentafluorophenyl)borate and triphenylmethyl tetrakis(3,5-bistrifluoromethylphenyl)borate, most preferred of these being triphenylmethyl tetrakis(pentafluorophenyl) borate.

In the boron compound (B3) represented by the formula (L—H)$^+$(BQ$^1$Q$^2$Q$^3$Q$^4$)$^-$, L is a neutral Lewis base, (L—H)$^-$ is a Brønsted acid, B is a boron atom in the trivalent valence state, and Q$_1$–Q$_4$ are the same as defined for Q$^1$–Q$^3$ in the above-mentioned compound (B1).

In the specific example of the compound represented by the formula (L—H)$^+$(BQ$^1$Q$^2$Q$^3$Q$^4$)$^-$, (L—H)$^+$ of the Brønsted acid is, for example, a trialkyl-substituted ammonium, N,N-dialkylanilinium, dialkylammonium and triarylphosphonium, and the (BQ$^1$Q$^2$Q$^3$Q$^4$)$^-$ may be, for example, the same as those described above.

Examples of the specific combination of these include triethylammonium tetrakis(pentafluorophenyl)borate, tripropylammonium tetrakis(pentafluorophenyl)borate, tri(normal butyl)ammonium tetrakis(pentafluorophenyl)borate, tri(normal butyl)ammonium tetrakis(3,5-bistrifluoromethylphenyl)borate, N,N-dimethylanilinium tetrakis(pentafluorophenyl)borate, N,N-diethylanilinium tetrakis(pentafluorophenyl)borate, N,N-2,4,6-pentamethylanilinium tetrakis(pentafluorophenyl)borate, N,N-dimethylanilinium tetrakis(3,5-bistrifluoromethylphenyl)borate, diisopropylammonium tetrakis(pentafluorophenyl)borate, dicyclohexylammonium tetrakis(pentafluorophenyl)borate, triphenylphosphonium tetrakis(pentafluorophenyl)borate, tri(methylphenyl) phosphonium tetrakis(pentafluorophenyl)borate, and tri (dimethylphenyl)phosphonium tetrakis(pentafluorophenyl) borate, most preferred of these being tri(normal butyl) ammonium tetrakis(pentafluorophenyl)borate or N,N-dimethylanilinium tetrakis(pentafluorophenyl)borate.

In the present invention, the transition metal complex represented by the formula (1), the compound (A), or further the compound (B) may be charged in any desired order at the time of polymerization. Alternatively, any desired combination of these compounds may be contacted with each other beforehand and the resulting product may be used at the time of polymerization.

As to the amounts of the respective components of the catalyst, the respective components are desirably used such that the molar ratio of the compound (A) to the transition metal complex may fall within the range of 0.1–10,000, preferably 5–2,000 and the molar ratio of the compound (B) to the transition metal complex may fall within the range of 0.01–100, preferably 0.5–10. With regard to the concentrations of the respective catalyst components when they are used in the form of a solution, the respective components are desirably used such that the concentration of the transition metal complex represented by the formula (1) may fall within the range of 0.0001–5 mmol/l, preferably 0.001–1 mmol/l, the concentration of the compound (A) in terms of Al atom within the range of 0.01–500 mmol/l, preferably 0.1–100 mmol/l and the concentration of the compound (B) within the range of 0.0001–5 mmol/l, preferably 0.001–1 mmol/l.

In the present invention, the monomer used for polymerization may be any of the olefins and diolefins each with the number of carbon atoms of 2–20. Two or more kinds of the monomers may also be used simultaneously. Some examples of the monomer are shown below, but the invention is not limited to these compounds. Specific examples of the olefin include ethylene, propylene, butene-1, pentene-1, hexene-1, heptene-1, octene-1, nonene-1, decene-1, 5-methyl-2-pentene-1 and vinylcyclohexane. The diolefin compounds are, for example, conjugated diene or non-conjugated diene hydrocarbon compounds. Specific examples of the non-conjugated diene compound include 1,5-hexadiene, 1,4-hexadiene, 1,4-pentadiene, 1,7-octadiene, 1,8-nonadiene, 1,9-decadiene, 4-methyl-1,4-hexadiene, 5-methyl-1,4-hexadiene, 7-methyl-1,6-octadiene, 5-ethylidene-2-norbornene, dicyclopentadiene, 5-vinyl-2-norbornen, 5-methyl-2-norbornene, norbornadiene, 5-methylene-2-norbornene, 1,5-cyclooctadiene and 5,8-endomethylene-hexahydronaphthalene. Specific examples of the conjugated diene compound include 1,3-butadiene, isoprene, 1,3-hexadiene, 1,3-octadiene, 1,3-cyclooctadiene and 1,3-cyclohexadiene.

Specific examples of the monomers which constitute copolymers include the combinations of ethylene and propylene, ethylene and butene-1, ethylene and hexene-1, and propylene and butene-1, and combinations wherein 5-ethylidene-2-norbornene is used in addition to the above-mentioned combination, but the invention is not limited thereto.

In the present invention, aromatic vinyl compounds may also be used as the monomer. Specific examples of the aromatic vinyl compound include styrene, o-methylstyrene, m-methylstyrene, p-methylstyrene, o,p-dimethylstyrene, o-ethylstyrene, m-ethylstyrene, p-ethylstyrene, o-chlorostyrene, p-chlorostyrene, α-methylstyrene and divinylbenzene.

The method of polymerization is not particularly limited. There may be used, for example, solution polymerization or slurry polymerization wherein aliphatic hydrocarbons, such as butane, pentane, hexane, heptane and octane, aromatic hydrocarbons, such as benzene and toluene, or halogenated hydrocarbons, such as methylene dichloride, are used as the solvent, and gas phase polymerization conducted in gaseous monomers. Further, polymerization may be conducted either continuously or batch-wise.

The polymerization temperature may be in the range from −50° C. to +200° C., but it is particularly preferably in the range from −20° C. to +100° C. The polymerization pressure is preferably from normal pressure to 60 kg/cm$^2$ G. The polymerization time, in general, is determined according to the kind of the intended polymer and the reaction apparatus, and may be in the range from 1 minute to 20 hours. In the present invention, chain transfer agents, such as hydrogen, may be added to control the molecular weight of the copolymer.

BEST MODE FOR CARRYING OUT THE INVENTION

Figure 1:
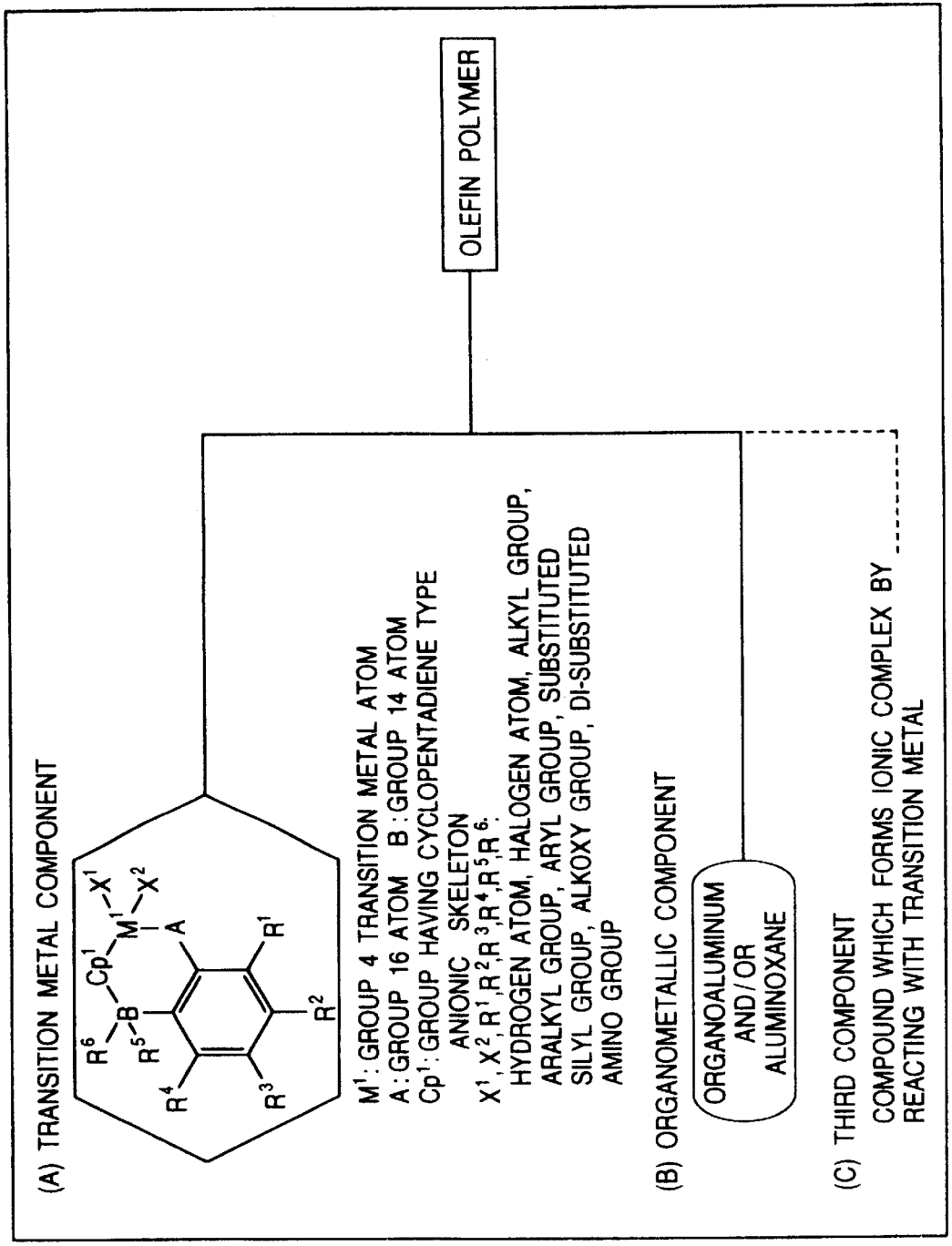
FIG. 1 is a flow chart for facilitating the understanding of the present invention. The flow chart merely shows a representative example of one aspect of the present invention, and in no way limits the present invention.

The present invention is described below in detail with reference to Examples and Comparative Examples, but the invention is not limited thereto.

The properties of polymers shown in Examples were determined by the following methods.

(1) Intrinsic viscosity [η$_1$]: A 100 mg sample of the copolymer obtained was dissolved in 50 ml of tetralin at 135° C. The intrinsic viscosity [η$_1$] was determined from the falling velocity of the tetralin solution containing the sample dissolved therein by using an Ubbelohde viscometer set in a water both kept at 135° C.

(2) Intrinsic viscosity [η$_2$]: A 300 mg sample of the copolymer obtained was dissolved in 100 ml of xylene to give a concentration of about 3 mg/ml. Then the solution was diluted with xylene in dilutions of 1/2, 1/3 and 1/5 to obtain samples of 3 levels of concentration. The intrinsic viscosity [$\eta_2$] was determined from the falling velocity of the xylene solution containing the sample dissolved therein by using an Ubbelohde viscometer set in an oil bath at 70° C.

(3) α-Olefin content in copolymer: The α-olefin content in the obtained polymer was determined from the infrared absorption spectra. Determination and calculation were made according to methods described in literature (Takayama, Usami, et al., Characterization of Polyethylene by Infrared Absorption Spectra, or McRae, M. A. and Madams W. F., Die Makromoleculare Chemie, 177, 461 (1976)) by making use of characteristic absorptions originating from α-olefin, e.g., 1375 cm$^{-1}$ (propylene) and 772 cm$^{-1}$.

Short chain branching (SCB) was expressed in terms of the number of short chain branching per 1,000 carbon atoms.

(4) Diolefin content in copolymer: When diolefin units are present in the copolymer, the diolefin content was determined from the infrared absorption spectra in the same manner as (3) above making use of characteristic peaks originating from the diolefin used. For example, when 5-ethylidene-2-norbornene (ENB) was used, the determination was made by using the peak at 1688 cm$^{-1}$ (the peak originating from double bond of ENB).

(5) Melting point of copolymer: The melting point was determined by using Seiko-SSC-5200 under the following conditions.

Temperature increase: from 40° C. to 150° C. (10° C./min), kept for 5 minutes

Cooling: from 150° C. to 10° C. (5° C./min.), kept for 10 minutes

Determination: from 10° C. to 160° C. (5° C./min)

(6) Molecular weight and molecular weight distribution:

These were determined by using a gel permeation chromatography apparatus (mfd. by Waters Corp., 150, C) under the following conditions:

Column: TSK gel GMH-HT
Measuring temperature: set at 145° C.
Measuring concentration: 10 mg/10 ml o-dichlorobenzene (7) Structures of ligand and complex These were confirmed by $^1$H-NMR measurement (apparatus: AM400, mfd. by Bruker Corp.)

EXAMPLE 1

(1) Synthesis of Transition Metal Complex (1-1) Synthesis of 1-bromo-3-tert-butyl-5-methyl-2-phenol In a 4-necked 500-ml flask fitted with a stirrer, under nitrogen atmosphere, 20.1 g (123 mmol) of 2-tert-butyl-5-methyl-2-phenol was dissolved in 150 ml of toluene, and succeedingly 25.9 ml (18.0 g, 246 mmol) of tert-butylamine was added thereto. The resulting solution was cooled to –70° C., and 10.5 ml (32.6 g, 204 mmol) of bromine was slowly added to the solution by means of a syringe. The resulting solution was kept at –70° C. and stirred for 2 hours. Thereafter the solution was brought up to room temperature and washed three times, 100 ml of 10% dilute hydrochloric acid being added for each time of washing. The organic layer obtained after washing was dried with anhydrous sodium sulfate. Then, the solvent was removed from the solution by using an evaporator to leave an orange oil. The orange oil was purified by applying the oil to a silica gel column (Wako Gel C100), followed by developing with hexane, and removing the solvent from the obtained fraction. Thus, 18.4 g (75.7 mmol) of a purified colorless oil was obtained. The $^1$H-NMR (CD$_2$Cl$_2$ solvent) data of the purified oil are shown below.

δ1.32 (s, 9H), 2.19 (s, 3H), 6.98 (s, 1H), 7.11 (s, 1H)

From the $^1$H-NMR data, the colorless oil was identified as 1-bromo-3-tert-butyl-5-methyl-2-phenol. The yield was 62%.

(1-2) Synthesis of 1-bromo-3-tert-butyl-2-methoxy-5-methylbenzene

In a 100-ml 4-necked flask fitted with a stirrer, under nitrogen atmosphere, 13.9 g (57.2 mmol) of 1-bromo-3-tert-butyl-5-methyl-2-phenol synthesized in (1-1) above was dissolved in 40 ml of acetonitrile, and succeedingly 3.8 g (67.9 mmol) of potassium hydroxide was added thereto. To the resulting mixture was further added slowly 17.8 ml (40.6 g, 286 mol) of methyl iodide by means of a syringe, and the reaction mixture was stirred for 12 hours. Thereafter, the solvent was removed with an evaporator to leave a residue. Then 40 ml of hexane was added to the residue to extract hexane solubles. The extraction was repeated three times. The solvent was removed from the extracts to obtain 13.8 g (53.7 mmol) of a pale yellow oil. The $^1$H-NMR (CD$_2$Cl$_2$ solvent) data of the oil are shown below.

δ1.31 (s, 9H), 2.20 (s, 3H), 3.81 (s, 3H), 7.02 (s, 1H), 7.18 (s, 1H)

From the $^1$H-NMR data, the pale yellow oil obtained was identified as 1-bromo-3-tert-butyl-2-methoxy-5-methylbenzene. The yield was 94%.

(1-3) Synthesis of 2-cyclopentadienyl-2-(3-tert-butyl-2-methoxy-5-methylphenyl)propane In a 100-ml 4-necked flask fitted with a stirrer, under nitrogen atmosphere, 4.61 g (17.9 mmol) of 1-bromo-3-tert-butyl-2-methoxy-5-methylbenzene synthesized in (1-2) above was dissolved in 10 ml of dry diethyl ether and the solution was cooled to –70° C. To the solution was slowly added 18.0 mol of n-BuLi (11.1 ml of a n-BuLi solution in hexane of a concentration of 1.62 mol/l) and stirred at –70° C. for 2 hours. To the resulting reaction liquid was further added a solution obtained by dissolving 1.91 g (18.0 mmol) of 6,6-dimethylfulvene in 10 ml of diethyl ether, and then the resulting mixture was slowly brought up to room temperature. Succeedingly, 25 ml of 5 wt % dilute hydrochloric acid was added to the mixture. Then 30 ml of hexane was added to the resulting reaction liquid to extract hexane solubles. The extraction was repeated 3 times. The extract was dried with anhydrous sodium sulfate and the solvent was removed with an evaporator to leave a yellow oil. The yellow oil was purified by applying the oil to a silica gel column (Wako Gel C-100), followed by developing with hexane, and removing the solvent from the fraction obtained. Thus, 3.0 g of purified pale yellow oil was obtained. The $^1$H-NMR (CD$_2$Cl$_2$ solvent) data of the oil are shown below.

δ1.48 (s, 9H), 1.71 (s, 6H), 2.26 (s, 3H), 3.26 (s, 3H), 6.07–6.62 (m, 5H), 7.22–7.28 (m, 2H)

From the $^1$H-NMR data, the yellow oil obtained was identified as 2-cyclopentadienyl-2-(3-tert-butyl-2-methoxy-5-methylphenyl)propane. The yield was 60%.

(1-4): Synthesis of white solid estimated to be 2-(cyclopentadienyl)(lithium)-2-(3-tert-butyl-2-methoxy-5-methylphenyl)propane In a 50-ml 4-necked flask fitted with a stirrer, under nitrogen atmosphere, 0.28 g (0.99 mmol) of 2-cyclopentadienyl-2-(3-tert-butyl-2-methoxy-5-methylphenyl)propane synthesized in (1-3) above was dissolved in 20 ml of hexane, and the solution was cooled to −70° C. To the solution was slowly added 1.09 mol of nBuLi (0.67 ml of a solution of nBuLi in hexane of a concentration of 1.62 mol/l). Thereafter, the resulting mixture was slowly brought up to room temperature, whereby a white solid precipitated out. The solid was collected by filtration, washed 3 times using 10 ml of hexane in each washing, and dried under reduced pressure to obtain 0.28 g of a white solid estimated to be 2-(cyclopentadienyl)(lithium)-2-(3-tert-butyl-2-methoxy-5-methylphenyl)propane, which is white solid. The yield was 97%.

(1-5) Synthesis of isopropylidene(cyclopentadienyl) (3-tert-butyl-5-methyl-2-phenoxy)titanium dichloride In a 50 ml 4-necked flask fitted with a stirrer, under nitrogen atmosphere, 0.20 g (2.3 mmol) of the white solid estimated to be 2-(cyclopentadienyl)(lithium)-2-(3-tert-butyl-2-methoxy-5-methylphenyl)propane synthesized in (1-4) above was added to 10 ml of hexane, and the mixture was cooled to −70° C. To the mixture was added slowly 0.077 ml (0.13 g, 0.70 mmol) of $TiCl_4$ with a syringe. The resulting solution was slowly brought up to room temperature. The solution turned liver brown and a dark orange solid deposited.

The resulting reaction mixture was filtered to separate into a solid and a solution. The solid was treated 3 times with 10 ml, per one time, of hexane to extract components soluble in hexane, a saturated hydrocarbon solvent. These hexane solutions were combined, concentrated to a volume of 10 ml, and the concentrated liquid was cooled at −20° C. and allowed to stand for 12 hours to deposit a yellow solid. The solid was collected by filtration and dried under reduced pressure. The $^1$H-NMR ($CD_2Cl_2$ solvent) data of the yellow solid are shown below.

δ1.33 (s, 9H), 1.51 (s, 6H), 2.30 (s, 3H), 6.06 (t, 2H), 6.92 (t, 2H), 6.99 (s, 1H), 7.19 (s, 1H)

From the $^1$H-NMR data, the yellow solid obtained above was identified as isopropylidene(cyclopentadienyl)(3-tert-butyl-5-methyl-2-phenoxy)titanium dichloride of the following structural formula. The yield was 34%.

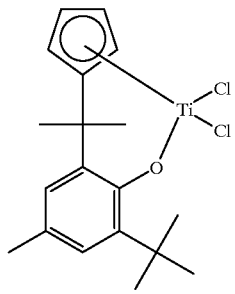

(2) Polymerization

An autoclave with an inner volume of 3 l fitted with a stirrer was dried under reduced pressure, and the inner atmosphere was replaced with argon. Then 1 l of toluene as the solvent and 20 ml of hexene-1 as the α-olefin were placed in the autoclave, and the reactor was brought up to 80° C. After the temperature rise, ethylene was fed into the reactor while the ethylene pressure being controlled at 12 kg/cm$^2$. After the inside of the system had become stable, 0.5 mmol of triisobutylaluminum, then 2.0 μmol of isopropylidene(cyclopentadienyl) (3-tert-butyl-5-methyl-2-phenoxy)titanium dichloride synthesized in (1) above, and succeedingly 6.0 μmol of triphenylmethyl tetrakis (pentafluorophenyl)borate were successively charged into the reactor. Polymerization was carried out for 30 minutes while controlling the temperature at 80° C.

As the result of polymerization, an ethylene-hexene-1 copolymer having an SCB of 22.8, [η] of 1.13, molecular weight (Mw) of 64,000, molecular weight distribution (Mw/Mn) of 2.0 and melting point of 96.1° C. was produced at a rate of 4.0×10$^7$ g per mole of titanium per hour.

EXAMPLE 2
(1) Polymerization
An autoclave with an inner volume of 0.4 l fitted with a stirrer was dried under reduced pressure, and the inner atmosphere was replaced with argon. Then, 195 ml of toluene as the solvent and 5 ml of hexene-1 as the α-olefin were placed in the autoclave, and the reactor was brought up to 60° C. After the temperature rise, ethylene was fed into the reactor while the ethylene pressure being controlled at 6 kg/cm$^2$. After the inside of the system had become stable, 0.25 mmol of triisobutylaluminum, then 1.0 μmol of isopropylidene(cyclopentadienyl) (3-tert-butyl-5-methyl-2-phenoxy)titanium dichloride synthesized in Example 1, and succeedingly 3.0 μmol of triphenylmethyl tetrakis (pentafluorophenyl)borate were successively charged into the reactor. Polymerization was carried out for 30 minutes while controlling the temperature at 60° C.

As the result of polymerization, an ethylene-hexene-1 copolymer having an SCB of 32.8, [η] of 0.98, molecular weight (Mw) of 95,000, molecular weight distribution (Mw/Mn) of 2.8 and melting point of 110.5° C. was produced at a rate of 4.0×10$^7$ g per mole of titanium per hour.

EXAMPLE 3
(1) Polymerization
An autoclave with an inner volume of 0.4 l fitted with a stirrer was dried under reduced pressure, and the inner atmosphere was replaced with argon. Then, 195 ml of toluene as the solvent and 5 ml of hexene-1 as the α-olefin were placed in the autoclave, and the reactor was brought up to 60° C. After the temperature rise, ethylene was fed into the reactor while the ethylene pressure being controlled at 6 kg/cm$^2$. After the inside of the system had become stable, 0.25 mmol of triethylaluminum, then 1.0 μmol of isopropylidene(cyclopentadienyl) (3-tert-butyl-5-methyl-2-phenoxy)titanium dichloride synthesized in Example 1 and succeedingly 3.0 μmol of triphenylmethyl tetrakis (pentafluorophenyl)borate were successively charged into the reactor. Polymerization was carried out for 60 minutes while controlling the temperature at 60° C.

As the result of polymerization, an ethylene-hexene-1 copolymer having an SCB of 18.0, [η] of 1.20 and melting point of 120.8° C. was produced at a rate of 9.9×10$^5$ g per mol of titanium per hour.

EXAMPLE 4
An autoclave with an inner volume of 0.4 l fitted with a stirrer was dried under reduced pressure, and the inner atmosphere was replaced with argon. Then, 170 ml of toluene as the solvent and 30 ml of hexene-1 as the α-olefin were placed in the autoclave, and the reactor was brought up to 60° C. After the temperature rise, ethylene was fed into the reactor while the ethylene pressure being controlled at 6 kg/cm$^2$. After the inside of the system had become stable, 5.0 mmol, in terms of aluminum atom contained, of methylaluminoxane (mfd. by Tosoh-Akzo K.K., MMAO-3A) and then 1.0 μmol of isopropylidene(cyclopentadienyl)(3-tert-butyl-5-methyl-2-phenoxy)titanium dichloride synthesized in Example 1 were fed into the reactor. Polymerization was carried out for 60 minutes while controlling the temperature at 60° C.

As the result of polymerization, an ethylene-hexene-1 copolymer having an SCB of 28.6 and melting point of 82.3° C. was produced at a rate of $7.7 \times 10^5$ g per mole of titanium per hour.

EXAMPLE 5
(1) Polymerization

An autoclave with an inner volume of 0.4 l fitted with a stirrer was dried under reduced pressure, and the inner atmosphere was replaced with argon. Then, 170 ml of toluene as the solvent and 30 ml of hexene-1 as the α-olefin were placed in the autoclave, and the reactor was brought up to 60° C. After the temperature rise, ethylene was fed into the reactor while the ethylene pressure being controlled at 6 kg/cm². After the inside of the system had become stable, 0.5 mmol, in terms of aluminum atom contained, of methylaluminoxane (mfd. by Tosoh-Akzo K.K., MMAO-3A) was fed into the reactor, and then 1.0 μmol of isopropylidene (cyclopentadienyl)(3-tert-butyl-5-methyl-2-phenoxy) titanium dichloride synthesized in Example 1 and 0.5 mmol, in terms of aluminum atom contained, of methylaluminoxane which had been preliminarily contacted with each other were fed into the autoclave. Polymerization was carried out for 60 minutes while controlling the temperature at 60° C.

As the result of polymerization, an ethylene-hexene-1 copolymer having an SCB of 32.4, [η] of 1.99 and melting point of 82.0° C. was produced at a rate of $5.5 \times 10^5$ g per mole of titanium per hour.

EXAMPLE 6
(1) Synthesis of Transition Metal Complex

(1-1) Synthesis of 1-bromo-2-methoxybenzene

In a 50-ml 4-necked flask fitted with a stirrer, under nitrogen atmosphere, 1.03 g (5.92 mmol) of 1-bromo-2-phenol was dissolved in 20 ml of acetonitrile, and succeedingly 0.51 g (9.07 mmol) of potassium hydroxide was added thereto. Further, 1.90 ml (4.33 g, 30.5 mmol) of methyl iodide was slowly added thereto with a syringe, and the resulting reaction mixture was stirred for 12 hours. Thereafter, the solvent was removed with an evaporator, and 20 ml of hexane was added to the resulting residue to extract hexane solubles. The extraction was repeated 3 times. The solvent was removed from the extracts obtained to obtain 0.97 g of a pale yellow oil. The yield was 89%. The $^1$H-NMR (CD$_2$Cl$_2$ solvent) data of the oil are shown below.

δ3.89 (s, 3H), 6.7–7.7 (m, 4H)

From the $^1$H-NMR data, the pale yellow oil obtained was identified as 1-bromo-2-methoxybenzene.

(1-2) Synthesis of 2-(cyclopentadienyl)(lithium)-2-(2-methoxyphenyl)propane In a 100-ml 4-necked flask fitted with a stirrer, under nitrogen atmosphere, 4.50 g (24.1 mmol) of 1-bromo-2-methoxybenzene synthesized in (1-1) above was dissolved in 20 ml of dry diethyl ether, and the solution was cooled to −70° C. Then 24.0 mol of nBuLi (14.8 ml of nBuLi hexane solution of a concentration of 1.62 mol/l) was slowly added thereto, and the resulting liquid was stirred at −70° C. for 2 hours. To the reaction liquid was further added 2.64 g (24.9 mmol) of 6,6-dimethylfulvene dissolved in 10 ml of diethyl ether, and thereafter the resulting mixture was slowly brought up to room temperature, whereby a white solid deposited, which was then collected by filtration. The white solid obtained was washed 3 times by using 10 ml of hexane per one time, and then dried under reduced pressure to obtain 4.0 g of white powder.

A small portion of the white powder was hydrolyzed with dilute hydrochloric acid. The $^1$H-NMR (C$_6$D$_6$ solvent) data of the organic substance thus obtained are as follows.

δ1.66 (s, 3H), 1.75 (s, 3H), 3.26 (s, 3H), 5.9–7.5 (m, 9H)

From the $^1$H-NMR data, the organic substance obtained by hydrolysis was identified, as 2-cyclopentadienyl-2-(1-methoxyphenyl)propane, and consequently the white powder was estimated to be 2-(cyclopentadienyl)(lithium)-2-(2-methoxyphenyl)propane. The yield was 75%.

(1-3) Synthesis of isopropylidene(cyclopentadienyl) (2-phenoxy)titanium dichloride In a 50-ml 4-necked flask fitted with a stirrer, under nitrogen atmosphere, 0.20 g (0.92 mmol) of the white powder estimated to be 2-(cyclopentadienyl)(lithium)-2-(2-methoxyphenyl)propane synthesized in (1-2) above was added to 15 ml of hexane and the mixture was cooled to −70° C. Thereto was slowly added with a syringe a solution of 0.10 ml (0.17 g, 0.91 mmol) of TiCl$_4$ in 5 ml of hexane. The resulting solution was slowly brought up to room temperature. The solution turned light brown, and a brown solid deposited. The reaction mixture was separated by filtration into a solution and a solid. From the solid were extracted 3 times, with 10 ml of hexane per time, components soluble in hexane, a saturated hydrocarbon solvent. These hexane solutions were combined, concentrated to a volume of 10 ml, and the concentrated liquid was cooled at −20° C. and allowed to stand for 12 hours, whereby a yellow solid deposited. The solid was collected by filtration and dried under reduced pressure to obtain 0.10 g of a yellow solid. The $^1$H-NMR (CD$_2$Cl$_2$ solvent) data of the yellow solid are shown below.

δ1.62 (s, 6H), 6.17 (t, 2H), 6.80 (d, 1H), 7.00 (t, 2H), 7.20 (t, 1H), 7.21 (t, 1H), 7.58 (d, 1H)

Additionally, the $^{13}$C-NMR (CD$_2$Cl$_2$ solvent) data are shown below.

δ29.8, 37.3, 114.9, 119.8, 122.4, 125.6, 126.7, 127.8, 136.5, 143.8, 162.7

From the $^1$H-NMR data and $^{13}$C-NMR data, the yellow solid obtained was identified as isopropylidene (cyclopentadienyl)(2-phenoxy)titanium dichloride of the following structural formula:

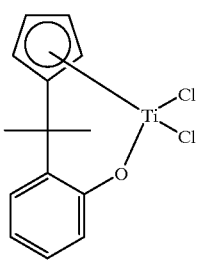

(2) Polymerization

An autoclave with an inner volume of 0.4 l fitted with a stirrer was dried under reduced pressure, and the inner atmosphere was replaced with argon. Then 195 ml of toluene as the solvent and 5 ml of hexene-1 as the α-olefin were placed in the autoclave, and the reactor was brought up to 60° C. After the temperature rise, ethylene was fed into the reactor while the ethylene pressure being controlled at 6 kg/cm$^2$. After the inside of the system had become stable, 0.25 mmol of triisobutylaluminum, then 2.0 μmol of isopropylidene(cyclopentadienyl)(2-phenoxy)titanium dichloride synthesized in (1) above and succeedingly 6.0 μmol of triphenylmethyl tetrakis(pentafluorophenyl)borate were successively charged into the reactor. Polymerization was carried out for 60 minutes while controlling the temperature at 60° C.

As the result of polymerization, an ethylene-hexene-1 copolymer having an SCB of 28.1 and [η] of 1.08 was produced at a rate of 1.8×10$^6$ g per mole of titanium per hour.

EXAMPLE 7

(1) Polymerization

An autoclave with an inner volume of 0.4 l fitted with a stirrer was dried under reduced pressure and the inner atmosphere was replaced with argon. Then 195 ml of toluene as the solvent and 5 ml of hexene-1 as the α-olefin were placed in the autoclave, and the reactor was brought up to 60° C. After the temperature rise, ethylene was fed into the reactor while the ethylene pressure being controlled at 6 kg/cm$^2$. After the inside of the system had become stable, 0.15 mmol of triisobutylaluminum was fed into the reactor, and succeedingly 2.0 μmol of isopropylidene (cyclopentadienyl)(2-phenoxy)titanium dichloride synthesized in Example 6(1) and 0.1 mmol of triisobutylaluminum which had been preliminarily contacted with each other were fed into the autoclave. Polymerization was carried out for 60 minutes while controlling the temperature at 60° C.

As the result of polymerization, an ethylene-hexene-1copolymer having an SCB of 29.0 was produced at a rate of 3.3×10$^6$ g per mole of titanium per hour.

EXAMPLE 8

(1) Polymerization

An autoclave with an inner volume of 0.4 l fitted with a stirrer was dried under reduced pressure, and the inner atmosphere was replaced with argon. Then 170 ml of toluene as the solvent and 30 ml of hexene-1 as the α-olefin were placed in the autoclave, and the reactor was brought up to 60° C. After the temperature rise, ethylene was fed into the reactor while the ethylene pressure being controlled at 30 kg/cm$^2$. After the inside of the system had become stable, 2.0 mmol, in terms of the aluminum atom contained, of methylaluminoxane (mfd. by Tosoh-Akzo K.K., MMAO-3A) and succeedingly 2.0 μmol of isopropylidene (cyclopentadienyl)(2-phenoxy)titanium dichloride synthesized in Example 6(1) were fed into the reactor. Polymerization was carried out for 20 minutes while controlling the temperature at 60° C.

As the result of polymerization, an ethylene-hexene-1 copolymer having an SCB of 7.0 and melting point of 123.7° C. was produced at a rate of 2.3×10$^5$ g per mole of titanium per hour.

Comparative Example 1

(1) Polymerization

An autoclave with an inner volume of 400 ml fitted with a stirrer was dried under reduced pressure and the inner atmosphere was replaced with argon. Then 170 ml of toluene as the solvent and 30 ml of hexene-1 as the α-olefin were placed in the autoclave, and the reactor was brought up to 80° C. After the temperature rise, ethylene was fed into the reactor while the ethylene pressure being controlled at 6 kg/cm$^2$. After the inside of the system had become stable, 0.25 mmol of triethylaluminum, then 5.0 μmol of 2,2'-thiobis(6-tert-butyl-4-methylphenoxy)titanium dichloride synthesized according to the method described in W087/02370 and JP-A-5-230133, and succeedingly 15.0 μmol of triphenylmethyl tetrakis(pentafluorophenyl)borate were successively charged into the reactor. Polymerization was carried out for 60 minutes while controlling the temperature at 80° C.

As the result of polymerization, an ethylene-hexene-1 copolymer having an SCB of 26.1, [η$_1$] of 3.78 and melting point of 116.8° C. was produced at a rate of 2.9×10$^4$ g per mole of titanium.

EXAMPLE 9

Synthesis of 1,5-dimethyl-3-(1-cyclopentadienyl-1-methyl-ethyl)-2-methoxybenzene To a solution (100 ml) of 2-bromo-4,6-dimethylanisole (10.32 g) in anhydrous ether was added dropwise at −78° C. a 1.69 M hexane solution (56.8 ml) of n-butyllithium, the resulting mixture was brought up to room temperature over 2 hours, and the yellow solution thus obtained was cooled to −78° C. To the solution was added dropwise 5-isopropylidene-cyclopenta-1,3-diene (5.87 ml), the resulting mixture was brought up to room temperature over 12 hours and further stirred at room temperature for 1 hour.

The reaction mixture was mixed with an aqueous ammonium chloride solution and then separated into an aqueous layer and an organic layer. Toluene solubles were extracted from the aqueous layer by using toluene, and the toluene solution obtained was combined with the above-mentioned organic layer. The resulting organic solution was washed with saturated aqueous sodium chloride solution and then dried with anhydrous sodium sulfate.

The organic solution thus treated was stripped of the solvent under reduced pressure, and the residue was treated by silica gel column chromatography to obtain yellow oily 1,5-dimethyl-3-(1-cyclopentadienyl-1-methylethyl)-2-methoxybenzene as a mixture of isomers (2.56 g, yield 22%).

$^1$H NMR (CDCl$_3$) δ1.58 (s, 6H), 2.22 (s, 3H), 2.28 (s, 3H), 2.81–2.97 (2H, 2.81:m;2.97:m), 3.26–3.29 (3H, 3.26:m;3.29:m), 6.08–6.48 (m,3H), 6.86 (d, 1H, J=1 Hz), 6.87 (d, 1H, J=1 Hz)

mass spectra (EI, m/e) 242, 227, 211, 196, 177, 162, 149, 136, 119, 105, 91, 81, 65

EXAMPLE 10

Synthesis of isopropylidene(cyclopentadienyl)(3,5-dimethyl-2-phenoxy)titanium dichloride To a hexane solution (10 ml) of 1,5-dimethyl-3-(1-cyclopentadienyl-1-methyl-ethyl)-2-methoxybenzene (0.727 g) was added dropwise at 0° C. a 1.69 M hexane solution (1.95 ml) of n-butyllithium, the resulting mixture was brought up to room temperature and stirred for 12 hours. To the mixture obtained was added at −50° C., while being shielded from light, titanium tetrachloride (0.33 ml), the mixture was brought up to room temperature in 2 hours and further stirred at room temperature for 12 hours. The slurry thus obtained was filtered and the filtrate was concentrated to obtain a raw product. The raw product was recrystallized from hexane to obtain orange crystals of isopropylidene (cyclopentadienyl)(3,5-dimethyl-2-phenoxy)titanium dichloride (0.15 g, yield 14%).

$^1$H NMR (C$_6$D$_6$) δ0.99 (s, 6H), 2.18 (s, 3H), 2.29 (s, 3H), 5.46 (t, 2H, J=3 Hz), 6.30 (t, 2H, 3 Hz), 6.65 (d, 1H, J=2 Hz), 6.95 (d, 1H, J=2 Hz)

EXAMPLE 11

Synthesis of 1-phenyl-3-(1-cyclopentadienyl-1-methyl-ethyl)-2-methoxybenzene

To an anhydrous ether solution (100 ml) of 2-bromo-6-phenylanisole (14.00 g) was added dropwise at −78° C. a 1.69 M hexane solution (63.9 ml) of n-butyllithium, the resulting mixture was brought up to room temperature over 2 hours, and a yellow solution thus obtained was cooled to −78° C. To the solution was added dropwise 5-isopropylidene-cyclopenta-1,3-diene (6.51 ml), the resulting mixture was brought up to room temperature over 12 hours and further stirred at room temperature for 1 hour.

The reaction mixture was mixed with an aqueous ammonium chloride solution and separated into an aqueous layer and an organic layer. The aqueous layer was treated with toluene to extract toluene solubles therefrom, and the toluene solution obtained was combined with the above-mentioned organic layer to obtain an organic solution. The organic solution was washed with saturated aqueous sodium chloride solution and then dried with anhydrous sodium sulfate.

The organic solution was then stripped of the solvent under reduced pressure, and the residue was treated by silica gel column chromatography to obtain yellow oily 1-phenyl-3-(1-cyclopentadienyl-1-methylethyl)-2-methoxybenzene as a mixture of isomers (6.60 g, yield 43%).

$^1$H NMR (CDCl$_3$) δ1.66 (s, 6H), 2.82–2.96 (m, 5H), 6.07–6.45 (m, 3H), 7.05–7.60 (m, 8H) Mass spectra (EI, m/e) 290, 275, 260, 210, 183, 165, 152, 115, 91, 77

EXAMPLE 12

Synthesis of isopropylidene(cyclopentadienyl)-(3-phenyl-2-phenoxy)titanium dichloride To a hexane solution (20 ml) of 1-phenyl-3-(1-cyclopentadienyl-1-methyl-ethyl)-2-methoxybenzene (1.45 g) was added dropwise at 0° C. a 1.69 M hexane solution (3.08 ml) of n-butyllithium, the resulting mixture was brought up to room temperature and stirred for 12 hours. To the mixture obtained was added at −50° C., while being shielded from light, titanium tetrachloride (0.55 ml), the resulting mixture was brought up to room temperature and stirred for 12 hours. The slurry thus obtained was filtered and the filtrate was concentrated to obtain a raw product. The raw product was recrystallized from hexane to obtain orange crystals of isopropylidene(cyclopentadienyl)(3-phenyl-2-phenoxy)titanium dichloride (0.46 g, yield 23%).

$^1$H NMR (C$_6$D$_6$) δ1.20 (s, 6H), 5.39 (t, 2H, J=3 Hz), 6.26 (t, 2H, J=3 Hz), 7.00–7.20 (m, 5H), 7.26 (dd, 1H, J=2 and 8 Hz), 7.40 (t, 1H, J=8 Hz), 7.75 (dd, 1H, 2 and 8 Hz)

EXAMPLE 13

Synthesis of 1-tert-butyl-3-[1-(3-tert-butylcyclopentadienyl)-1-methyl-ethyl]-2-methoxy-5-methylbenzene To an anhydrous ether solution (30 ml) of 2-bromo-6-tert-butyl-4-methylanisole (3.86 g) was added dropwise at −78° C. a 1.69 M hexane solution (17.8 ml) of n-butyllithium, and then the resulting mixture was brought up to room temperature over 2 hours to obtain a yellow solution. The yellow solution was cooled to −78° C., then an anhydrous ether solution (10 ml) of 2-tert-butyl-5-isopropylidene-cyclopenta-1,3-diene (2.43 g) was added dropwise to the solution, the resulting mixture was brought up to room temperature over 12 hours, and further stirred for 1 hour at room temperature.

The reaction mixture thus obtained was mixed with an aqueous ammonium chloride solution and separated into an aqueous layer and an organic layer. The aqueous layer was treated with toluene to extract toluene solubles therefrom, and the toluene solution thus obtained was combined with the above-mentioned organic layer to form an organic solution. The organic solution was washed with saturated aqueous sodium chloride solution and then dried with anhydrous sodium sulfate.

The organic solution was then stripped of the solvent under reduced pressure, and the residue was treated by silica gel column chromatography to obtain yellow oily 1-tert-butyl-3-[1-(3-tert-butyl-cyclopentadienyl)-1-methyl-ethyl]-2-methoxy-5-methylbenzene as a mixture of isomers (1.80 g, yield 35%).

$^1$H NMR (CDCl$_3$) δ1.06–1.19 (m, 15H), 1.37–1.38 (9H;1.37:s;1.38:s), 2.31 (s, 3H), 2.76–2.90 (2H;2.76:m;2.90:m), 3.24–3.26 (3H;3.24:s;3.26:s), 5.72–6.26 (m, 2H), 7.06 (d, 1H, J=1 Hz), 7.10 (d, 1H, J=1 Hz)

EXAMPLE 14

Synthesis of isopropylidene(3-tert-butylcyclopentadienyl)(3-tert-butyl-5-methyl-2-phenoxy)titanium dichloride To a hexane solution (3 ml) of 1-tert-butyl-3-[1-(3-tert-butylcyclopentadienyl)-1-methyl-ethyl]-2-methoxy-5-methylbenzene (0.202 g) was added dropwise at 0° C. a 1.63 M hexane solution (0.55 ml) of n-butyllithium, the resulting mixture was brought up to room temperature and stirred for 12 hours. To the mixture obtained was added at −50° C., while being shielded from light, titanium tetrachloride (0.066 ml), the resulting mixture was brought up to room temperature over 2 hours and then stirred at room temperature for 12 hours. The slurry thus obtained was filtered and the filtrate was concentrated to obtain a raw product. This was recrystallized from hexane to obtain orange crystals of isopropylidene(3-tert-butylcyclopentadienyl)(3-tert-butyl-5-methyl-2-phenoxy)titanium dichloride (0.040 g, yield 15%).

$^1$H NMR (C$_6$D$_6$) δ1.27 (s, 3H), 1.35 (s, 9H), 1.40 (s, 3H), 1.64 (s, 9H), 2.27 (s, 3H), 5.01 (t, 1H, J=3 Hz), 6.41 (t, 1H, J=3 Hz), 6.52 (t, 1H, J=3 Hz), 7.11 (d, 1H, J=2 Hz), 7.14 (d, 1H, J=2 Hz)

EXAMPLE 15

Synthesis of 1-tert-butyl-3-[1-(3-methylcyclopentadienyl)-1-methyl-ethyl]-2-methoxy-5-methylbenzene Under nitrogen atmosphere, a 1.69 M hexane solution (100 ml) of n-butyllithium was added dropwise at −78° C. to an anhydrous ether solution (300 ml) of 2-bromo-6-tert-butyl-4-methylanisole (20.97 g), the resulting mixture was brought up to room temperature over 1 hour, and a yellow solution thus obtained was cooled to −78° C. To the solution was added dropwise an anhydrous ether solution (20 ml) of 2-methyl-5-isopropylidene-cyclopenta-1,3-diene (9.78 g), the resulting mixture was brought up to room temperature over 12 hours and then stirred at room temperature for 1 hour.

The reaction mixture thus obtained was mixed with an aqueous ammonium chloride solution and separated into an aqueous layer and an organic layer. The aqueous layer was treated with toluene to extract toluene solubles therefrom, and the toluene solution thus obtained and the above-mentioned organic layer was combined to obtain an organic solution. The organic layer was washed with saturated aqueous sodium chloride solution and then dried with anhydrous sodium sulfate.

The organic solution was then stripped of the solvent under reduced pressure and the residue was treated by silica gel column chromatography to obtain yellow oily 1-tert-butyl-3-[1-(3-methylcyclopentadienyl)-1-methyl-ethyl]-2-methoxy-5-methylbenzene as a mixture of isomers (3.27 g, yield 13%).

$^1$H NMR (CDCl$_3$) δ1.37–1.39 (9H;1.37:s;1.38:s; 1.39:s), 1.59–1.61 (6H;1.56:s;1.60:s;1.61:s), 1.98 (m, 3H), 2.30 (s, 3H), 2.70–2.84 (m, 2H), 3.30–3.35 (3H;3.30:s;3.31:s;3.35:s), 5.75–6.19 (m, 2H), 7.02–7.08 (m, 2H)

Mass spectra (EI, m/e) 298, 283, 267, 241, 227, 219, 189, 179, 161, 147, 121, 105, 91, 57

EXAMPLE 16

Synthesis of isopropylidene(3-methylcyclopentadienyl)(3-tert-butyl-5-methyl-2-phenoxy)titanium dichloride To a hexane solution (10 ml) of 1-tert-butyl-3-[1-(3-methylcyclopentadienyl)-1-methyl-ethyl]-2-methoxy-5-methylbenzene (0.298 g) was added dropwise at 0° C. a 1.56 M hexane solution (0.96 ml) of n-butyllithium, the resulting mixture was brought up to room temperature and stirred for 12 hours. To the resulting mixture was added, while being shielded from light, at −50° C. titanium tetrachloride (0.11 ml), then the mixture was brought up to room temperature over 3 hours and further stirred at room temperature for 12 hours. The slurry thus obtained was filtered and the filtrate was concentrated to obtain an orange oil of isopropylidene (3-methylcyclopentadienyl)(3-tert-butyl-5-methyl-2-phenoxy)titanium dichloride (0.10 g, yield 25%).

$^1$H NMR (C$_6$D$_6$) δ1.38 (s, 3H), 1.41 (s, 3H), 1.68 (s, 9H), 2.24 (s, 3H), 2.27 (s, 3H), 5.34 (t, 1H, J=3 Hz), 5.72 (t, 1H, J=3 Hz), 6.23 (t, 1H, J=3 Hz), 7.13 (d, 1H, J=1 Hz), 7.14 (d, 1H, J=1 Hz)

EXAMPLE 17

Synthesis of 1-tert-butyldimethylsilyl-3-(1-cyclopentadienyl-1-methyl-ethyl)-2-methoxy-5-methylbenzene Under nitrogen atmosphere, a 1.60 M hexane solution (24.0 ml) of n-butyllithium was added dropwise at −78° C. to an anhydrous ether solution (80 ml) of 2-bromo-6-tert-butyldimethylsilyl-4-methylanisole (6.00 g), the resulting mixture was brought up to room temperature over 2 hours, and the resulting yellow solution was cooled to −78° C. To the cooled solution was added dropwise an anhydrous ether solution (10 ml) of 5-isopropylidene-cyclopenta-1,3-diene (2.43 g), the resulting mixture was brought up to room temperature over 12 hours and then stirred at room temperature for 1 hour.

The reaction mixture obtained was mixed with an aqueous ammonium chloride solution and separated into an aqueous layer and an organic layer. The aqueous layer was treated with toluene to extract toluene solubles therefrom, and the toluene solution thus obtained was combined with the above-mentioned organic layer to obtain an organic solution. The organic solution was washed with saturated aqueous sodium chloride solution and then dried with anhydrous sodium sulfate.

The dried organic solution was stripped of the solvent under reduced pressure and the residue was treated by silica gel column chromatography to obtain yellow oily 1-tert-butyldimethylsilyl-3-(1-cyclopentadienyl-1-methyl-ethyl)-2-methoxy-5-methylbenzene as a mixture of isomers (2.80 g, yield 43%).

$^1$H NMR (CDCl$_3$) δ0.30 (s, 6H), 0.79 (s, 9H), 1.61 (s, 3H), 1.62 (s, 3H), 2.31 (s, 3H), 2.80 (d, 1H, J=2 Hz), 2.95 (d, 1H, J=2 Hz), 3.19 (s, 3H), 6.10–6.40 (m, 3H), 7.09 (d, 1H, J=2 Hz), 7.19 (d, 1H, J=2 Hz)

EXAMPLE 18

Synthesis of isopropylidene(cyclopentadienyl)(3-tert-butyldimethylsilyl-5-methyl-2-phenoxy)titanium dichloride To a hexane solution (30 ml) of 1-tert-butyldimethylsilyl-3-(1-cyclopentadienyl-1-methyl-ethyl)-2-methoxy-5-methylbenzene (1.25 g) was added dropwise at 0° C. a 1.69 M hexane solution (3.25 ml) of n-butyllithium, the resulting mixture was brought up to room temperature and stirred for 12 hours. To the mixture obtained was added, while being shielded from light, at −50° C. titanium tetrachloride (0.41 ml), the resulting mixture was brought up to room temperature over 3 hours and then stirred at room temperature for 12 hours. The resulting slurry was filtered and the filtrate was concentrated to obtain a raw product. This was recrystallized from hexane to obtain orange crystals of isopropylidene (cyclopentadienyl)(3-tert-butyldimethylsilyl-5-methyl-2-phenoxy)titanium dichloride (0.40 g, yield 26%).

$^1$H NMR (C$_6$D$_6$) δ0.65 (s, 6H), 1.10 (s, 9H), 1.23 (s, 6H), 2.25 (s, 3H), 5.56 (t, 2H, J=3 Hz), 6.31 (t, 2H, J=3 Hz), 7.20 (d, 1H, J=2 Hz), 7.28 (d, 1H, J=2 Hz)

EXAMPLE 20

Synthesis of isopropylidene(cyclopentadienyl)(3-t-butyl-5-methyl-2-phenoxy)titanium dichloride To a hexane solution (25 ml) of a white solid (0.51 g, 1.7 mmol) obtained in the same manner as in (1-4) of Example 1 was added at −70° C. titanium tetrachloride (0.18 ml, 1.6 mmol).

Thereafter, the resulting mixture was brought up to room temperature over 3 hours and then stirred at room temperature for 12 hours. The solution turned light brown, and a dark orange solid deposited.

The reaction mixture was filtered to collect the solid, and hexane solubles were extracted from the solid by using hexane (120 ml). The hexane solution obtained were combined, then concentrated to a volume of 30 ml, cooled to −20° C., and allowed to stand for 12 hours. The yellow crystals thus deposited were collected by filtration and dried under reduced pressure to obtain yellow needle-like crystals of isopropylidene(cyclopentadienyl)(3-t-butyl-5-methyl-2-phenoxy)titanium dichloride (0.40 g, yield 64%).

$^1$H NMR (CD$_2$Cl$_2$) δ1.33 (s, 9H), 1.51 (s, 6H), 2.30 (s, 3H), 6.06 (t, J=2.7 Hz, 2H), 6.92 (t, J=2.7 Hz, 2H), 6.99 (s, 1H), 7.19 (s, 1H) Mass spectra (CI, m/e) 386

EXAMPLE 21

Synthesis of (2-allyloxy-3-tert-butyl-5-methylphenyl)chlorodimethylsilane

Into a hexane solution (25 ml) of 2-allyloxy-1-bromo-3-tert-butyl-5-methylbenzene (3.40 g) was added dropwise at −10° C. a 1.66 M hexane solution (7.46 ml) of n-butyllithium, and the resulting mixture was stirred at −10° C. for 30 minutes.

Into the mixture obtained above was added dropwise dichlorodimethylsilane (1.75 g) over one minute, the resulting mixture was brought up to room temperature, then stirred for 2 hours, and thereafter the solvent and the excess of dichlorodimethylsilane were distilled off. To the residue obtained was added hexane (10 ml), the mixture was filtered, and the filtrate was stripped of the solvent under reduced pressure to obtain (2-allyloxy-3-tert-butyl-5-methylphenyl)chlorodimethylsilane as a pale yellow oil (purity 80%) (3.50 g, yield 78%).

Mass spectra (EI, m/e) 296, 281, 253, 245, 220, 205, 189, 161, 145, 128, 115, 93, 75, 41

EXAMPLE 22

Synthesis of (2-allyloxy-3-tert-butyl-5-methylphenyl)dimethyl(2,3,4,5-tetramethylcyclopentadienyl)silane Into a tetrahydrofuran solution (50 ml) of tetramethylcyclopentadiene (1.55 g) was added dropwise at −10° C. a 1.66 M hexane solution (7.87 ml) of n-butyllithium, the resulting mixture was brought up to room temperature, then stirred for 3 hours and then cooled to −10° C.

Into the mixture obtained above was added dropwise a tetrahydrofuran solution (25 ml), cooled to −10° C., of (2-allyloxy-3-tert-butyl-5-methylphenyl)chlorodimethylsilane (purity 80%, 3.50 g) over one minute. The resulting mixture was brought up to room temperature and then stirred for 20 hours.

The reaction mixture was mixed with water (50 ml) and separated into an aqueous layer and an organic layer. The organic layer was washed with saturated aqueous ammonium chloride solution (50 ml) and then the solvent was distilled off to obtain (2-allyloxy-3-tert-butyl-5-methylphenyl)dimethyl(2,3,4,5-tetremethylcyclopentadienyl)silane as a pale yellow oil (purity 58%) (4.52 g, yield 72%).

$^1$H NMR (CDCl$_3$) δ0.13 (s, 6H), 1.42 (s, 9H), 1.69 (s, 6H), 1.79 (s, 6H), 2.28 (s, 3H), 3.42 (s, 1H), 4.40 (dt, 2H, J=2, 2 Hz), 5.28 (dq, 1H, J=2, 11 Hz), 5.54 (dq, 1H, J=2, 17 Hz), 5.99 (ddt, 1H, J=2, 11, 17 Hz), 7.03 (d, 1H, J=2Hz), 7.17 (d, 1H, J=2 Hz)

Mass spectra (EI, m/e) 382, 341, 261, 162, 121, 41

EXAMPLE 23

Synthesis of (2-allyloxy-3-tert-butyl-5-methylphenyl)dimethyl(2,3,4,5-tetramethylcyclopentadienyl)silane To a tetrahydrofuran solution (500 ml) of 2-allyloxy-1-bromo-3-tetra-butyl-5-methylbenzene (33.98 g) was added dropwise at −78° C. a 1.56 M hexane solution (76.92 ml) of n-butyllithium and the resulting mixture was stirred for one hour.

The mixture obtained above was added dropwise, while the temperature being maintained at −20° C. or below, over 30 minutes into a hexane solution (200 ml) at −78° C. of dichlorodimethylsilane (100.0 g). Thereafter the resulting mixture was brought up to room temperature over 2 hours, then stirred for one hour, and the solvent and the excess of dichlorodimethylsilane were distilled off under reduced pressure.

The mixture obtained was dissolved in tetrahydrofuran (200 ml). Into the solution was added dropwise at −78° C. over 30 minutes a solution of tetramethylcyclopentadienyllithium prepared from a tetrahydrofuran solution (400 ml) of tetramethylcyclopentadiene (14.67 g) and a 1.56 M hexane solution (76.92 ml) of n-butyllithium. The resulting mixture was brought up to room temperature over 2 hours and then stirred for 12 hours.

Then the reaction mixture was mixed with an aqueous ammonium chloride solution and separated into an aqueous layer and an organic layer. The aqueous layer was treated with hexane to extract hexane solubles therefrom, and the hexane solution obtained and the above-mentioned organic layer were combined to form an organic solution. The organic solution was washed with saturated aqueous sodium chloride solution and then dried with anhydrous sodium sulfate.

The dried organic solution was stripped of the solvent and the residue was treated by silica gel column chromatography (solvent: hexane) to obtain colorless oily (2-allyloxy-3-tert-butyl-5-methylphenyl)dimethyl(2,3,4,5-tetramethylcyclopentadienyl)silane (24.4 g, yield 53%).

EXAMPLE 24

Synthesis of (2-allyloxy-3-tert-butyl-5-methylphenyl)dimethyl(2,3,4,5-tetramethylcyclopentadienyl)silane Into a mixture of magnesium (0.80 g), iodine (0.05 g) and tetrahydrofuran (200 ml) was added at room temperature 2-allyloxy-1-bromo-3-tert-butyl-5-methylbenzene (0.10 g) and the resulting mixture was stirred at 50° C. for one hour.

Into the mixture obtained above was added dropwise at 60° C. over 6 hours a toluene solution (20 ml) containing 2-allyloxy-1-bromo-3-tert-butyl-5-methylbenzene (8.10 g) and dichlorodimethylsilane (10.9 g), and the resulting mixture was stirred for one hour.

The solvent and the excess of dichlorodimethylsilane were distilled off from the mixture obtained above under reduced pressure, then tetrahydrofuran (100 ml) was added to the residue, and cooled to −78° C. Into the resulting mixture was added at −78° C. a tetrahydrofuran suspension (100 ml) of tetramethylcyclopentadienyllithium (3.71 g) over 5 minutes, the resulting mixture was brought up to room temperature over 2 hours and then stirred for 15 hours.

The reaction mixture was mixed with water (100 ml) and separated into an aqueous layer and an organic layer. The organic layer was stripped of the solvent to obtain (2-allyloxy-3-tert-butyl-5-methylphenyl)dimethyl(tetremethylcyclopentadienyl)silane as a pale yellow oil (purity 45%) (9.70 g, yield 39%).

EXAMPLE 25

Synthesis of dimethylsilyl(tetramethylcyclopentadienyl)(3-tert-butyl-5-methyl-2-phenoxy)titanium dichloride To a chlorobenzene solution (10 ml) containing (2-allyloxy-3-tert-butyl-5-methylphenyl)dimethyl(2,3,4,5- tetramethylcyclopentadienyl)silane (0.96 g) and triethylamine (0.70 ml) was added dropwise at −78° C. a 1.56 M hexane solution (1.61 ml) of n-butyllithium, then the resulting mixture was brought up to room temperature over 2 hours and further stirred for 6 hours.

The mixture thus obtained was cooled to −78° C. and a chlorobenzene solution (3 ml) of titanium tetrachloride (0.276 ml) was added thereto. The resulting mixture was brought up to room temperature over 3 hours while being shielded from light, then stirred for one hour, thereafter brought up to 120° C. over one hour and stirred for 35 hours.

The reaction mixture was filtered, and the filtrate was stripped of the solvent to obtain a reddish brown solid. The solid was recrystallized from a hexanetoluene solvent mixture to obtain red needle-like crystals of dimethylsilyl (tetramethylcyclopentadienyl)(3-tert-butyl-5-methyl-2-phenoxy)titanium dichloride (0.58 g, yield 50%).

EXAMPLE 26

Synthesis of dimethylsilyl (tetramethylcyclopentadienyl)(3-tert-butyl-5-methyl-2-phenoxy)titanium dichloride Into a toluene solution (8 ml) of (2-allyloxy-3-tert-butyl-5-methylphenyl)dimethyl(2,3,4,5-tetramethylcyclopentadienyl)silane (0.28 g) was added dropwise at −78° C. a 1.56 M hexane solution (0.70 ml) of n-butyllithium, the resulting mixture was brought up to room temperature over 2 hours and then stirred for 12 hours.

The mixture obtained was cooled to −78° C., and a chlorobenzene solution (2 ml) of titanium tetrachloride (0.080 ml) was added thereto. The resulting mixture was, while being shielded from light, brought up to room temperature over 3 hours, then stirred for one hour, further brought up to 90° C. over one hour and stirred for 10 hours.

The reaction mixture was filtered and the filtrate was stripped of the solvent to obtain a reddish brown solid. The solid was recrystallized from a hexanetoluene solvent mixture to obtain red needle-like crystals of dimethylsilyl (tetramethylcyclopentadienyl)(3-tert-butyl-5-methyl-2-phenoxy)titanium dichloride (0.14 g, yield 42%).

EXAMPLE 27

Synthesis of (cyclopentadienyl)(2-methoxy-3,5-dimethylphenyl)dimethylsilane

To a tetrahydrofuran solution (100 ml) of 2-bromo-4,6-dimethylanisole (6.45 g) was added dropwise at −78° C. a 1.60 M hexane solution (37.5 ml) of n-butyllithium, and thereafter the resulting mixture was brought up to room temperature over 2 hours.

The mixture obtained above was added dropwise to a hexane solution (200 ml), at −78° C., of dimethyldichlorosilane (19.36 g) over 10 minutes. Then the resulting mixture was brought up to room temperature over 2 hours, then stirred for one hour, and the solvent and the excess of dimethyldichlorosilane were distilled off under reduced pressure.

The mixture obtained was dissolved in tetrahydrofuran (300 ml). Into the resulting solution was added dropwise at −78° C. a 2.0 M tetrahydrofuran solution (15.0 ml) of cyclopentadienylsodium, the resulting mixture was brought up to room temperature over 2 hours and then stirred for 12 hours.

The reaction mixture was mixed with an aqueous ammonium chloride solution, and separated into an aqueous layer and an organic layer. The aqueous layer was treated with hexane to extract hexane solubles therefrom and the hexane solution obtained was combined with the above-mentioned organic layer to obtain an organic solution. The organic solution was washed with saturated aqueous sodium chloride solution and then dried with anhydrous sodium sulfate.

The dried organic solution was stripped of the solvent under reduced pressure, and the residue was treated by silica gel column chromatography (developing solvent hexane) to obtain colorless oily (cyclopentadienyl)(2-methoxy-3,5-dimethylphenyl)dimethylsilane (4.30 g, yield 33%).

$^1$H NMR (CDCl$_3$) δ0.17 (s, 6H), 2.05 (s, 3H), 2.31 (s, 3H), 3.65–3.80 (m, 2H), 3.77 (s, 3H), 5.98–6.45 (m, 3H), 7.12 (d, 1H, J=3 Hz), 7.22 (d, 1H, J=3 Hz)

EXAMPLE 28

Synthesis of (3-tert-butyl-2-methoxy-5-methylphenyl)cyclopentadienyl)diphenylsilane To a tetrahydrofuran solution (200 ml) of 1-bromo-3-tert-butyl-2-methoxy-5-methylbenzene (7.72 g) was added dropwise at −78° C. a 1.60 M hexane solution (37.5 ml) of n-butyllithium, and the resulting mixture was brought up to room temperature over 2 hours.

The mixture obtained above was added dropwise over 15 minutes into a hexane solution (200 ml) at −78° C. of diphenyldichlorosilane (7.60 g). Then the resulting mixture was brought up to room temperature over 2 hours, further stirred for one hour, and the solvent was distilled off under reduced pressure.

The mixture thus obtained was dissolved in tetrahydrofuran (300 ml). Into the resulting solution was added dropwise at −78° C. a 2.0 M tetrahydrofuran solution (15.0 ml) of cyclopentadienylsodium, the resulting mixture was brought up to room temperature over 2 hours and then stirred for 12 hours.

The reaction mixture was mixed with an aqueous ammonium chloride solution and separated into an aqueous layer and an organic layer. The aqueous layer was treated with hexane to extract hexane solubles therefrom, and the hexane solution obtained and the above-mentioned organic layer were combined to obtain an organic solution. The organic solution was washed with saturated aqueous sodium chloride solution and then dried with anhydrous sodium sulfate.

The dried organic solution was stripped of the solvent under reduced pressure, and the residue was treated by silica gel column chromatography (developing solvent: hexane) to obtain colorless oily (3-tert-butyl-2-methoxy-5-methylphenyl)(cyclopentadienyl)diphenylsilane (3.59 g, yield 28%).

$^1$H NMR (CDCl$_3$) δ1.38 (s, 9H), 2.21 (s, 3H), 3.21 (s, 3H), 4.17 (d, 1H, J=6 Hz), 4.60 (d, 1H, J=14 Hz), 6.35–6.78 (m, 3H), 6.98 (d, 1H, J=2 Hz), 7.01 (d, 1H, J=2Hz), 7.20–7.68 (m, 10H)

Mass spectra (EI, m/e) 424, 359, 283, 183, 105

EXAMPLE 29

Synthesis of (3-tert-butyl-2-methoxy-5-methylphenyl)dimethyl(methylcyclopentadienyl)silane To a tetrahydrofuran solution (400 ml) of 1-bromo-3-tert-butyl-2-methoxy-5-methylbenzene (23.16 g) was added dropwise at −78° C. a 1.60 M hexane solution (112.5 ml) of n-butyllithium, and the resulting mixture was brought up to room temperature over 2 hours.

The mixture obtained above was added dropwise over 30 minutes into a hexane solution (200 ml) of dimethyldichlorosilane (58.1 g) of −78° C. Then the resulting mixture was brought up to room temperature over 2 hours, further stirred for one hour, and the solvent and the excess of dichlorodimethylsilane were distilled off under reduced pressure.

The mixture thus obtained was dissolved in tetrahydrofuran (200 ml). Into the solution was added dropwise at −78° C. a methylcyclopentadienyllithium solution prepared from a tetrahydrofuran solution (400 ml) of methylcyclopentadiene (7.21 g) and a 1.60 M hexane solution (57.69 ml) of n-butyllithium. The resulting mixture was brought up to room temperature over 2 hours and then stirred for 12 hours.

The reaction mixture was mixed with an aqueous ammonium chloride solution and separated into an aqueous layer and an organic layer. The aqueous layer was treated with hexane to extract hexane solubles therefrom, and the hexane solution obtained was combined with the above-mentioned organic layer to obtain an organic solution. The organic solution was washed with saturated aqueous sodium chloride solution and then dried with anhydrous sodium sulfate.

The dried organic solution was stripped of the solvents under reduced pressure, and the residue was treated by silica gel column chromatography (developing solvent: hexane) to obtain colorless oily (3-tert-butyl-2-methoxy-5-methylphenyl)dimethyl(methylcyclopentadienyl)silane (18.05 g) as a mixture of isomers in 64% yield.

$^1$H NMR (CDCl$_3$) δ0.16–0.49 (6H;0.16:s;0.18:s; 0.48:s;0.49:s), 1.39–1.42 (9H;1.39:s;1.42:s), 2.04–2.08 (3H;2.04:s;2.08:s), 2.31–2.32 (3H;2.31:s;2.32:s), 2.97–3.05 (m, 1H), 3.61–3.78 (3H;3.61:s;3.78:s), 5.98–6.73 (m, 3H), 6.82 (d, 1H, J=2 Hz), 7.20 (d, 1H, J=2 Hz)

EXAMPLE 30

Synthesis of (tert-butylcyclopentadienyl)(3-t-butyl-2-methoxy-5-methylphenyl)dimethylsilane To a tetrahydrofuran solution (400 ml) of 1-bromo-3-t-butyl-2-methoxy-5-methylbenzene (23.16 g) was added dropwise at −78° C. a 1.60 M hexane solution (112.5 ml) of n-butyllithium and the resulting mixture was brought up to room temperature over 2 hours.

The mixture obtained above was added dropwise into a hexane solution (200 ml) of dimethyldichlorosilane (58.1 g) of −78° C. over 30 minutes. Thereafter the resulting mixture was brought up to room temperature over 2 hours, then stirred for one hour, and thereafter the solvent and the excess of dichlorodimethylsilane were distilled off under reduced pressure.

The mixture obtained was dissolved in tetrahydrofuran (200 ml). Into the resulting solution was added dropwise at −78° over 30 minutes a solution of tert-butylcyclopentadienyllithium prepared from a tetrahydrofuran solution (400 ml) of tert-butylcyclopentadiene (11.00 g) and a 1.60 m hexane solution (57.69 ml) of n-butyllithium. The resulting mixture was brought up to room temperature over 2 hour s and then stirred for 12 hours.

The reaction mixture was mixed with an aqueous ammonium chloride solution and separated into an aqueous layer and an organic layer. The aqueous layer was treated with hexane to extract hexane solubles therefrom, and the hexane solution obtained and the above-mentioned organic layer were combined to obtain an organic solution. The solution was washed with saturated aqueous s odium chloride solution and then dried with anhydrous sodium sulfate.

The dried organic solution was stripped of the solvent under reduced pressure, and the residue was treated by silica gel column chromatography (developing solvent: hexane) to obtain colorless oily (3-tert-butyl-2-methoxy-5-methylphenyl)dimethyl(methylcyclopentadienyl)silane (18.94 g) as a mixture of isomers in 59% yield.

$^1$H NMR (CDCl$_3$) δ0.08–0.43 (6H;0.08:s;0.13: s;0.42:s;0.43:s), 1.12–1.13 (9H;1.12:s;1.13:s), 1.33–1.36 (9H;1.33:s;1.36:s), 2.22–2.25 (3H;2.22:s;2.25:s), 2.97–3.61 (1H;2.97:s; 3.61:s), 3.71 (3H, s), 5.99–6.70 (m, 3H), 7.05 (d, 1H, J=2 Hz), 7.13 (d, 1H, J=2 Hz)

EXAMPLE 31

Synthesis of (3-tert-butyl-2-methoxy-5-methylphenyl)(1H-inden-1-yl)dimethylsilane To a tetrahydrofuran solution (400 ml) of 1-bromo-3-tert-butyl-2-methoxy-5-methylbenzene (23.16 g) was added dropwise at −78° C. a 1.60 M hexane solution (112.5 ml) of n-butyllithium, and the resulting mixture was brought up to room temperature over 2 hours.

The mixture obtained above was added dropwise into a hexane solution (200 ml) of dimethyldichlorosilane (58.10 g) of −78° C. over 30 minutes. Thereafter the resulting mixture was brought up to room temperature over 2 hours, then stirred for one hour and thereafter the solvent and the excess of dichlorodimethylsilane were distilled off under reduced pressure.

The mixture thus obtained was dissolved in tetrahydrofuran (200 ml). Into the resulting solution was added dropwise at −78° C. over 15 hours an indenyllithium solution prepared from a tetrahydrofuran solution (400 ml) of indene (10.45 g) and a 1.60 M hexane solution (57.69 ml) of n-butyllithium, the resulting mixture was brought up to room temperature over 2 hours and then stirred for 12 hours.

The reaction mixture was mixed with an aqueous ammonium chloride solution and separated into an aqueous layer and an organic layer. The aqueous layer was treated with hexane to extract hexane solubles therefrom, and the hexane solution obtained and the above-mentioned organic layer were combined to obtain an organic solution. The organic solution was washed with saturated aqueous sodium chloride solution and then dried with anhydrous sodium sulfate.

The dried organic solution was stripped of the solvent under reduced pressure, and the residue was treated by silica gel column chromatography (developing solvent: hexane) to obtain colorless oily (3-tert-butyl-2-methoxy-5-methylphenyl)(1H-inden-1-yl)dimethylsilane (23.63 g) in 75% yield.

$^1$H NMR (CDCl$_3$) δ0.03 (s, 3H), 0.14 (s, 3H), 1.44 (s, 9H), 2.29 (s, 3H), 3.45 (d, 1H, J=1 Hz), 3.81 (s, 3H), 6.57 (dd, 1H, J=2, 5 Hz), 6.89 (dd, 1H, J=2, 5 Hz), 7.03 (d, 1H, J=2 Hz), 7.20 (d, 1H, J=2 Hz), 7.04–7.50 (m, 4H)

EXAMPLE 32

Synthesis of (3-tert-butyl-2-methoxy-5-methylphenyl)(9H-fluoren-9-yl)dimethylsilane To a tetrahydrofuran solution (100 ml) of 1-bromo-3-tert-butyl-2-methoxy-5-methylbenzene (7.72 g) was added dropwise at −78° C. a 1.60 M hexane solution (37.5 ml) of n-butyllithium, the resulting mixture was brought up to room temperature over 2 hours and then stirred for 3 hours.

The mixture obtained above was added dropwise into a hexane solution (100 ml) of dichlorodimethylsilane (19.36 g) of −78° C. over 10 minutes. Thereafter the resulting mixture was brought up to room temperature over 2 hours, then stirred for one hour and thereafter the solvent and the excess of dichlorodimethylsilane were distilled off under reduced pressure.

The resulting mixture was dissolved in tetrahydrofuran (150 ml). Into the solution was added dropwise at −78° C. a solution of fluorenyllithium prepared from a tetrahydrofuran solution (100 ml) of fluorene (4.99 g) and a 1.60 M hexane solution (18.25 ml) of n-butyllithium, the resulting mixture was brought up to room temperature over 2 hours and then stirred for 12 hours.

Then the reaction mixture was mixed with an aqueous ammonium chloride solution and separated into an aqueous layer and an organic layer. The aqueous layer was treated with hexane to extract hexane-solubles therefrom. The hexane solution obtained and the above-mentioned organic layer were combined to obtain an organic solution. The organic solution was washed with saturated aqueous sodium chloride solution and dried with anhydrous sodium sulfate.

The dried organic solution was stripped of the solvent under reduced pressure, and the residue was recrystallized from a tetrahydrofuran-hexane solvent mixture to obtain colorless crystals of (3-tert-butyl-2-methoxy-5-methylphenyl)(9H-fluoren-9-yl)dimethylsilane (6.82 g) in 57% yield.

$^1$H NMR (CDCl$_3$) δ0.21 (s, 6H), 1.50 (s, 9H), 2.33 (s, 3H), 3.82 (s, 3H), 4.40 (s, 1H), 6.99 (d, 1H, J=2 Hz), 7.29 (d, 1H, J=2 Hz), 7.12-7.38 (m, 6H), 7.82 (d, 2H, J=8 Hz)

EXAMPLE 33

Synthesis of (3-tert-butyl-2-methoxy-5-methylphenyl)(9H-fluoren-9-yl)diphenylsilane To a tetrahydrofuran solution (100 ml) of 1-bromo-3-t-butyl-2-methoxy-5-methylbenzene (5.24 g) was added dropwise at −78° C. a 1.60 M hexane solution (25.0 ml) of n-butyllithium, the resulting mixture was brought up to room temperature over 2 hours.

The mixture obtained above was added dropwise into a hexane solution (100 ml) of diphenyldichlorosilane (5.06 g) of −78° C. over 10 minutes. Then the resulting solution was brought up to room temperature over 2 hours, then stirred for one hour, and the solvent was distilled off under reduced pressure.

The mixture obtained was dissolved in tetrahydrofuran (150 ml). To the resulting solution was added dropwise at −78° C. a solution of fluorenyllithium prepared from a tetrahydrofuran solution (100 ml) of fluorene (3.32 g) and a 1.60 M hexane solution (12.5 ml) of n-butyllithium, the resulting mixture was brought up to room temperature over 2 hours, and then stirred for 12 hours.

The reaction mixture was mixed with an aqueous ammonium chloride solution and separated into an aqueous layer and an organic layer. The aqueous layer was treated with hexane to extract hexane solubles therefrom, and the hexane solution obtained and the above-mentioned organic layer were combined to obtain an organic solution. The organic solution was washed with saturated aqueous sodium chloride solution and then dried with anhydrous sodium sulfate.

The dried organic solution was stripped of the solvent under reduced pressure, and the residue was recrystallized from pentane to obtain colorless crystals of (3-tert-butyl-2-methoxy-5-methylphenyl)(9H-fluoren-9-yl)diphenylsilane (4.31 g, yield 40%).

$^1$H NMR (CDCl$_3$) δ1.46 (s, 9H), 2.23 (s, 3H), 3.39 (s, 3H), 4.92 (s, 1H), 7.00 (dt, 2H, J=1, 7 Hz), 7.10 (d, 1H, J=1 Hz), 7.14 (d, 4H, J=8 Hz), 7.19 (d, 1H, J=1 Hz), 7.21–7.30 (m, 10H), 7.52 (d, 2H, J=8 Hz)

Mass spectra (EI, m/e) 524, 359, 282, 177, 165, 77

EXAMPLE 34

Synthesis of (3-tert-butyl-2-methoxymethyloxy-5-methylphenyl)dimethyl (2,3,4,5-tetramethylcyclopentadienyl)silane To a tetrahydrofuran solution (300 ml) of 1-bromo-3-t-butyl-methoxymethyloxy-5-methylbenzene (11.48 g) was added dropwise at −78° C. a 1.60 M hexane solution (25.0 ml) of n-butyllithium, and the resulting mixture was stirred for 1 hour.

The mixture obtained above was added dropwise at a temperature not higher than −20° C. over 30 minutes into a hexane solution (200 ml) of dimethyldichlorosilane (5.16 g) of −78° C. Thereafter the resulting mixture was brought up to room temperature over 2 hours, then stirred for one hour, and the solvent was distilled off under reduced pressure.

The mixture thus obtained was dissolved in tetrahydrofuran (200 ml). To the resulting solution was added dropwise at −78° C. a solution of tetramethylcyclopentadienyllithium prepared from a tetrahydrofuran solution (300 ml) of tetramethylcyclopentadiene (4.88 g) and a 1.60 M hexane solution (25.0 ml) of n-butyllithium. Thereafter the resulting mixture was brought up to room temperature over 2 hours and then stirred for 12 hours.

The reaction mixture was mixed with an aqueous ammonium chloride solution, and separated into an aqueous layer and an organic layer. The aqueous layer was treated with hexane to extract hexane solubles therefrom, and the hexane solution obtained and the above-mentioned organic layer were combined to obtain an organic solution. The organic solution was washed with saturated aqueous sodium chloride solution and then dried with anhydrous sodium sulfate.

The dried organic solution was stripped of the solvent under reduced pressure, and the residue was treated by silica gel column chromatography (developing solvent: hexane) to obtain colorless oily (3-tert-butyl-2-methoxymethyloxy-5-methylphenyl)dimethyl(2,3,4,5-tetramethylcyclopentadienyl)silane (5.60 g) in 36% yield.

$^1$H NMR (CDCl$_3$) δ0.13 (s, 6H), 1.39 (s, 9H), 1.69 (s, 6H), 1.78 (s, 6H), 2.29 (s, 3H), 3.43 (s, 1H), 4.40 (dd, 2H, J=2, 2 Hz), 5.27 (ddd, 1H, J=2, 2, 9 Hz), 5.53 (ddd, 1H, J=2, 2, 17 Hz), 6.03 (ddddd, 1H, J=2, 2, 2, 9, 17 Hz), 7.03 (d, 1H, J=2 Hz), 7.17 (d, 1H, J=2 Hz)

EXAMPLE 35

Synthesis of (2-benzyloxy-3-tert-butyl-5-methylphenyl)dimethyl(2,3,4,5-tetramethylcyclopentadienyl)silane To a tetrahydrofuran solution (300 ml) of 2-benzyloxy-l-bromo-3-t-butyl-5-methylbenzene (29.30 g) was added dropwise at −78° C. a 1.56 M hexane solution (51.28 ml) of n-butyllithium, and the resulting mixture was stirred for one hour.

The mixture obtained above was added dropwise at a temperature not higher than −20° C. over 30 minutes into a solution of −78° C. of dimethyldichlorosilane (100.0 g) dissolved in hexane solution (150 ml). Then the resulting mixture was brought up to room temperature, then stirred for one hour, and the solvent and the excess of dichlorodimethylsilane were distilled off under reduced pressure.

The mixture obtained was dissolved in tetrahydrofuran (200 ml). Into the resulting solution was added dropwise at −78° C. a solution of tetramethylcyclopentadienyllithium prepared from a tetrahydrofuran solution (500 ml) of tetramethylcyclopentadiene (9.78 g) and a 1.56 M hexane solution (51.28 ml) of n-butyllithium. The resulting mixture was brought up to room temperature over 2 hours and then stirred for 12 hours.

The reaction mixture was mixed with an aqueous ammonium chloride solution, and separated into an aqueous layer and an organic layer. The aqueous layer was treated with hexane to extract hexane solubles therefrom, and the hexane solution obtained and the above-mentioned organic layer were combined to obtain an organic solution. The organic solution was washed with saturated aqueous sodium chloride solution and then dried with anhydrous sodium sulfate.

The dried organic solution was stripped of the solvent under reduced pressure, and the residue was treated by silica gel column chromatography (developing solvent: hexane) to obtain colorless oily (2-benzyloxy-3-tert-butyl-5-methylphenyl)dimethyl(2,3,4,5-tetramethylcyclopentadienyl)silane (17.6 g, yield 51%).

$^1$H NMR (CDCl$_3$) δ0.01 (s, 6H), 1.33 (s, 9H), 1.52 (s, 6H), 1.67 (s, 6H), 2.24 (s, 3H), 3.32 (s, 1H), 4.94 (s, 2H), 6.99 (d, 1H, J=2 Hz), 7.13 (d, 1H, J=2 Hz), 7.21 (dd, 2H, J=7, 7 Hz), 7.29 (dt, 1H, J=1, 7 Hz), 7.40 (dd, 2H, J=1, 7 Hz)

Mass spectra (EI, m/e) 432, 341, 311, 295, 255, 91, 57

EXAMPLE 36

Synthesis of (2-tert-butyldimethylsilyloxy-3-tert-butyl-5-methylphenyl)dimethyl(2,3,4,5-tetramethylcyclopentadienyl)silane A tetrahydrofuran solution (10 ml) of 3-tert-butyl-2-tert-butyldimethylsilyloxy-1-bromo-5-methylbenzene (0.715 g) was cooled to −78° C., then a hexane solution (1.28 ml) of n-butyllithium was added thereto, and the resulting mixture was stirred for one hour. To the mixture obtained was added (2,3,4,5-tetramethylcyclopentadienyl)dimethylsilyl chloride (0.429 g) and the mixture was stirred at room temperature for 10 hours.

The reaction mixture was mixed with an aqueous ammonium chloride solution (10 ml) and separated into an aqueous layer and an organic layer. The aqueous layer was treated with ethyl acetate to extract ethyl acetate solubles therefrom. The ethyl acetate solution obtained and the above-mentioned organic layer were combined to obtain an organic solution. The organic solution was dried with anhydrous sodium sulfate, then stripped of the solvent, and the residue was treated by silica gel column chromatography (developing solvent: hexane) to obtain yellow oily (2-tert-butyl-dimethylsilyloxy-3-tert-butyl-5-methylphenyl)dimethyl(2,3,4,5-tetramethylcyclopentadienyl)silane (0.30 g, yield 34%).

$^1$H NMR (CDCl$_3$) δ0.21 (s, 12H), 0.67 (s, 9H), 1.38 (s, 9H), 1.85 (s, 6H), 2.10 (s, 6H), 2.28 (s, 3H), 3.32 (s, 1H), 6.91 (d, 1H, J=2 Hz), 7.05 (d, 1H, J=2 Hz)

Mass spectra (EI, m/e) 456, 399, 326, 223, 178, 147, 133, 105, 57

EXAMPLE 37

Synthesis of (2-allyloxy-3-tert-butyl-5-methylphenyl)dimethyl(cyclopentadienyl)silane To a tetrahydrofuran solution (200 ml) of 2-allyloxy-1-bromo-3-tert-butyl-5-methylbenzene (17.00 g) was added dropwise at −78° C. a 1.66 M hexane solution (36.2 ml) of n-butyllithium, and the resulting mixture was stirred for one hour.

The mixture obtained above was added dropwise at a temperature lower than −20° C. over 15 minutes into a solution of −78° C. of dimethyldichlorosilane (50.0 g) dissolved in hexane (100 ml). Then the resulting mixture was brought up to room temperature over 2 hours, then stirred for one hour, and the solvent and the excess of dichlorodimethylsilane were distilled off under reduced pressure.

The mixture obtained was dissolved in tetrahydrofuran (75 ml). To the solution was added dropwise at −78° C. a 2 M tetrahydrofuran solution (30 ml) of cyclopentadienylsodium, the resulting mixture was brought up to room temperature over 2 hours and further stirred for 12 hours.

The reaction mixture was mixed with an aqueous ammonium chloride solution and separated into an aqueous layer and an organic layer. The aqueous layer was treated with hexane to extract hexane solubles therefrom, and the hexane solution obtained and the above-mentioned organic layer were combined to obtain an organic solution. The organic solution was washed with saturated aqueous sodium chloride solution and then dried with anhydrous sodium sulfate.

The dried organic solution was stripped of the solvent under reduced pressure, and the residue was w treated by silica gel column chromatography (developing solvent: hexane) to obtain colorless oily (2-allyloxy-3-tert-butyl-5-methylphenyl)dimethyl(cyclopentadienyl)silane (7.3 g, yield 37%).

$^1$H NMR (CDCl$_3$) δ0.19 (s, 6H), 1.45 (s, 9H), 2.36 (s, 3H), 3.11 (s, 1H), 4.43 (dt, 2H, J=2, 5 Hz), 5.31 (dq, 1H, J=2, 11 Hz), 5.57 (dq, 1H, J=2, 17 Hz), 6.07 (ddt, 1H, J=5, 11, 17 Hz), 6.40–6.70 (m, 4H), 7.16 (d, 1H, J=2 Hz), 7.22 (d, 1H, J=2 Hz)

Mass spectra (EI, m/e) 326, 311, 285, 220, 41

EXAMPLE 38

Synthesis of dimethylsilyl(cyclopentadienyl)(3-tert-butyl-5-methyl-2-phenoxy)titanium dichloride To a toluene solution (15 ml) of (2-allyloxy-3-tert-butyl-5-methylphenyl)dimethyl(cyclopentadienyl)silane (1.62 g) was added dropwise at −78° C. a 1.66 M hexane solution (2.99 ml) of n-butyllithium, the resulting mixture was brought up to room temperature over 2 hours, and then stirred for 12 hours. The mixture obtained was cooled to −78° C., and a toluene solution (5 ml) of titanium tetrachloride (0.545 ml) was added thereto. The resulting mixture, while being shielded from light, was brought up to room temperature over 2 hours and then stirred for 12 hours.

The reaction mixture was filtered, and the filtrate was stripped of the solvent under reduced pressure to obtain a reddish brown solid. The solid was recrystallized from a hexane-toluene solvent mixture to obtain red needle-like crystals of dimethylsilyl(cyclopentadienyl)(3-tert-butyl-5-methyl-2-phenoxy)titanium dichloride (0.72 g, yield 36%).

$^1$H NMR (C$_6$D$_6$) δ0.27 (s, 6H), 1.63 (s, 9H), 2.21 (s, 3H), 6.09 (t, 2H, J=2 Hz), 6.65 (t, 2H, J=2 Hz), 7.08 (d, 1H, J=2 Hz), 7.21 (d, 1H, J=2 Hz)

EXAMPLE 39

Synthesis of (2-allyloxy-3-tert-butyl-5-methylphenyl)dimethyl(tert-butylcyclopentadienyl)silane To a tetrahydrofuran solution (200 ml) of 2-allyloxy-1-bromo-3-t-butyl-5-methylbenzene (17.00 g) was added dropwise at −78° C. a 1.66 M hexane solution (36.2 ml) of n-butyllithium, and the resulting mixture was stirred for one hour.

The mixture obtained above was added dropwise at a temperature not higher than −20° C. over 15 minutes into a solution of −78° C. of dimethyldichlorosilane (50.0 g) dissolved in hexane (100 ml). The resulting mixture was then brought up to room temperature over 2 hours, then stirred for one hour, and the solvent and the excess of dimethyldichlorosilane were distilled off under reduced pressure.

The mixture obtained was dissolved in tetrahydrofuran (75 ml). Into the solution was added dropwise at −78° C. a solution of tert-butylcyclopentadienyllithium prepared from a tetrahydrofuran solution (250 ml) of 5-isopropylidenecyclopenta-1,3-diene (6.37 g) and a 1.05 M methyllithium-ether solution (57.2 ml), the resulting mixture was brought up to room temperature over 2 hours, and then stirred for 12 hours.

The reaction mixture was mixed with an aqueous ammonium chloride solution and separated into an aqueous layer and an organic layer. The aqueous layer was treated with hexane to extract hexane solubles therefrom. The hexane solution obtained and the above-mentioned organic layer were combined to obtain an organic solution. The organic solution was washed with saturated aqueous sodium chloride solution and then dried with anhydrous sodium sulfate.

The dried organic solution was stripped of the solvent under reduced pressure, and the residue was treated by silica gel column chromatography (developing solvent: hexane) to obtain colorless oily (2-allyloxy-3-tert-butyl-5-methylphenyl)dimethyl(tert-butylcyclopentadienyl)silane (6.58 g, yield 29%) as a mixture of isomers.

$^1$H NMR (CDCl$_3$) δ6 0.17–0.55 (6H;0.17:s;0.22:s; 0.54:s;0.55:s), 1.22–1.23 (9H;1.22:s;1.23:s), 1.43–1.46 (9H;1.43:s;1.46:s), 2.34–2.36 (3H;2.34:s;2.36:s), 3.08–3.76 (1H;3.08:s; 3.76:s), 4.27–4.60 (m, 2H), 5.30–5.62 (m, 2H), 6.08–6.12 (m, 1H), 6.20–6.60 (m, 3H), 7.17 (d, 1H, J=2 Hz), 7.23 (d, 1H, J=2 Hz)

Mass spectra (EI, m/e) 382, 325, 261, 203, 172, 41

EXAMPLE 40

Synthesis of dimethylsilyl(3-tert-butylcyclopentadienyl)(3-tert-butyl-5-methyl-2-phenoxy)titanium dichloride To a toluene solution (15 ml) of (2-allyloxy-3-tert-butyl-5-methylphenyl)dimethyl(tert-butylcyclopentadienyl)silane (1.53 g) was added dropwise at −78° C. a 1.66 M hexane solution (2.41 ml) of n-butyllithium, the resulting mixture was brought up to room temperature over 2 hours and then stirred for 12 hours. The mixture obtained was cooled to −78° C., and a toluene solution (5 ml) of titanium tetrachloride (0.440 ml) was added thereto. The reaction mixture obtained, while being shielded from light, was brought up to room temperature over 2 hours and then stirred for 12 hours.

The reaction mixture was filtered, and the filtrate was stripped of the solvent to obtain a reddish brown solid. The solid was recrystallized from a hexane-toluene solvent mixture to obtain dimethylsilyl(3-tert-butylcyclopentadienyl)(3-tert-butyl-5-methyl-2-phenoxy)titanium dichloride (0.09 g, yield 5%) as orange crystals.

$^1$H NMR (C$_6$D$_6$) δ0.36 (s, 3H), 0.40 (s, 3H), 1.38 (s, 9H), 1.65 (s, 9H), 2.24 (s, 3H), 5.73 (dd, 1H, J=2, 3 Hz), 6.79 (dd, 1H, J=2, 3 Hz), 6.82 (dd, 1H, J=2, 3 Hz), 7.15 (d, 1H, J=2 Hz), 7.25 (d, 1H, J=2 Hz)

EXAMPLE 41

Synthesis of (2-allyloxy-3-tert-butyl-5-methylphenyl)dimethyl(methylcyclopentadienyl) silane To a tetrahydrofuran solution (50 ml) of 2-allyloxy-1-bromo-3-tert-5-methylbenzene (5.6 g) was added dropwise at −78° C. a 1.65 M hexane solution (12.5 ml) of n-butyllithium, and the resulting mixture was stirred at −78° C. for 1.5 hours.

The mixture obtained above was added dropwise into a hexane solution (25 ml) of dichlorodimethylsilane (12.1 g) of −78° C. over 3 minutes. The resulting mixture was brought up to room temperature over 2 hours, then stirred for 24 hours, and the solvent and dichlorodimethylsilane were distilled off under reduced pressure.

Tetrahydrofuran (50 ml) was added to the mixture obtained above, and further a tetrahydrofuran solution (30 ml) of lithium methylcyclopentadienide (3.0 g) was added thereto at −78° C. over one minute, the resulting mixture was brought up to room temperature over 2 hours and then stirred for 3 hours.

The reaction mixture was mixed with water (40 ml) and separated into an aqueous layer and an organic layer. The organic layer was stripped of the solvent, and the residue obtained was treated with a silica gel column to obtain a pale yellow oil (2.5 g, purity 90%) of an isomer mixture of (2-allyloxy-3-tert-butyl-5-methylphenyl)dimethyl (methylcyclopentadienyl)silane. The yield of the intended product was 33%.

$^1$H NMR (C$_6$D$_6$) δ0.08–0.09 (3H;0.08:s;0.09:s), 0.39–0.41 (3H;0.39:s;0.41:s), 1.32–1.51 (9H;1.32:s;1.36:s;1.39:s;1.51:s), 1.96–2.03 (3H;1.96:s;1.99:s;2.03:s), 2.24–2.27 (3H;2.24:s;2.27:s), 2.90–3.68 (1H;2.90:s; 2.98:s;3.68:s), 4.17–4.50 (2H;4.17:m;4.33:s; 4.50:d, J=5 Hz), 5.22 (d, 1H, J=10Hz), 5.48 (d, 1H, J=17 Hz), 5.79–5.98 (m, 1H), 6.14 (d, 1H, J=10Hz), 6.38 (d, 1H), 7.07–7.16 (m, 3H)

Mass spectra (EI, m/e) 340, 325, 298, 283, 245, 221, 205, 189, 159, 145, 120, 91, 75, 61, 41

EXAMPLE 42

Synthesis of dimethylsilyl(methylcyclopentadienyl) (3-tert-butyl-5-methyl-2-phenoxy)titanium dichloride To a hexane solution (10 ml) of (2-allyloxy-3-tert-butyl-5-methylphenyl)dimethyl(methylcyclopentadienyl)silane (0.75 g) was added dropwise at −78° C. a 1.66 M hexane solution (2.1 ml) of n-butyllithium. The resulting mixture was brought up to room temperature over 2 hours and then stirred for 12 hours. To the mixture obtained were added toluene (25 ml) and then, at room temperature, titanium tetrachloride (0.40 g). The resulting mixture was stirred at 75° C. for 24 hours while being shielded from light.

The reaction mixture was filtered, and the filtrate was stripped of the solvent to obtain a black tar. The tar was treated with hexane (5 ml) to extract hexane solubles therefrom. The hexane solution thus obtained was stripped of the solvent to obtain a reddish black tar (0.3 g, yield 33%) of dimethylsilyl(methylcyclopentadienyl)(3-t-butyl-5-methyl-2-phenoxy)titanium dichloride as an isomer mixture.

$^1$H NMR (C$_6$D$_6$) δ6 0.24–0.34 (6H;0.24:s;0.32:s; 0.33:s;0.34:s), 1.58–1.64 (9H;1.58:s;1.59:s; 1.62:s;1.69:s), 2.15–2.26 (6H;2.15:s;2.19:s; 2.21:s;2.24:s;2.26:s), 5.81 (s,

1H), 6.14 (t, 1H, J=2 Hz), 6.46 (t, 1H, J=2 Hz), 7.12 (d, 1H, J=1 Hz), 7.24 (d, 1H, J=1 Hz)

EXAMPLE 43

Synthesis of (2-allyloxy-3-tert-butyl-5-methylphenyl)(indenyl)dimethylsilane

To a tetrahydrofuran solution (150 ml) of 2-allyloxy-1-bromo-3-tert-butyl-5-methylbenzene (18.9 g) was added dropwise at −78° C. a 1.65 M hexane solution (40.4 ml) of n-butyllithium, and the resulting mixture was stirred at −78° C. for 2 hours.

The mixture obtained above was added dropwise to a hexane solution (80 ml) of −78° C. of dichlorodimethylsilane (12.1 g) over 5 minutes, the resulting mixture was brought up to room temperature over 2 hours, then stirred for 24 hours, and the solvent and dichlorodimethylsilane were distilled off under reduced pressure.

To the mixture obtained was added tetrahydrofuran (150 ml), the resulting mixture was cooled to −78° C., and a tetrahydrofuran solution (100 ml) of indenyllithium (8.2 g) was added thereto over 3 minutes. The resulting mixture was brought up to room temperature over 2 hours and stirred for 5 hours.

The reaction mixture was mixed with water (100 ml) and separated into an aqueous layer and an organic layer. The organic layer was stripped of the solvent to obtain an oil. The oil was treated with a silica gel column to obtain a yellow oil (11.0 g, purity 94%) of an isomer mixture of (2-allyloxy-3-tert-butyl-5-methylphenyl)(indenyl)dimethylsilane. The yield of the intended product was 43%.

$^1$H NMR ($C_6D_6$) δ0.09 (s, 3H), 0.55 (s, 3H), 1.32–1.41 (9H;1.32:s;1.41:s), 2.28–2.29 (3H;2.28:s; 2.29:s), 3.40 (s, 1H), 4.03 (s, 1H), 4.15 (t, 1H, J=2 Hz), 4.39 (dd, 2H, J=2.2 Hz), 5.05–5.24 (1H, 5.05:s;5.08:s;5.18:s;5.24:d, J=9 Hz), 5.51 (d, 1H, J=17 Hz), 5.69–6.08 (m, 1H), 6.54 (dd, 1H, J=2.6 Hz), 6.80–7.50 (m, 5H)

Mass spectra (EI, m/e) 340, 325, 298, 283, 245, 221, 205, 189, 159, 145, 120, 91, 75, 61, 41

EXAMPLE 44

Synthesis of dimethylsilyl(indenyl)(3-tert-butyl-5-methyl-2-phenoxy)titanium dichloride To a toluene solution (20 ml) of (2-allyloxy-3-tert-butyl-5-methylphenyl)(indenyl)dimethylsilane (2.2 g) was added triethylamine (1.50 g) at room temperature. The resulting mixture was cooled to −30° C., and a 1.66 M hexane solution (4.8 ml) of n-butyllithium was added dropwise thereto. The resulting mixture was brought up to room temperature and stirred for 12 hours. To the mixture obtained was added dropwise titanium tetrachloride (1.35 g) at room temperature, and the resulting mixture was stirred at 95° C. for 24 hours while being shielded from light.

The reaction mixture was filtered, the solid obtained was washed with toluene (15 ml), and the filtrate was stripped of the solvent to obtain a reddish black oil (2.9 g). Pentane (10 ml) was added to the oil, and the insoluble portion was dried under reduced pressure to obtain reddish brown powder of dimethylsilyl(indenyl)(3-tert-butyl-5-methyl-2-phenoxy)titanium dichloride (0.25 g, yield 11%).

$^1$H NMR ($C_6D_6$) δ0.45 (s, 3H), 0.50 (s, 3H), 1.44 (s, 9H), 2.27 (s, 3H), 6.69–6.75 (m, 2H), 6.78–6.80 (1H; 6.79:d, J=1 Hz;6.80:d, J=1 Hz), 6.92–6.98 (m, 1H), 7.15 (s, 1H), 7.23 (dd, 2H, J=2.6 Hz), 7.57 (dt, 1H, J=9.1 Hz)

EXAMPLE 45

Synthesis of (2-allyloxy-3-tert-butyl-5-methylphenyl)dimethyl(9H-fluorene-9-yl)silane To a tetrahydrofuran solution (200 ml) of 2-allyloxy-1-bromo-3-t-butyl-5-methylbenzene (17.00 g) was added dropwise at −78° C. a 1.66 M hexane solution (36.2 ml) of n-butyllithium, and the resulting mixture was stirred for 1 hour.

The mixture obtained above was added dropwise at a temperature lower than −20° C. over 15 minutes to a solution of −78° C. of dimethyldichlorosilane (50.0 g) dissolved in hexane (100 ml). The resulting mixture was brought up to room temperature over 2 hours, further stirred for one hour, and the solvent and the excess of dichlorodimethylsilane were distilled off under reduced pressure.

The mixture obtained was dissolved in tetrahydrofuran (75 ml). To the solution was added dropwise at −78° C. fluorenyllithium prepared from a tetrahydrofuran solution (250 ml) of fluorene (9.97 g) and a 1.66 M n-butyllithium-hexane solution (36.2 ml). The resulting mixture was then brought up to room temperature over 2 hours and further stirred for 12 hours.

The reaction mixture was mixed with aqueous ammonium chloride solution and separated into an aqueous layer and an organic layer. The aqueous layer was treated with hexane to extract hexane solubles therefrom, and the hexane solution obtained and the above-mentioned organic layer were combined to obtain an organic solution. The organic solution was washed with saturated aqueous sodium chloride solution and then dried with anhydrous sodium sulfate.

The dried organic solution was stripped of the solvent under reduced pressure, and the residue was treated by silica gel column chromatography (developing solvent: hexane) to obtain colorless oily (2-allyloxy-3-tert-butyl-5-methylphenyl)dimethyl(9H-fluoren-9-yl)silane (12.04 g, yield 47%).

$^1$H NMR ($CDCl_3$) δ0.10 (s, 6H), 1.56 (s, 9H), 2.40 (s, 3H), 4.51 (s, 1H), 4.52 (dt, 2H, J=2, 4 Hz), 5.37 (dq, 1H, J=2, 8 Hz), 5.63 (dq, 1H, J=2, 17 Hz), 6.14 (ddt, 1H, J=4, 8, 17 Hz), 7.08 (d, 1H, J=2 Hz), 7.23 (d, 1H, J=2 Hz), 7.23 (dd, 2H, J=7, 8 Hz), 7.39 (dd, 2H, J=7, 8 Hz), 7.40 (d, 2H, J=7 Hz), 7.92 (d, 2H, J=8 Hz)

EXAMPLE 46

Synthesis of 2-allyloxy-1-bromo-3,5-dimethylbenzene

To a solution of 0° C. of 2-bromo-4,6-dimethylphenol (88.02 g) dissolved in acetonitrile (500 ml) was added potassium hydroxide (30.0 g) and the resulting mixture was stirred for 2 hours to obtain a blue solution. Allyl bromide (100 g) was added dropwise at a temperature not higher than 10° C. to the blue solution, the mixture was brought up to room temperature and then stirred for 6 hours.

The reaction mixture was mixed with an aqueous ammonium chloride solution and separated into an aqueous layer and an organic layer. The aqueous layer was treated with hexane to extract hexane solubles therefrom, and the hexane solution obtained and the above-mentioned organic layer were combined to obtain an organic solution. The organic solution was washed with saturated aqueous sodium chloride solution and then dried with anhydrous sodium sulfate.

The dried organic solution was stripped of the solvent under reduced pressure, and the residue was treated by silica gel column chromatography (developing solvent: hexane) to obtain colorless oily 2-allyloxy-1-bromo-3,5-dimethylbenzene (85.73 g, yield 81%).

$^1$H NMR (CDCl$_3$) δ2.24 (s, 3H), 2.27 (s, 3H), 4.40 (dt, 2H, J=1, 6 Hz), 5.27 (dq, 1H, J=1, 10 Hz), 5.43 (dq, 1H, J=2, 17 Hz), 6.13 (ddt, 1H, J=6, 10, 17 Hz), 6.91 (dd, 1H, J=1, 1 Hz), 7.19 (dd, 1H, J=1, 1 Hz)

EXAMPLE 47

Synthesis of (2-allyloxy-3,5-dimethylphenyl)-dimethyl(2,3,4,5-tetramethylcyclopentadienyl)silane To a tetrahydrofuran solution (200 ml) of 2-allyloxy-1-bromo-3,5-dimethylbenzene (24.10 g) was added dropwise at −78° C. a 1.66 M hexane solution (60.24 ml) of n-butyllithium, and the mixture was stirred for 20 minutes.

The mixture obtained above was added dropwise at a temperature lower than −20° C. over 30 minutes to a solution at −78° C. of dichlorodimethylsilane (100.0 g) dissolved in hexane (100 ml). The resulting mixture was then brought up to room temperature, further stirred for one hour, and the solvent and the excess of dichlorodimethylsilane were distilled off under reduced pressure.

The mixture obtained was dissolved in tetrahydrofuran (200 ml). To the solution was added dropwise at −78° C. a solution of tetramethylcyclopentadienyllithium prepared from a tetrahydrofuran solution (400 ml) of tetramethylcyclopentadiene (12.22 g) and a 1.66 M hexane solution (60.24 ml) of n-butyllithium, the resulting mixture was brought up to room temperature over 2 hours and then stirred for 12 hours.

The reaction mixture was mixed with an aqueous ammonium chloride solution and separated into an aqueous layer and an organic layer. The aqueous layer was treated with hexane to extract hexane solubles therefrom, and the hexane solution obtained and the above-mentioned organic layer were combined to obtain an organic solution. The organic solution was washed with saturated aqueous sodium chloride solution and then dried with anhydrous sodium sulfate.

The dried organic solution was stripped of the solvent under reduced pressure, and the residue was treated by silica gel column chromatography (developing solvent: hexane) to obtain colorless oily (2-allyloxy-3,5-dimethylphenyl)dimethyl(2,3,4,5-tetramethylcyclopentadienyl)silane (18.8 g, yield 56%).

$^1$H NMR (CDCl$_3$) δ0.10 (s, 6H), 1.70 (s, 6H), 1.80 (s, 6H), 2.27 (s, 3H), 2.28 (s, 3H), 3.40 (s, 1H), 4.41 (dt, 2H, J=2, 5 Hz), 5.28 (dq, 1H, J=2, 11 Hz), 5.41 (dq, 1H, J=2, 17 Hz), 6.12 (ddt, 1H, J=5, 11, 17 Hz), 6.94 (d, 1H, J=2 Hz), 7.02 (d, 1H, J=2 Hz)

Mass spectra (EI, m/e) 340, 299, 219, 178, 41

EXAMPLE 48

Synthesis of 2-allyloxy-1-bromo-3-tert-butyl-5-methylbenzene

To a solution at 0° C. of 2-bromo-4-methyl-6-tert-butylphenol (43.8 g) dissolved in acetonitrile (250 ml) was added potassium hydroxide (13.2 g), and the mixture was stirred for 2 hours to obtain a blue solution. Allyl bromide (65 g) was added dropwise at a temperature not higher than 10° C. to the blue solution, the resulting mixture was brought up to room temperature and then stirred for 6 hours.

The reaction mixture was mixed with an aqueous ammonium chloride solution and separated into an aqueous layer and an organic layer. The aqueous layer was treated with hexane to extract hexane solubles therefrom, and the hexane solution obtained and the above-mentioned organic layer were combined to obtain an organic solution. The organic solution was washed with saturated aqueous sodium chloride solution and then dried with anhydrous sodium sulfate.

The dried organic solution was stripped of the solvent under reduced pressure, and the residue was treated by silica gel column chromatography (developing solvent: hexane) to obtain colorless oily 2-allyloxy-1-bromo-3-tert-butyl-5-methylbenzene (46.07 g, yield 90%).

$^1$H NMR (CDCl$_3$) δ1.38 (s, 9H), 2.27 (s, 3H), 4.57 (dt, 2H, J=2, 5 Hz), 5.29 (dq, 1H, J=2, 11 Hz), 5.49 (dq, 1H, J=2, 17 Hz), 6.13 (ddt, 1H, J=5, 11, 17 Hz), 7.07 (d, 1H, J=2 Hz), 7.25 (d, 1H, J=2 Hz)

EXAMPLE 49

Synthesis of 2-allyloxy-1-bromo-3-tert-butyl-5-methylbenzene

To a mixture of 85% potassium hydroxide (76.61 g) and methyl isobutyl ketone (1000 ml) was added at 10° C. over 2 hours 2-bromo-6-tert-butyl-4-methylphenol (230.98 g), and the resulting mixture was then stirred at 25° C. for one hour. To the resulting deep blue mixture was added at 10° C. allyl bromide (133.07 g), and the mixture obtained was stirred at 25° C. for 12 hours.

The reaction mixture was mixed with water (500 ml) and separated into an aqueous layer and an organic layer. The organic layer was washed with saturated aqueous sodium chloride solution and dried with anhydrous sodium sulfate. The solvent was distilled off under reduced pressure from the dried organic layer and the residue was distilled to obtain a colorless oil of 2-allyloxy-1-bromo-3-tert-butyl-5-methylbenzene (245.25 g, yield 91%).

Boiling point 74–75° C. (0.08 mmHg)

$^1$H NMR (CDCl$_3$) δ1.38 (s, 9H), 2.27 (s, 3H), 4.57 (dt, 2H, J=2, 5 Hz), 5.29 (dq, 1H, J=2, 11 Hz), 5.49 (dq, 1H, J=2, 17 Hz), 6.13 (ddt, 1H, J=5, 11, 17 Hz), 7.07 (d, 1H, J=2 Hz), 7.25 (d, 1H, J=2 Hz)

Mass spectra (EI, M/e) 282, 269, 241, 226, 203, 162, 147, 122, 91, 41

EXAMPLE 50

Synthesis of 2-allyloxy-1-bromo-3-tert-butyl-5-methylbenzene

To a mixture (30 ml) of 85% potassium hydroxide (1.82 g), tetra-n-butylammonium bromide (0.040 g) and toluene were added dropwise at 50° C. with stirring 2-bromo-6-t-butyl-4-methylphenol (6.08 g) and allyl bromide (3.38 g). Then the resulting mixture was stirred at 50° C. for 3 hours.

After being cooled to 25° C., the reaction mixture was mixed with water and separated into an aqueous layer and an organic layer. The organic layer was washed with saturated aqueous sodium chloride solution and then dried with anhydrous sodium sulfate. Gas chromatographic analysis using the internal standard method revealed that 2-allyloxy-1-bromo-3-tert-butyl-5-methylbenzene had been formed in 93% yield based on the 2-bromo-6-t-butyl-4-methylphenol used.

EXAMPLE 51

Synthesis of 2-allyloxy-1-bromo-3-tert-butyl-5-methoxybenzene

To a mixture of 85% potassium hydroxide (4.57 g) and methyl isobutyl ketone (30 ml) was added at 10° C.

2-bromo-6-tert-butyl-4-methoxyphenol (16.02 g), and the resulting mixture was stirred at 25° C. for 1 hour. To the deep blue solution thus obtained was added at 10° C. allyl bromide (8.47 g), and the mixture was then stirred at 25° C. for 12 hours.

The reaction mixture was mixed with water and separated into an aqueous layer and an organic layer. The organic layer obtained was washed with saturated aqueous sodium chloride solution and then dried with anhydrous sodium sulfate. The dried organic layer was stripped of the solvent under reduced pressure, and the residue was distilled to obtain pale yellow oily 2-allyloxy-1-bromo-3-tert-butyl-5-methoxybenzene (15.80 g yield 85%).

B.p. 115–117° C. (0.8 mmHg)

$^1$H NMR (CDCl$_3$) δ1.38 (s, 9H), 3.76 (s, 3H), 4.55 (dt, 2H, J=2, 5 Hz), 5.29 (dq, 1H, J=2, 11 Hz), 5.48 (dq, 1H, J=2, 17 Hz), 6.13 (ddt, 1H, J=5, 9, 17 Hz), 6.86 (d, 1H, J=3 Hz), 6.95 (d, 1H, J=3 Hz)

Mass spectra (EI, m/e) 300, 257, 178, 138, 91, 44

EXAMPLE 52

Synthesis of (2-allyloxy-3-tert-butyl-5-methoxyphenyl)dimethyl(2,3,4,5-tetramethyl-cyclopentadienyl)silane To a hexane solution (90 ml) of 2-allyloxy-1-bromo-3-tert-butyl-5-methoxybenzene (8.98 g) was added dropwise at −78° C. a 1.66 M hexane solution (18.07 ml) of n-butyllithium, the resulting mixture was brought up to −30° C. and stirred for one hour. The mixture obtained was cooled to −78° C., then dichlorodimethylsilane (4.26 g) was added thereto, the resulting mixture was brought up to 25° C. over 2 hours, and further stirred for 3 hours. Thereafter, the solvent and the excess of dichlorodimethylsilane were distilled off under reduced pressure.

The mixture thus obtained was dissolved in tetrahydrofuran (50 ml), the resulting solution was added dropwise at −78° C. to a tetrahydrofuran solution (100 ml) of tetramethylcyclopentadienyllithium (3.84 g). The resulting mixture was brought up to room temperature over 2 hours and then stirred for 12 hours.

The reaction mixture was mixed with an aqueous ammonium chloride solution and separated into an aqueous layer and an organic layer. The aqueous layer was treated with hexane to extract hexane solubles therefrom, and the hexane solution obtained and the above-mentioned organic layer were combined to obtain an organic solution. The organic solution was washed with saturated aqueous sodium chloride solution and then dried with anhydrous sodium sulfate.

The dried organic solution was stripped of the solvent under reduced pressure, and the residue was treated by silica gel column chromatography (developing solvent: hexane) to obtain colorless oily (2-allyloxy-3-tert-butyl-5-methoxyphenyl)dimethyl(2,3,4,5-tetramethylcyclopentadienyl)silane (5.00 g, yield 42%).

$^1$H NMR (CDCl$_3$) δ0.14 (s, 6H), 1.39 (s, 9H), 1.70 (s, 6H), 1.78 (s, 6H), 3.42 (s, 1H), 3.80 (s, 3H), 4.39 (dt, 2H, J=2, 2 Hz), 5.27 (dq, 1H, J=2, 11 Hz), 5.53 (dq, 1H, J=2, 17 Hz), 6.03 (ddt, 1H, J=2, 11, 17 Hz), 6.75 (d, 1H, J=3 Hz), 6.93 (d, 1H, J=3 Hz)

Mass spectra (EI, m/e) 399, 261, 236, 221, 162, 147, 75

EXAMPLE 53

Synthesis of dimethylsilyl (tetramethylcyclopentadienyl)(3-tert-butyl-5-methyl-2-phenoxy)titanium dichloride To a hexane solution (1170 ml) of (3-tert-butyl-2-allyloxy-5-methylphenyl)dimethyl(2,3,4,5-tetramethylcyclopentadienyl)silane (117.5 g, purity 85%) was added dropwise at room temperature a 1.66 M hexane solution (340 ml) of n-butyllithium, and the mixture was stirred for 12 hours. The supernatant of the reaction liquid was removed, and then toluene (1400 ml) and titanium tetrachloride (61 g) were added at room temperature to the remainder of the reaction liquid, and the resulting mixture was stirred at 95° C. for 10 hours while being shielded from light.

The reaction mixture was filtered, and the solid was washed with toluene (500 ml). The filtrate and the washings obtained were combined, and the solvent was distilled off to obtain a reddish black tar. Toluene (250 ml) and hexane (1150 ml) were added to the tar, the resulting mixture was heated to 65° C. to form a solution, which was then allowed to stand at −20° C. for 24 hours. The precipitate formed was collected by filtration, washed with hexane (80 ml) and dried under reduced pressure to obtain a red solid. The solid was recrystallized from a solvent mixture of toluene (240 ml) and hexane (720 ml) to obtain a red needle-like crystals of dimethylsilyl(tetramethylcyclopentadienyl)(3-tert-butyl-5-methyl-2-phenoxy)titanium dichloride (29.1 g, yield 22.6%).

EXAMPLE 54

Synthesis of (3,5-di-tert-butyl-2-trimethylsiloxyphenyl)chlorodimethylsilane

To a solution at −70° C. of 1-bromo-3,5-di-tert-butyl-2-trimethylsiloxybenzene (39.0 g) dissolved in tetrahydrofuran (100 ml) was added dropwise a 1.68 M hexane solution (71.4 ml) of n-butyllithium, and the mixture was stirred at −70° C. for 2 hours.

The mixture obtained above was added dropwise to a solution at −70° C. of dichlorodimethylsilane (66.1 ml) dissolved in tetrahydrofuran (70 ml), and the resulting mixture was brought up to room temperature over 2 hours.

The reaction mixture was stripped of the solvent, and the residue was treated with hexane (70 ml) to extract hexane solubles therefrom. The solvent was distilled off from the hexane solution thus obtained to obtain pale yellow (3,5-di-tert-butyl-2-trimethylsiloxyphenyl)chlorodimethylsilane (40.0 g, yield 99%).

$^1$H NMR (CDCl$_3$) δ0.34 (s, 9H), 0.60 (s, 6H), 1.28 (s, 9H), 1.41 (s, 9H), 7.25 (d, J=2.6 Hz, 1H), 7.38 (d, J=2.6 Hz, 1H)

Mass spectra (EI, m/e) 370, 355, 313, 247, 167

EXAMPLE 55

Synthesis of (3,5-di-tert-butyl-2-trimethylsiloxyphenyl) cyclopentadienyldimethylsilane To a tetrahydrofuran solution (100 ml) at −70° C. of cyclopentadienyllithium (2.20 g) was added dropwise a tetrahydrofuran solution (50 ml) of (3,5-di-tert-butyl-2-trimethylsiloxyphenyl)chlorodimethylsilane (9.83 g). Thereafter the resulting mixture was brought up to room temperature over 2 hours and then stirred at room temperature for 12 hours.

The reaction mixture was stripped of the solvent and the residue was treated with hexane to extract hexane solubles therefrom. The hexane solution obtained was stripped of the solvent to obtain pale yellow (3,5-di-tert-butyl-2-trimethylsiloxyphenyl)cyclopentadienyldimethylsilane (10.43 g, yield 98%).

$^1$H NMR (CDCl$_3$) δ0.28 (s, 6H), 0.35 (s, 9H), 1.29 (s, 9H), 1.42 (s, 9H), 6.57 (s, 1H), 7.22 (s, 1H), 7.24 (s, 2H), 7.34 (s, 1H), 7.39 (s, 2H)

Mass spectra (EI, m/e) 400, 385, 326, 311, 298, 247, 215

EXAMPLE 56

Synthesis of (3,5-di-tert-butyl-2-trimethylsiloxyphenyl)dimethyl(trimethylsilylcyclopentadienyl)silane To a tetrahydrofuran solution (20 ml) at −70° C. of (trimethylsilylcyclopentadienyl)lithium (0.85 g) was added dropwise a tetrahydrofuran solution (15 ml) of (3,5-di-tert-butyl-2-trimethylsiloxyphenyl)chlorodimethylsilane (1.86 g). Thereafter the resulting mixture was brought up to room temperature over 2 hours and then stirred at room temperature for 12 hours.

The reaction mixture was stripped of the solvent and the residue was treated with hexane to extract hexane solubles therefrom. The hexane solution was stripped of the solvent to obtain pale yellow oily (3,5-di-tert-butyl-2-trimethylsiloxyphenyl)dimethyl(trimethylsilylcyclopentadienyl)silane (2.0 g, yield 84%).

$^1$H NMR (CDCl$_3$) δ0.11 (s, 9H), 0.30 (s, 9H), 0.37 (s, 6H), 1.31 (s, 9H), 1.33 (s, 9H), 6.45 (m, 1H), 7.25 (s, 1H), 7.28 (m, 2H), 7.37 (s, 1H), 7.41 (s, 1H)

Mass spectra (EI, m/e) 472, 457, 417, 397, 382, 369, 327, 310, 147, 73

EXAMPLE 57

Synthesis of (3-tert-butyl-5-methyl-2-trimethylsiloxyphenyl)chlorodimethylsilane To a mixture at −60° C. consisting of 1-bromo-3-tert-butyl-5-methyl-2-trimethylsiloxybenzene (24.18 g) and tetrahydrofuran (180 ml) was added dropwise a 1.6 M hexane solution (54.2 ml) of n-butyllithium over 30 minutes, and the resulting mixture was then kept at −40° C. for 3.75 hours.

The mixture obtained above was added dropwise to a solution at −60° C. consisting of dichlorodimethylsilane (49.5 g) and tetrahydrofuran (180 ml). The resulting solution was brought up to room temperature over 2 hours, further stirred for 15 hours, and then the solvent and the excess of dichlorodimethylsilane were distilled off under reduced pressure.

The mixture obtained above was treated with hexane to extract hexane solubles therefrom. The hexane solution obtained was stripped of the solvent under reduced pressure to obtain white powder of (3-tert-butyl-5-methyl-2-trimethylsiloxyphenyl)chlorodimethylsilane (24.7 g, yield 98%).

$^1$H NMR (CDCl$_3$) δ0.35 (s, 9H), 0.62 (s, 6H), 1.42 (s, 9H), 2.28 (s, 3H), 7.06 (s, 1H), 7.19 (s, 1H)

Mass spectra (EI, m/e) 328, 313, 271, 205, 167, 93, 73

EXAMPLE 58

Synthesis of (3-tert-butyl-5-methyl-2-trimethylsiloxyphenyl)dimethyl(trimethylsilylcyclopentadienyl)silane To a tetrahydrofuran solution (20 ml) of (trimethylsilylcyclopentadienyl)lithium (1.43 g) was added dropwise at −70° C. a solution containing (3-tert-butyl-5-methyl-2-trimethylsiloxyphenyl)chlorodimethylsilane (2.59 g) and tetrahydrofuran (15 ml), then the resulting mixture was brought up to room temperature over 2 hours and further stirred for 12 hours.

The reaction mixture was stripped of the solvent under reduced pressure, and the residue was treated with hexane to extract hexane solubles therefrom. The hexane solution obtained was stripped of the solvent to obtain pale yellow oily (3-tert-butyl-5-methyl-2-trimethylsiloxyphenyl)dimethyl(trimethylsilylcyclopentadienyl)silane (2.9 g, yield 86%).

$^1$H NMR (CDCl$_3$) δ0.14 (s, 9H), 0.25 (s, 9H), 0.34 (s, 6H), 1.28 (s, 9H), 1.42 (s, 3H), 6.45 (s, 1H), 7.23 (s, 1H), 7.25 (s, 2H), 7.34 (s, 1H), 7.39 (s, 1H)

Mass spectra (CI, m/e) 430

EXAMPLE 59

Synthesis of (3-tert-butyl-2-methoxy-5-methylphenyl)dimethyl(cyclopentadienyl)silane Into a solution consisting of (3-tert-butyl-2-methoxy-5-methylphenyl)chlorodimethylsilane (5.0 g), tetrahydrofuran (35 ml) and hexane (35 ml) was added at −35° C. cyclopentadienyllithium (1.45 g). The resulting mixture was brought up to room temperature over 2 hours and further stirred at room temperature for 10 hours.

From the resulting white suspension, the solvent was distilled off under reduced pressure, and the residue obtained was treated with hexane to extract hexane solubles therefrom. The hexane solution obtained was stripped of the solvent under reduced pressure to obtain yellow oily (3-tert-butyl-2-methoxy-5-methylphenyl)dimethyl(cyclopentadienyl)silane (5.07 g, yield 91%).

$^1$H NMR (CDCl$_3$) δ0.22 (s, 6H), 1.35 (s, 9H), 2.26 (s, 3H), 3.56 (s, 3H), 5.25 (s, 1H), 5.84 (br, 1H), 5.87 (br, 1H), 6.99 (br, 2H), 7.08 (s, 1H), 7.16 (s, 1H)

Mass spectra (EI, m/e) 300, 255, 205, 179, 161, 89

EXAMPLE 60

Synthesis of (3-tert-butyl-5-methyl-2-trimethylsiloxyphenyl)dimethyl(cyclopentadienyl)silane A solution consisting of (3-tert-butyl-5-methyl-2-trimethylsiloxyphenyl)chlorodimethylsilane (2.5 g) and tetrahydrofuran (10 ml) was added dropwise at −40° C. into a solution consisting of cyclopentadienyllithium (0.56 g) and tetrahydrofuran (20 ml). The resulting mixture was brought up to room temperature over 2 hours and further stirred at room temperature for 10 hours.

The reaction mixture was stripped of the solvent under reduced pressure, and the residue was treated with hexane to extract hexane solubles therefrom. The hexane solution obtained was stripped of the solvent under reduced pressure to obtain pale yellow oily (3-tert-butyl-5-methyl-2-trimethylsiloxyphenyl)dimethyl(cyclopentadienyl)silane (2.5 g, yield 92%).

Mass spectra (EI, m/e) 358, 284, 269, 213, 205, 147, 95, 73

EXAMPLE 61

Synthesis of (3-tert-butyl-5-methyl-2-trimethylsiloxyphenyl)dimethyl(2,3,4,5-tetramethylcyclopentadienyl)silane Into a solution consisting of 1-bromo-3-tert-butyl-5-methyl-2-trimethylsiloxybenzene (1.54 g) and tetrahydrofuran (15 ml) was added dropwise at −55° C. over 10 minutes a 1.6 M hexane solution (3.15 ml) of n-butyllithium. The resulting mixture was kept at −45° C. for 45 minutes, then a solution consisting of chlorodimethyl (tetramethylcycopentadienyl)silane (1.0 g) and tetrahydrofuran (5 ml) was added dropwise thereinto, and the reaction mixture was brought up to room temperature over 2 hours. The reaction mixture was stirred at room temperature for 13 days and then stripped of the solvent under reduced pressure.

The mixture thus obtained was treated with hexane to extract hexane solubles therefrom. The hexane solution obtained was allowed to stand at −40° C. overnight and the white solid thus formed was dried to obtain pale yellow oily (3-tert-butyl-5-methyl-2-trimethylsiloxyphenyl)dimethyl(2,3,4,5-tetramethylcyclopentadienyl)silane (0.97 g, yield 48%).

$^1$H NMR (CDCl$_3$) δ0.01 (s, 6H), 0.42 (s, 9H), 1.50 (s, 9H), 2.01 (s, 6H), 2.10 (s, 6H), 2.33 (s, 3H), 3.59 (s, 1H), 7.11 (s, 1H), 7.23 (s, 1H)

EXAMPLE 62

Synthesis of (3-tert-butyl-2-methoxy-5-methyphenyl)chlorodimethylsilane

To a solution consisting of tetrahydrofuran (31.5 ml), hexane (139 ml) and 3-tert-butyl-1-bromo-2-methoxy-5-methylbenzene (45 g) was added dropwise at −40° C. over 20 minutes a 1.6 M hexane solution (115 ml) of n-butyllithium. The resulting mixture was kept at −40° C. for one hour, and then tetrahydrofuran (31.5 ml) was added dropwise thereto.

The mixture obtained above was added dropwise at −40° C. into a solution consisting of dichlorodimethylsilane (131 g) and hexane (306 ml). The resulting mixture was brought up to room temperature over 2 hours and further stirred for 12 hours.

The solvent and the excess of dichlorodimethylsilane were distilled off under reduced pressure from the reaction mixture, and the residue was treated with hexane to extract hexane solubles therefrom. The hexane solution obtained was stripped of the solvent to obtain pale yellow oily (3-tert-butyl-2-methoxy-5-methylphenyl) chlorodimethylsilane (41.9 g, yield 84%).

$^1$H NMR (CDCl$_3$) δ0.68 (s, 6H), 1.32 (s, 9H), 2.23 (s, 3H), 3.70 (s, 3H), 7.20 (s, 1H), 7.21 (s, 1H)

Mass spectra (EI, m/e) 270, 255, 219, 189, 145, 128, 109, 93

EXAMPLE 63

Synthesis of (3-tert-butyl-2-methoxy-5-methylphenyl)dimethyl(2,3,4,5-tetramethylcyclopentadienyl)silane Into a solution consisting of (3-tert-butyl-2-methoxy-5-methylphenyl)chlorodimethylsilane (5.24 g) and tetrahydrofuran (50 ml) was added at −35° C. tetramethylcyclopentadienyllithium (2.73 g), the resulting mixture was brought up to room temperature over 2 hours and further stirred at room temperature for 10 hours.

The reaction mixture obtained was stripped of the solvent under reduced pressure, and the residue was treated with hexane to extract hexane solubles therefrom. The hexane solution obtained was stripped of the solvent under reduced pressure to obtain yellow oily (3-tert-butyl-2-methoxy-5-methylphenyl)dimethyl(2,3,4,5-tetramethylcyclopentadienyl)silane (6.69 g, yield 97%).

$^1$H NMR (C$_6$D$_6$) δ0.31 (s, 6H), 1.49 (s, 9H), 1.81 (s, 6H), 1.89 (s, 6H), 2.22 (s, 3H), 3.60 (s, 3H), 5.23 (s, 3H), 7.23 (br, 2H)

Mass spectra (EI, m/e) 356, 299, 235, 205, 179, 161, 89

EXAMPLE 64

Synthesis of dimethylsilyl (tetramethylcyclopentadienyl)(3-tert-butyl-5-methyl-2-phenoxy)titanium dichloride To a solution consisting of (3-tert-butyl-2-methoxy-5-methyl-phenyl)dimethyl(2,3,4,5-tetramethylcyclopentadienyl)silane (10.04 g), toluene (100 ml) and triethylamine (6.30 g) was added dropwise at −70° C. a 1.63 M hexane solution (19.0 ml) of n-butyllithium, the resulting mixture was then brought up to room temperature over 2 hours and further kept at room temperature for 12 hours.

Under nitrogen atmosphere at 0° C., the mixture obtained above was added dropwise to the toluene solution (50 ml) of titanium tetrachloride (4.82 g), the resulting mixture was brought up to room temperature over 1 hour and then heated under reflux for 10 hours.

The reaction mixture was filtered, and the solvent was distilled off from the filtrate. The resulting residue was recrystallized from a toluene-hexane solvent mixture to obtain columnar orange crystals of dimethylsilyl (tetramethylcyclopentadienyl)(3-tert-butyl-5-methyl-2-phenoxy)titanium dichloride having the following structural formula (3.46 g, yield 27%).

$^1$H NMR (CDCl$_3$) δ0.57 (s, 6H), 1.41 (s, 9H), 2.15 (s, 6H), 2.34 (s, 6H), 2.38 (s, 3H), 7.15 (s, 1H), 7.18 (s, 1H)

$^{13}$C NMR (CDCl$_3$) δ1.25, 14.48, 16.28, 22.47, 31.25, 36.29, 120.23, 130.62, 131.47, 133.86, 135.50, 137.37, 140.82, 142.28, 167.74

Mass spectra (CI, m/e) 458

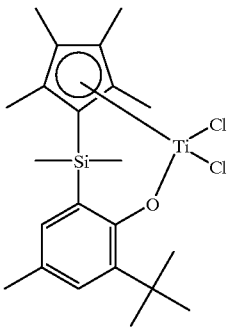

EXAMPLE 65

An autoclave with an inner volume of 3 l fitted with a stirrer was dried under reduced pressure and the inner atmosphere was replaced with argon. Then 1 l of toluene as the solvent and 20 ml of hexene-1 as the α-olefin were placed in the autoclave, and the reactor was brought up to 80° C. After the temperature rise, ethylene was fed into the reactor while the ethylene pressure being controlled at 12 kg/cm$^2$. After the inside of the system had become stable, 1.0 mmol of triisobutylaluminum, then 2.0 μmol of isopropylidene(cyclopentadienyl)(3-tert-butyldimethylsilyl-5-methyl-2-phenoxy)titanium dichloride synthesized in Example 18, and succeedingly 6.0 μmol of triphenylmethyl tetrakis(pentafluorophenyl)borate were successively charged into the reactor. Polymerization was carried out for 30 minutes while controlling the temperature at 80° C.

As the result of polymerization, an ethylene-hexene-1 copolymer having an SCB of 25.0, $[\eta_1]$ of 0.77, molecular weight (Mw) of 35,000, molecular weight distribution (Mw/Mn) of 2.1 and melting point of 94.2° C. was produced at a rate of $2.65 \times 10^7$ g per mol of titanium per hour.

EXAMPLE 66

An autoclave with an inner volume of 0.4 l fitted with a stirrer was dried under reduced pressure and the inner atmosphere was replaced with argon. Then, 198 ml of toluene as the solvent and 2 ml of hexene-1 as the α-olefin were placed in the autoclave, and the reactor was brought up to 60° C. After the temperature rise, ethylene was fed into the reactor while the ethylene pressure being controlled at 6 kg/cm$^2$. After the inside of the system had become stable, 0.25 mmol of triisobutylaluminum, then 1.0 μmol of isopropylidene(cyclopentadienyl)(3,5-dimethyl-2-phenoxy) titanium dichloride synthesized in Example 10, and succeedingly 3.0 μmol of triphenylmethyl tetrakis (pentafluorophenyl)borate were successively charged into the reactor. Polymerization was carried out for 10 minutes while controlling the temperature at 60° C.

As the result of polymerization, an ethylenehexene-1 copolymer having an SCB of 14.7, $[\eta_1]$ of 1.67, molecular weight (Mw) of 120,000, molecular weight distribution (Mw/Mn) of 11.3 and melting point of 110.6° C. was produced at a rate of $2.65 \times 10^7$ g per mol of titanium per hour.

EXAMPLE 67

An autoclave with an inner volume of 0.4 l fitted with a stirrer was dried under reduced pressure, and the inner atmosphere was replaced with argon. Then, 198 ml of toluene as the solvent and 2 ml of hexene-1 as the α-olefin were placed in the autoclave, and the reactor was brought up to 60° C. After the temperature rise, ethylene was fed into the reactor while the ethylene pressure being controlled at 6 kg/cm$^2$. After the inside of the system had become stable, 0.25 mmol of triisobutylaluminum, then 1.0 μmol of isopropylidene(cyclopentadienyl)(3-phenyl-2-phenoxy) titanium dichloride synthesized in Example 12, and succeedingly 3.0 μmol of triphenylmethyl tetrakis (pentafluorophenyl)borate were successively charged into the reactor. Polymerization was carried out for 10 minutes while controlling the temperature at 60° C.

As the result of polymerization, an ethylene-hexene-1 copolymer having an SCB of 18.7, $[\eta_1]$ of 0.62, molecular weight (Mw) of 27,000, molecular weight distribution (Mw/Mn) of 6.7 and melting point of 106.0° C. was produced at a rate of $8.82 \times 10^6$ g per mol of titanium per hour.

EXAMPLE 68

An autoclave with an inner volume of 0.4 l fitted with a stirrer was dried under reduced pressure and the inner atmosphere was replaced with argon. Then, 198 ml of hexane as the solvent and 2 ml of hexene-1 as the α-olefin were placed in the autoclave, and the reactor was brought up to 60° C. After the temperature rise, ethylene was fed into the reactor while the ethylene pressure being controlled at 6 kg/cm$^2$. After the inside of the system had become stable, 0.25 mmol of triisobutylaluminum, then 1.0 μmol of isopropylidene (3-tert-butylcyclopentadienyl)(3-tert-butyl-5-methyl-2-phenoxy)titanium dichloride synthesized in Example 14, and succeedingly 3.0 μmol of triphenylmethyl tetrakis(pentafluorophenyl)borate were successively charged into the reactor. Polymerization was carried out for 10 minutes while controlling the temperature at 60° C.

As the result of polymerization, an ethylene-hexene-1 copolymer having an SCB of 32.0, $[\eta_1]$ of 1.34, molecular weight (Mw) of 69,000, molecular weight distribution (Mw/Mn) of 1.9 and melting point of 82.7° C. was produced at a rate of $1.75 \times 10^7$ g per mol of titanium per hour.

EXAMPLE 69

An autoclave with an inner volume of 0.4 l fitted with a stirrer was dried under reduced pressure and the inner atmosphere was replaced with argon. Then, 185 ml of cyclohexane as the solvent and 15 ml of hexene-1 as the α-olefin were placed in the autoclave, and the reactor was brought up to 180° C. After the temperature rise, ethylene was fed into the reactor while the ethylene pressure being controlled at 25 kg/cm$^2$. After the inside of the system had become stable, 0.25 mmol of triisobutylaluminum, then 1.0 μmol of dimethylsilyl(tetramethylcyclopentadienyl)(3-tert-butyl-5-methyl-2-phenoxy)titanium dichloride synthesized in Example 64, and succeedingly 3.0 μmol of N,N-dimethylanilinium tetrakis(pentafluorophenyl)borate as the toluene solution thereof were successively charged into the reactor. Polymerization was carried out for 2 minutes while controlling the temperature at 180° C.

As the result of polymerization, an ethylene-hexene-1 copolymer having an SCB of 33.6, $[\eta_1]$ of 1.03, molecular weight (Mw) of 51,000, molecular weight distribution (Mw/Mn) of 2.0 and melting point of 87.4° C. was produced at a rate of $3.36 \times 10^6$ g per mol of titanium per 2 min.

EXAMPLE 70

An autoclave with an inner volume of 3 l fitted with a stirrer was dried under reduced pressure and the inner atmosphere was replaced with argon. Then, 1 l of hexane as the solvent and 10 ml of hexene-1 as the α-olefin were placed in the autoclave, and the reactor was brought up to 80° C. After the temperature rise, ethylene was fed into the reactor while the ethylene pressure being controlled at 6 kg/cm$^2$. After the inside of the system had become stable, 1.0 mmol of triisobutylaluminum, then 0.5 μmol of isopropylidene(cyclopentadienyl)(3-tert-butyl-5-methyl-2-phenoxy)titanium dichloride synthesized in Example 1(1), and succeedingly 3.0 μmol of N,N-dimethylanilinium tetrakis(pentafluorophenyl)borate were successively charged into the reactor. Polymerization was carried out for 30 minutes while controlling the temperature at 80° C.

As the result of polymerization, an ethylene-hexene-1 copolymer having an SCB of 27.7, $[\eta_1]$ of 0.99, molecular weight (Mw) of 46,000, molecular weight distribution (Mw/Mn) of 1.7 and melting point of 93.4° C. was produced at a rate of $1.60 \times 10^7$ g per mol of titanium per hour.

EXAMPLE 71

An autoclave with an inner volume of 3 l fitted with a stirrer was dried under reduced pressure and the inner atmosphere was replaced with argon. Then, 1 l of hexane as the solvent and 20 ml of hexene-1 as the α-olefin were placed in the autoclave, and the reactor was brought up to 80° C. After the temperature rise, ethylene was fed into the reactor while the ethylene pressure being controlled at 12 kg/cm$^2$. After the inside of the system had become stable, 0.5 mmol of triethylaluminum, then 2.0 µmol of isopropylidene (cyclopentadienyl)(3-tert-butyl-5-methyl-2-phenoxy) titanium dichloride synthesized in Example 1(1), and succeedingly 6.0 µmol of triphenylmethyl tetrakis (pentafluorophenyl)borate were successively charged into the reactor. Polymerization was carried out for 30 minutes while controlling the temperature at 80° C.

As the result of polymerization, an ethylene-hexene-1 copolymer having an SCB of 21.8, [η$_1$] of 1.06, molecular weight (Mw) of 52,000, molecular weight distribution (Mw/Mn) of 1.8 and melting point of 99.5° C. was produced at a rate of 1.52×10$^7$ g per mol of titanium per hour.

EXAMPLE 72

An autoclave with an inner volume of 3 l fitted with a stirrer was dried under reduced pressure and the inner atmosphere was replaced with argon. Then, 1 l of toluene as the solvent and 20 ml of hexene-1 as the α-olefin were placed in the autoclave, and the reactor was brought up to 80° C. After the temperature rise, ethylene was fed into the reactor while the ethylene pressure being controlled at 12 kg/cm$^2$. After the inside of the system had become stable, 12.0 µmol of triphenylmethyl tetrakis(pentafluorophenyl) borate, then 0.5 mmol of triisobutylaluminum, and thereafter 2.0 µmol of isopropylidene(cyclopentadienyl)(3-tert-butyl-5-methyl-2-phenoxy)titanium dichloride synthesized in Example 1(1) which had been precontacted beforehand with 0.5 mmol of truisobutylaluminum for 2 minutes were successively charged into the reactor. Polymerization was carried out for 40 minutes while controlling the temperature at 80° C.

As the result of polymerization, an ethylene-hexene-1 copolymer having an SCB of 25.8, [η$_1$] of 1.18, molecular weight (Mw) of 60,000, molecular weight distribution (Mw/Mn) of 1.9 and melting point of 94.9° C. was produced at a rate of 2.27×10$^7$ g per mol of titanium per hour.

EXAMPLE 73

An autoclave with an inner volume of 3 l fitted with a stirrer was dried under reduced pressure and the inner atmosphere was replaced with argon. Then, 1 l of toluene as the solvent and 20 ml of hexene-1 as the α-olefin were placed in the autoclave, and the reactor was brought up to 80° C. After the temperature rise, ethylene was fed into the reactor while the ethylene pressure being controlled at 12 kg/cm$^2$. After the inside of the system had become stable, 1.0 µmol of triisobutylaluminum, then 2.0 µmol of isopropylidene(cyclopentadienyl) (3-tert-butyl-5-methyl-2-phenoxy)titanium dichloride synthesized in Example 1(1) which had been stored as a hexane solution under nitrogen at room temperature for one month, and succeedingly 6.0 µmol of triphenylmethyl tetrakis (pentafluorophenyl)borate were successively charged into the reactor. Polymerization was carried out for 30 minutes while controlling the temperature at 80° C.

As the result of polymerization, an ethylene-hexene-1 copolymer having an SCB of 24.8, [η$_1$] of 1.18, molecular weight (Mw) of 61,000, molecular weight distribution (Mw/Mn) of 1.9 and melting point of 96.3° C. was produced at a rate of 3.51×10$^7$ g per mol of titanium per hour.

EXAMPLE 74

An autoclave with an inner volume of 3 l fitted with a stirrer was dried under reduced pressure and the inner atmosphere was replaced with argon. Then, 1 l of toluene as the solvent and 20 ml of hexene-1 as the α-olefin were placed in the autoclave, and the reactor was brought up to 80° C. After the temperature rise, ethylene was fed into the reactor while the ethylene pressure being controlled at 12 kg/cm$^2$. After the inside of the system had become stable, 1.0 mmol of triisobutylaluminum, then 2.0 µmol of isopropylidene(cyclopentadienyl)(3-tert-butyl-5-methyl-2-phenoxy)titanium dichloride synthesized in Example 1(1), and succeedingly 1.0 µmol of triphenylmethyl tetrakis (pentafluorophenyl)borate were successively charged into the reactor. Polymerization was carried out for 30 minutes while controlling the temperature at 80° C.

As the result of polymerization, an ethylene-hexene-1 copolymer having an SCB of 23.3, [η$_1$] of 1.24, molecular weight (Mw) of 67,000, molecular weight distribution (Mw/Mn) of 1.7 and melting point of 96.7° C. was produced at a rate of 2.00×10$^7$ g per mol of titanium per hour.

EXAMPLE 75

An autoclave with an inner volume of 3 l fitted with a stirrer was dried under reduced pressure and the inner atmosphere was replaced with argon. Then, 1 l of toluene as the solvent and 20 ml of hexene-1 as the α-olefin were placed in the autoclave, and the reactor was brought up to 40° C. After the temperature rise, ethylene was fed into the reactor while the ethylene pressure being controlled at 12 kg/cm$^2$. After the inside of the system had become stable, 1.0 mmol of triisobutylaluminum, then 2.0 µmol of isopropylidene(cyclopentadienyl)(3-tert-butyl-5-methyl-2-phenoxy)titanium dichloride synthesized in Example 1(1), and succeedingly 6.0 µmol of triphenylmethyl tetrakis (pentafluorophenyl)borate were successively charged into the reactor. Polymerization was carried out for 10 minutes while controlling the temperature at 40° C.

As the result of polymerization, an ethylene-hexene-1 copolymer having an SCB of 14.8, [η$_1$] of 1.93, molecular weight (Mw) of 110,000, molecular weight distribution (Mw/Mn) of 2.1 and melting point of 103.8° C. was produced at a rate of 1.27×108 g per mol of titanium per hour.

EXAMPLE 76

An autoclave with an inner volume of 3 l fitted with a stirrer was dried under reduced pressure and the inner atmosphere was replaced with argon. Then, 1 l of hexane as the solvent and 10 ml of hexene-1 as the α-olefin were placed in the autoclave, hydrogen was added thereinto to a hydrogen pressure of 100 mmHg, and the reactor was brought up to 80° C. After the temperature rise, ethylene was fed into the reactor while the ethylene pressure being controlled at 6 kg/cm$^2$. After the inside of the system had become stable, 1.0 mmol of tri-isobutylaluminum, then 2.0 µmol of dimethylsilyl(tetramethylcyclopentadienyl)(3-tert-butyl-5-methyl-2-phenoxy)titanium dichloride synthesized in Example 64, and succeedingly 3.0 µmol of N,N-dimethylanilinium tetrakis(pentafluorophenyl)borate were successively charged into the reactor. Polymerization was carried out for 30 minutes while controlling the temperature at 80° C.

As the result of polymerization, an ethylene-hexene-1 copolymer having an SCB of 27.2, [η$_1$] of 1.69, molecular weight (Mw) of 99,000, molecular weight distribution (Mw/Mn) of 1.9 and melting point of 83.1° C. was produced at a rate of 1.50×10$^7$ g per mol of titanium per hour.

EXAMPLE 77

An autoclave with an inner volume of 3 l fitted with a stirrer was dried under reduced pressure and the inner atmosphere was replaced with argon. Then, 1 l of hexane as the solvent and 20 ml of hexene-1 as the α-olefin were placed in the autoclave, hydrogen was added thereinto to a hydrogen pressure of 200 mmHg, and the reactor was brought up to 80° C. After the temperature rise, ethylene was fed into the reactor while the ethylene pressure being controlled at 12 kg/cm². After the inside of the system had become stable, 0.75 mmol of triisobutylaluminum, then 0.5 µmol of dimethylsilyl(tetramethylcyclopentadienyl)(3-tert-butyl-5-methyl-2-phenoxy)titanium dichloride synthesized in Example 64, and succeedingly 1.5 pmol of N,N-dimethylanilinium tetrakis(pentafluorophenyl)borate were successively charged into the reactor. Polymerization was carried out for 30 minutes while controlling the temperature at 80° C.

As the result of polymerization, an ethylene-hexene-1 copolymer having an SCB of 26.8, $[\eta_1]$ of 2.22, molecular weight (Mw) of 140,000, molecular weight distribution (Mw/Mn) of 1.6 and melting point of 85.6° C. was produced at a rate of 2.00×10⁷ g per mol of titanium per hour.

EXAMPLE 78

An autoclave with an inner volume of 3 l fitted with a stirrer was dried under reduced pressure and the inner atmosphere was replaced with argon. Then, 1 l of hexane as the solvent and 20 ml of hexene-1 as the αolefin were placed in the autoclave, hydrogen was added thereinto to a hydrogen pressure of 100 mmHg, and the reactor was brought up to 80° C. After the temperature rise, ethylene was fed into the reactor while the ethylene pressure being controlled at 12 kg/cm². After the inside of the system had become stable, 0.75 mmol of triisobutylaluminum, then 1.0 µmol of dimethylsilyl(tetramethylcyclopentadienyl)(3-tert-butyl-5-methyl-2-phenoxy)titanium dichloride synthesized in Example 64, and succeedingly 2.0 µmol of N,N-dimethylanilinium tetrakis(pentafluorophenyl)borate were successively charged into the reactor. Polymerization was carried out for 30 minutes while controlling the temperature at 80° C.

As the result of polymerization, an ethylene-hexel-1 copolymer having an SCB of 24.7, $[\eta_1]$ of 2.77, molecular weight (Mw) of 170,000, molecular weight distribution (Mw/Mn) of 1.8 and melting point of 87.4° C. was produced at a rate of 3.60×10⁷ g per mol of titanium per hour.

EXAMPLE 79

An autoclave with an inner volume of 3 l fitted with a stirrer was dried under reduced pressure and the inner atmosphere was replaced with argon. Then, 1 l of hexane as the solvent and 10 ml of hexene-1 as the α-olefin were placed in the autoclave, hydrogen was added thereinto to a hydrogen pressure of 100 mmHg, and the reactor was brought up to 80° C. After the temperature rise, ethylene was fed into the reactor while the ethylene pressure being controlled at 6 kg/cm². After the inside of the system had become stable, 1.0 mmol of triisobutylaluminum, then 0.5 µmol of dimethylsilyl(tetramethylcyclopentadienyl)(3-tert-butyl-5-methyl-2-phenoxy)titanium dichloride synthesized in Example 64, and succeedingly 3.0 µmol of triphenylmethyl tetrakis(pentafluorophenyl)borate were successively charged into the reactor. Polymerization was carried out for 30 minutes while controlling the temperature at 80° C.

As the result of polymerization, an ethylene-hexene-1 copolymer having an SCB of 25.2, $[\eta_1]$ of 1.80, molecular weight (Mw) of 110,000, molecular weight distribution (Mw/Mn) of 1.8 and melting point of 84.8° C. was produced at a rate of 4.00×10⁷ g per mol of titanium per hour.

EXAMPLE 80

An autoclave with an inner volume of 3 l fitted with a stirrer was dried under reduced pressure and the inner atmosphere was replaced with argon. Then, 1 l of hexane as the solvent and 20 ml of hexene-1 as the α-olefin were placed in the autoclave, and the reactor was brought up to 80° C. After the temperature rise, ethylene was fed into the reactor while the ethylene pressure being controlled at 12 kg/cm². After the inside of the system had become stable, 1.0 mmol of triisobutylaluminum, then 2.0 µmol of dimethylsilyl(tetramethylcyclopentadienyl)(3-tert-butyl-5-methyl-2-phenoxy)titanium dichloride synthesized in Example 64, and succeedingly 6.0 µmol of triphenylmethyl tetrakis(pentafluorophenyl)borate were successively charged into the reactor. Polymerization was carried out for 30 minutes while controlling the temperature at 80° C.

As the result of polymerization, an ethylene-hexene-1 copolymer having an SCB of 24.5, $[\eta_1]$ of 4.06 and melting point of 84.9° C. was produced at a rate of 3.88×10⁷ g per mol of titanium per hour.

EXAMPLE 81

An autoclave with an inner volume of 3 l fitted with a stirrer was dried under reduced pressure and the inner atmosphere was replaced with argon. Then, 1 l of toluene as the solvent and 20 ml of hexene-1 as the α-olefin were placed in the autoclave, and the reactor was brought up to 80° C. After the temperature rise, ethylene was fed into the reactor while the ethylene pressure being controlled at 12 kg/cm². After the inside of the system had become stable, 1.0 mmol of triethylaluminum, then 2.0 µmol of dimethylsilyl(tetramethylcyclopentadienyl)(3-tert-butyl-5-methyl-2-phenoxy)titanium dichloride synthesized in Example 64, and succeedingly 6.0 µmol of triphenylmethyl tetrakis(pentafluorophenyl)borate were successively charged into the reactor. Polymerization was carried out for 30 minutes while controlling the temperature at 80° C.

As the result of polymerization, an ethylene-hexene-1 copolymer having an SCB of 25.8, $[\eta_1]$ of 2.97 and melting point of 85.9° C. was produced at a rate of 1.87×10⁷ g per mol of titanium per hour.

EXAMPLE 82

An autoclave with an inner volume of 3 l fitted with a stirrer was dried under reduced pressure and the inner atmosphere was replaced with argon. Then, 1 l of toluene as the solvent and 20 ml of hexene-1 as the α-olefin were placed in the autoclave, and the reactor was brought up to 80° C. After the temperature rise, ethylene was fed into the reactor while the ethylene pressure being controlled at 12 kg/cm². After the inside of the system had become stable, 1.0 mmol of triisobutylaluminum, then 1.0 µmol of dimethylsilyl(tetramethylcyclopentadienyl)(3-tert-butyl-5-methyl-2-phenoxy)titanium dichloride synthesized in Example 64, and succeedingly 6.0 µmol of triphenylmethyl tetrakis(pentafluorophenyl)borate were successively charged into the reactor. Polymerization was carried out for 30 minutes while controlling the temperature at 80° C.

As the result of polymerization, an ethylene-hexene-1 copolymer having an SCB of 27.2, $[\eta_1]$ of 4.27 and melting point of 84.1° C. was produced at a rate of 8.70×10⁷ g per mol of titanium per hour.

EXAMPLE 83

An autoclave with an inner volume of 0.4 l fitted with a stirrer was dried under reduced pressure and the inner atmosphere was replaced with argon. Then, 198 ml of toluene as the solvent and 2 ml of hexene-1 as the α-olefin were placed in the autoclave, and the reactor was brought up to 60° C. After the temperature rise, ethylene was fed into the reactor while the ethylene pressure being controlled at 6 kg/cm². After the inside of the system had become stable, 1.0 mmol of methylalumoxane (PMAO, mfd. by Tosoh-Akzo Corp.), then 1.0 μmol of dimethylsilyl(tetramethylcyclopentadienyl)(3-tert-butyl-5-methyl-2-phenoxy)titanium dichloride synthesized in Example 64, and succeedingly 3.0 μmol of triphenylmethyl tetrakis(pentafluorophenyl)borate were successively charged into the reactor. Polymerization was carried out for 10 minutes while controlling the temperature at 60° C.

As the result of polymerization, an ethylene-hexene-1 copolymer having an SCB of 28.3, $[\eta_1]$ of 3.01 and melting point of 80.6° C. was produced at a rate of $2.76 \times 10^7$ g per mol of titanium per hour.

EXAMPLE 84

An autoclave with an inner volume of 0.4 l fitted with a stirrer was dried under reduced pressure and the inner atmosphere was replaced with argon. Then, 198 ml of toluene as the solvent and 2 ml of hexene-1 as the α-olefin were placed in the autoclave, and the reactor was brought up to 60° C. After the temperature rise, ethylene was fed into the reactor while the ethylene pressure being controlled at 6 kg/cm². After the inside of the system had become stable, 0.25 mmol of triisobutylaluminum, then 1.0 μmol of dimethylsilyl(tetramethylcyclopentadienyl)(3-tert-butyl-5-methyl-2-phenoxy)titanium dichloride synthesized in Example 64, and succeedingly 3.0 μmol of tris(pentafluorophenyl)borane were successively charged into the reactor. Polymerization was carried out for 10 minutes while controlling the temperature at 60° C.

As the result of polymerization, an ethylene-hexene-1 copolymer having an SCB of 25.4, $[\eta_1]$ of 4.45 and melting point of 85.2° C. was produced at a rate of $6.48 \times 10^6$ g per mol of titanium per hour.

EXAMPLE 85

An autoclave with an inner volume of 0.4 l fitted with a stirrer was dried under reduced pressure and the inner atmosphere was replaced with argon. Then, 198 ml of hexane as the solvent and 2 ml of hexene-1 as the α-olefin were placed in the autoclave, and the reactor was brought up to 60° C. After the temperature rise, ethylene was fed into the reactor while the ethylene pressure being controlled at 6 kg/cm². After the inside of the system had become stable, 1.0 mmol of methylalumoxane (MMAO type 3A, mfd. by Tosoh-Akzo Corp., toluene solution), then 1.0 μmol of dimethylsilyl(tetramethylcyclopentadienyl)(3-tert-butyl-5-methyl-2-phenoxy)titanium dichloride synthesized in Example 64, and succeedingly 3.0 μmol of triphenylmethyl tetrakis(pentafluorophenyl)borate were successively charged into the reactor. Polymerization was carried out for 10 minutes while controlling the temperature at 60° C.

As the result of polymerization, an ethylene-hexene=1 copolymer having an SCB of 24.7, $[\eta_1]$ of 1.74, molecular weight (Mw) of 100,000, molecular weight distribution (Mw/Mn) of 2.5 and melting point of 93.8° C. was produced at a rate of $1.29 \times 10^7$ g per mol of titanium per hour.

EXAMPLE 86

An autoclave with an inner volume of 0.4 fitted with a stirrer was dried under reduced pressure and the inner atmosphere was replaced with argon. Then, 198 ml of hexane as the solvent and 2 ml of hexene-1 as the α-olefin were placed in the autoclave, and the reactor was brought up to 60° C. After the temperature rise, ethylene was fed into the reactor while the ethylene pressure being controlled at 6 kg/cm². After the inside of the system had become stable, 1.0 mmol of isobutylalumoxane (PBAO mfd. by Tosoh-Akzo Corp.), then 1.0 μmol of dimethylsilyl(tetramethylcyclopentadienyl)(3-tert-butyl-5-methyl-2-phenoxy)titanium dichloride synthesized in Example 64, and succeedingly 3.0 μmol of triphenylmethyl tetrakis(pentafluorophenyl)borate were successively charged into the reactor. Polymerization was carried out for 10 minutes while controlling the temperature at 60° C.

As the result of polymerization, an ethylene-hexene-1 copolymer having an SCB of 35.0, $[\eta_1]$ of 3.51 and melting point of 74.1° C. was produced at a rate of $3.67 \times 10^7$ g per mol of titanium per hour.

EXAMPLE 87

A toluene solution of methylalumoxane (PMAO, mfd. by Tosoh-Akzo Corp.) was stripped of the solvent and dried under reduced pressure. The dried solid methylalumoxane was again dissolved in toluene.

An autoclave with an inner volume of 0.4 l fitted with a stirrer was dried under reduced pressure and the inner atmosphere was replaced with argon. Then, 198 ml of toluene as the solvent and 2 ml of hexene-1 as the α-olefin were placed in the autoclave, and the reactor was brought up to 60° C. After the temperature rise, ethylene was fed into the reactor while the ethylene pressure being controlled at 6 kg/cm². After the inside of the system had become stable, 1.0 mmol of the toluene solution of methylalumoxane obtained by treating, drying and redissolving as described above, then 1.0 μmol of dimethylsilyl(tetramethylcyclopentadienyl)(3-tert-butyl-5-methyl-2-phenoxy)titanium dichloride synthesized in Example 64, and succeedingly 3.0 μmol of triphenylmethyl tetrakis(pentafluorophenyl)borate were successively charged into the reactor. Polymerization was carried out for 10 minutes while controlling the temperature at 60° C.

As the result of polymerization, an ethylene-hexene-1 copolymer having an SCB of 33.8, $[\eta_1]$ of 3.54, and melting point of 75.6° C. was produced at a rate of $3.21 \times 10^7$ g per mol of titanium per hour.

EXAMPLE 88

An autoclave with an inner volume of 0.4 l fitted with a stirrer was dried under reduced pressure and the inner atmosphere was replaced with argon. Then, 198 ml of toluene as the solvent and 2 ml of hexene-1 as the α-olefin were placed in the autoclave, and the reactor was brought up to 60° C. After the temperature rise, ethylene was fed into the reactor while the ethylene pressure being controlled at 6 kg/cm². After the inside of the system had become stable, 0.25 mmol of triisobutylaluminum, then 1.0 μmol of dimethylsilyl(tetramethylcyclopentadienyl)(3-tert-butyl-5-methyl-2-phenoxy)titanium dichloride synthesized in Example 64, and succeedingly 3.0 μmol of N,N-dimethylanilinium tetrakis(pentafluorophenyl)borate were successively charged into the reactor. Polymerization was carried out for 10 minutes while controlling the temperature at 60° C.

As the result of polymerization, an ethylene-hexene-1 copolymer having an SCB of 31.4, $[\eta_1]$ of 4.17 and melting point of 83.0° C. was produced at a rate of $3.56 \times 10^7$ g per mol of titanium per hour.

EXAMPLE 89

An autoclave with an inner volume of 0.4 l fitted with a stirrer was dried under reduced pressure, and the inner atmosphere was replaced with argon. Then, 198 ml of hexane as the solvent and 2 ml of hexene-1 as the α-olefin were placed in the autoclave, and the reactor was brought up to 60° C. After the temperature rise, ethylene was fed into the reactor while the ethylene pressure being controlled at 6 kg/cm$^2$. After the inside of the system had become stable, 0.25 mmol of triisobutylaluminum, then 1.0 µmol of dimethylsilyl(tetramethylcyclopentadienyl)(3-tert-butyl-5-methyl-2-phenoxy)titanium dichloride synthesized in Example 64, and succeedingly 3.0 µmol of N,N-dimethylanilinium tetrakis(pentafluorophenyl)borate were successively charged into the reactor. Polymerization was carried out for 10 minutes while controlling the temperature at 60° C.

As the result of polymerization, an ethylene-hexene-1 copolymer having an SCB of 29.0, $[\eta_1]$ of 3.64 and melting point of 80.9° C. was produced at a rate of 3.18×10$^7$ g per mol of titanium per hour.

EXAMPLE 90

A 2 l glass separable flask fitted with a reflux tube, three dropping funnels, thermometer and monomer blow-in tube was thoroughly flushed with nitrogen, and then 1 l of hexane was placed therein. The feed of ethylene gas and of propylene gas were started through the blow-in tube at a rate of 8 l/min and 2 l/min, respectively. While the inner temperature being controlled at 30° C. with an external water bath jacket and after confirming that the content of the flask had been thoroughly saturated with respective gases, catalyst components were added to the flask from the dropping funnels in the successive order of 0.25 mmol of triisobutylaluminum (1 mmol/ml hexane solution), 0.001 mmol of dimethylsilyl(tetramethylcyclopentadienyl)(3-tert-butyl-5-methyl-2-phenoxy)titanium dichloride synthesized in Example 1(1) dissolved in hexane, and finally 0.005 mmol of triphenylmethyl tetrakis(pentafluorophenyl)borate dissolved in toluene, to initiate polymerization. After the lapse of 30 minutes, 10 ml of ethanol was added to stop polymerization. After the stop of polymerization, the resulting hexane solution containing polymer was concentrated under reduced pressure and then added into 1 l of ethanol solvent, to precipitate the polymer. The precipitated polymer was dried under reduced pressure at 80° C. for twenty-four hours. Resultantly 5.6 g of polymer was obtained. The analysis of the polymer showed that the polymer contained 57.8% by weight of propylene units and 42.2% by weight of ethylene units and had an intrinsic viscosity $[\eta_1]$ of 5.64 dl/g.

EXAMPLE 91

Polymerization was carried out in the same manner as in the polymerization of ethylene and propylene of Example 90 except that 8 mmol of 5-ethylidene-2-norbornene (ENB) was further added. Resultantly, 1.7 g of polymer was obtained. The analysis of the polymer showed that the polymer contained 39.7% by weight of propylene units, 53.5% by weight of ethylene units and 6.75% by weight of ENB units and had an intrinsic viscosity $[\eta_2]$ of 5.64 dl/g.

EXAMPLE 92

Polymerization was carried out in the same manner as in the polymerization of ethylene and propylene of Example 90 except that butene-1 was fed at a rate of 0.06 l/min in place of propylene, and the amounts of dimethylsilyl(tetramethylcyclopentadienyl)(3-tert-butyl-5-methyl-2-phenoxy)titanium dichloride and triphenylmethyl tetrakis(pentafluorophenyl)borate used were changed to 0.0002 mmol and 0.001 mmol, respectively. Resultantly, 1.7 g of polymer was obtained. The analysis of the polymer showed that the polymer contained 9.3% by weight of butene-1 units and 90.7% by weight of ethylene units and had an intrinsic viscosity $[\eta_2]$ of 5.99 dl/g.

EXAMPLE 93

A stainless steel autoclave with an inner volume of 2 l fitted with an electromagnetic stirrer, thermometer and catalyst addition apparatus was thoroughly flushed with nitrogen, and then 800 ml of toluene, 32 g of propylene, 16 mmol of ENB and 50 g of ethylene were charged thereinto. Then the inner temperature was controlled at 60° C. by means of an external warm-water jacket, and after the temperature had become stable, there were added from the catalyst addition apparatus, in the successive order, 0.50 mmol of triisobutylaluminum, 0.001 mmol of dimethylsilyl(tetramethylcyclopentadienyl)(3-tert-butyl-5-methyl-2-phenoxy)titanium dichloride synthesized in Example 1 dissolved in hexane, and finally 0.015 mmol of triphenylmethyl tetrakis(pentafluorophenyl)borate, to initiate polymerization. At the point of time when 1 hour had elapsed after the initiation of polymerization, 10 ml of ethanol was added to stop the polymerization. After the stop of polymerization, unreacted monomers were purged and then a toluene solution containing polymer dissolved therein was recovered. The toluene solution was concentrated by heating, and then about 1 l of ethanol was added thereto to precipitate the polymer. The precipitated polymer was dried in a vacuum dryer for twenty-four hours to obtain 53.2 g of polymer. The analysis of the polymer showed that the polymer had a composition of 30.8% by weight of propylene units, 66.7% by weight of ethylene units and 2.5% by weight of ENB units and had an intrinsic viscosity $[\eta_2]$ of 5.98 dl/g.

EXAMPLE 94

The same procedures as in the polymerization of Example 93 were followed except that ENB was not used and the amount of dimethylsilyl(tetramethylcyclopentadienyl)(3-tert-butyl-5-methyl-2-phenoxy)titanium dichloride was changed to 0.0005 mmol. Resultantly 40.6 g of polymer was obtained. The analysis of the polymer showed that the polymer had a composition of 32.4% by weight of propylene units and 67.6% by weight of ethylene units and had an intrinsic viscosity $[\eta_2]$ of 5.21 dl/g.

EXAMPLE 95

The same procedures as in the polymerization of Example 94 were followed to polymerize ethylene and butene-1 except that 120.0 g of butene-1 was used in place of propylene, the amount of ethylene was changed to 59.0 g, the amount of triphenylmethyl tetrakis(pentafluorophenyl)borate was changed to 0.002 mmol and polymerization was stopped at the point of time when the amount of ethylene absorbed had reached 3.0 g. As the result, 3.45 g of polymer was obtained. The analysis of the polymer showed that the polymer had a composition of 53.5% by weight of butene-1 units and 46.5% by weight of ethylene units, and had an intrinsic viscosity $[72_2]$ of 1.46 dl/g.

EXAMPLE 96

The same procedures as in the polymerization of Example 95 were followed to polymerize ethylene and butene-1 except that the amounts of butene-1, ethylene and triphenylmethyl tetrakis(pentafluorophenyl)borate used were changed to 15.0 g, 43.0 g and 0.003 mmol, respectively, and the polymerization temperature was changed to 80° C. Resultantly, 3.47 g of polymer was obtained. The analysis of the polymer showed that the polymer had a composition of 12.0% by weight of butene-1 units and 88.0% by weight of ethylene units and had an intrinsic viscosity [$\eta_2$] of 3.37 dl/g.

EXAMPLE 97

The same procedures as in the polymerization of Example 95 were followed except that the amounts of ethylene and butene-1 used were changed to 56 g and 56 g, respectively, 8 mmol of ENB was additionally used, and the amounts of dimethylsilyl(tetramethylcyclopentadienyl)(3-tert-butyl-5-methyl-2-phenoxy)titanium dichloride, triphenylmethyl tetrakis(pentafluorophenyl)borate and triisobutylaluminum used were changed to 0.002 mmol, 0.0025 mmol and 1.00 mmol, respectively. Resultantly, 10.65 g of polymer was obtained. The analysis of the polymer showed that the polymer had a composition of 26.7% by weight of butene-1 units, 71.8% by weight of ethylene units and 1.46% by weight of ENB units and had an intrinsic viscosity [$\eta_2$] of 2.08 dl/g.

EXAMPLE 98

A 2 l glass separable flask fitted with a reflux tube, three dropping funnels, thermometer and monomer blow-in tube was thoroughly flushed with nitrogen, and then 1 l of toluene was placed therein. The feed of ethylene gas and of propylene gas were started through the blow-in tube at a rate of 8 l/min and 2 l/min, respectively. While the inner temperature being controlled at 30° C. with an external water bath jacket and after confirming that the content of the flask had been thoroughly saturated with respective gases, catalysts were added to the flask from the dropping funnels in the successive order of 0.10 mmol of triisobutylaluminum (1 mmol/ml hexane solution), 0.002 mmol of isopropylidene (cyclopentadienyl)(3-tert-butyl-5-methyl-2-phenoxy) titanium dichloride synthesized in Example 1(1) dissolved in hexane, and finally 0.010 mmol of triphenylmethyl tetrakis (pentafluorophenyl)borate dissolved in toluene, to initiate polymerization. After the lapse of 30 minutes, 10 ml of ethanol was added to stop polymerization. After the stop of polymerization, the resulting hexane solution containing polymer was concentrated under reduced pressure and then added into 1 l of ethanol solvent to precipitate the polymer. The precipitated polymer was dried under reduced pressure at 80° C. for twenty-four hours. Resultantly, 15.4 g of polymer was obtained. The analysis of the polymer showed that the polymer contained 49.0% by weight of propylene units and 51.0% by weight of ethylene units and had an intrinsic viscosity [$\eta_2$] of 0.50 dl/g.

EXAMPLE 99

The same procedures as in the polymerization of ethylene and propylene of Example 98 were followed except that the feed rate of ethylene was changed to 7 l/min and that of propylene to 1 l/min, and 4 mmol of 5-ethylidene-2-norbornene (ENB) was added. Resultantly, 6.6 g of polymer was obtained. The analysis of the polymer showed that the polymer contained 39.0% by weight of propylene units, 59.3% by weight of ethylene units and 1.75% by weight of ENB units and had an intrinsic viscosity [$\eta_2$] of 1.35 dl/g.

EXAMPLE 100

The same procedures as in the polymerization of ethylene and propylene of Example 98 were followed except that butene-1 was fed at a rate of 0.11 l/min in place of propylene. Resultantly, 4.2 g of polymer was obtained. The analysis of the polymer showed that the polymer contained 9.2% by weight of butene-1 units and 90.8% by weight of ethylene units and had an intrinsic viscosity [$\eta_2$] of 1.70 dl/g.

EXAMPLE 101

The same procedures as in the polymerization of ethylene and butene-1 of Example 100 were followed except that the polymerization temperature was changed to 60° C. and the feed rate of butene-1 to 0.13 l/min. Resultantly, 10.6 g of polymer was obtained. The analysis of the polymer showed that the polymer contained 9.2% by weight of butene-1 units and 90.8% by weight of ethylene units and had an intrinsic viscosity [$\eta_2$] of 1.11 dl/g.

EXAMPLE 102

The same procedures as in the polymerization of ethylene and butene-1 of Example 100 were followed except that trimethylaluminum was used in place of triisobutylaluminum. As the result, 4.8 g of polymer was obtained. The analysis of the polymer showed that the polymer contained 11.4% by weight of butene-1 units and 88.6% by weight of ethylene units and had an intrinsic viscosity [$\eta_2$] of 0.87 dl/g.

Industrial Applicability

As set forth above, according to the present invention, there are provided a complex soluble in saturated hydrocarbon solvents which has a ligand comprising an aromatic ring having a hetero atom in the substituent and a cyclopentadienyl ring linked with each other through a covalent bonding group, and an olefin polymerization catalyst containing the complex which has a high activity at industrially efficient temperatures. Furthermore, by using the catalyst, olefin polymers, particularly linear low density polyethylene, ethylene-α-olefin copolymer rubber and ethylene-α-olefin-non-conjugated diene copolymer rubber, which have a high molecular weight and narrow composition distribution can be produced with good efficiency.

What is claimed is:

1. A transition metal complex represented by the formula (1)

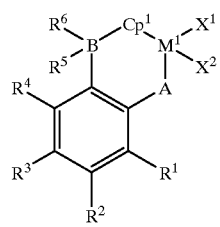

(1)

wherein $M^1$ is a transition metal atom of the group 4 of the periodic table of elements, A is an atom of the group 16 of the periodic table of elements and B is an atom of the group 14 of the periodic table of elements; $Cp^1$ is a group having a cyclopentadiene type anionic skeleton; and $X^1$, $X^2$, $R^1$, $R^2$, $R^3$, $R^4$, $R^5$ and $R^6$ are each independently a hydrogen atom, halogen atom, alkyl group with the number of carbon atoms of 1–20 optionally substituted with at least one halogen atom, aralkyl group with the number of carbon atoms of 7–20 optionally substituted with at least one halogen atom, aryl group with the number of carbon atoms of 6–20 optionally substituted with at least one halogen atom, substituted silyl group with the number of carbon atoms of 1–20 optionally substituted with at least one halogen atom, alkoxy group with the number of carbon atoms of 1–20 optionally substituted with at least one halogen atom, aralkyloxy group with the number of carbon atoms of 7–20 optionally substituted with at least one halogen atom, aryloxy group with the number of carbon atoms of 6–20 optionally substituted with at least one halogen atom, or di-substituted amino group with the number of carbon atoms of 2–20, provided that $R^1$, $R^2$, $R^3$, $R^4$, $R^5$ and $R^6$ may optionally combine with each other to form a ring.

2. The transition metal complex according to claim 1 wherein A in the formula (1) is an oxygen atom.

3. The transition metal complex according to claim 1 wherein $R^1$ in the formula (1) is an alkyl group with the number of carbon atoms of 1–20 optionally substituted with at least one halogen atom, aralkyl group with the number of carbon atoms of 7–20 optionally substituted with at least one halogen atom, aryl group with the number of carbon atoms of 6–20 optionally substituted with at least one halogen atom or substituted silyl group with the number of carbon atoms of 1–20 optionally substituted with at least one halogen atom.

4. The transition metal complex according to claim 1 wherein $X^1$ and $X^2$ in the formula (1) is each independently a halogen atom, alkyl group with the number of carbon atoms of 1–20 optionally substituted with at least one halogen atom, aralkyl group with the number of carbon atoms of 7–20 optionally substituted with at least one halogen atom, or aryl group with the number of carbon atoms of 6–20 optionally substituted with at least one halogen atom.

5. A process for producing the transition metal complex according to claim 1 which comprises reacting a substituted cyclopentadienyl compound represented by the formula (2)

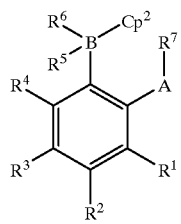

(2)

wherein $Cp^2$ is a group having a cyclopentadiene skeleton, $R^7$ is a hydrocarbon group optionally substituted with at least one halogen atom or a tri-substituted silyl group, and A, B, $R^1$, $R^2$, $R^3$, $R^4$, $R^5$ and $R^6$ are respectively the same as defined above, with a base, and then reacting the resulting reaction product with a transition metal compound represented by the formula (3)

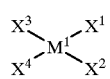

(3)

wherein $X^3$ and $X^4$ are each independently a hydrogen atom, halogen atom, alkyl group with the number of carbon atoms of 1–20 optionally substituted with at least one halogen atom, aralkyl group with the number of carbon atoms of 7–20 optionally substituted with at least one halogen atom, aryl group with the number of carbon atoms of 6–20 optionally substituted with at least one halogen atom, substituted silyl group with the number of carbon atoms of 1–20 optionally substituted with at least one halogen atom, alkoxy group with the number of carbon atoms of 1–20 optionally substituted with at least one halogen atom, aralkyloxy group with the number of carbon atoms of 1–20 optionally substituted with at least one halogen atom, aryloxy group with the number of carbon atoms of 1–20 optionally substituted with at least one halogen atom, or di-substituted amino group with the number of carbon atoms of 2–20, and $M^1$, $X^1$ and $X^2$ are respectively the same as defined above.

6. The process for producing the transition metal complex according to claim 5 wherein the substituted cyclopentadienyl compound represented by the formula (2) is produced by any of the process [I]–[3] described below:

[I] a process which comprises reacting a halogenated aryl compound represented by the formula (9)

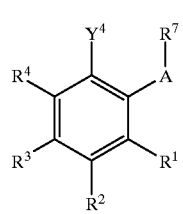

(9)

wherein $Y^4$ is a halogen atom, and A, $R^1$, $R^2$, $R^3$, $R^4$, and $R^7$ are respectively the same as defined above, with an organoalkali metal salt or metallic magnesium, then reacting the reaction product with a cyclopentadienylidene compound represented by the formula (4)

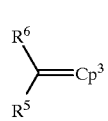

(4)

wherein $Cp^3$ is a group having a cyclopentadienylidene skeleton, and $R^5$ and $R^6$ are respectively the same as defined above, and then reacting the resulting reaction product with water;

[II] a process which comprises reacting the halogenated aryl compound represented by the formula (9) with a dihalide compound represented by the formula (7)

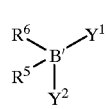

(7)

wherein $Y^1$ and $Y^2$ are each a halogen atom, B' is an atom of group 14 other than carbon atom, and $R^5$ and $R^6$ are respectively the same as defined above, in the presence of an organoalkali metal compound or metallic magnesium. to obtain a halide compound represented by the formula (5)

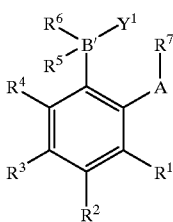
(5)

wherein A, B', $R^1, R^2, R^3, R^4, R^5, R^6, R^7$ and $Y^1$ are respectively the same as defined above, and then reacting the halide compound with a cyclopentadienyl metal salt represented by the formula (6)

$M^2Cp^2$ (6)

wherein $M^2$ is an alkali metal atom, and $Cp^2$ is as defined above;

[III] a process which comprises reacting the halogenated aryl compound represented by the formula (9) with a halide compound represented by the formula (8)

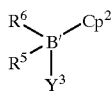
(8)

wherein $Y^3$ is a halogen atom, and B', $Cp^2$, $R^5$ and $R^6$ are respectively the same as defined above, in the presence of an organoalkali metal compound or metallic magnesium.

7. The process for producing the transition metal complex according to claim 6 wherein the halogenated aryl compound represented by the formula (9) is produced by reacting a halogenated aryl compound represented by the formula (10)

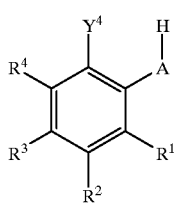
(10)

wherein A, $R^1, R^2, R^3, R^4$ and $Y^4$ are respectively the same as defined above, with a halide represented by the formula (11)

$R^7Y^5$ (11)

wherein $Y^5$ is a halogen atom and $R^7$ is as defined above, in the presence of a base.

8. A substituted cyclopentadienyl compound represented by the formula (2)

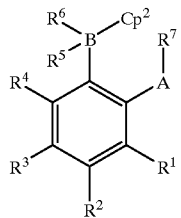
(2)

wherein A represents an atom from group 16 of the periodic table of elements, B represents an atom from group 14 of the periodic table of elements other than a carbon atom, $Cp^2$ represents a group having a cyclonentdiene skeleton, $R^7$ represents a hydrocarbon group optionally substituted with at least one halogen atom or a tri-substituted silyl group, $R^1, R^2, R^3, R^4, R^5$, and $R^6$ are each independently a hydrogen atom, a halogen atom, an alkyl group having 1–20 carbon atoms optionally substituted with at least one halogen atom, an aralkyl group having 7–20 carbon atoms optionally substituted with at least one halogen atom, an aryl group having 6–20 carbon atoms optionally substituted with at least one halogen atom, a substituted silyl group having 1–20 carbon atoms optionally substituted with at least one halogen atom, an alkoxy group having 1–20 carbon atoms optionally substituted with at least one halogen atom, an aralkyloxy group having 7–20 carbon atoms optionally substituted with at least one halogen atom, an aryloxy group having 6–20 carbon atoms optionally substituted with at least one halogen atom, or a di-substituted amino group having 2–20 carbon atoms, provided that $R^1, R^2, R^3, R^4, R^5$, and $R^6$ may optionally combine with each other to form a ring.

9. A process for producing a substituted cyclopentadienyl compound represented by the formula (2a)

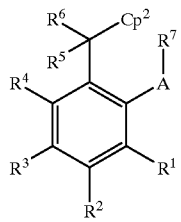
(2a)

wherein wherein $Cp^2$ represents a group having a cyclopentdiene skeleton, A represents an atom from group 16 of the periodic table of elements, $R^1, R^2, R^3, R^4, R^5$, and $R^6$ are each independently a hydrogen atom, a halogen atom, an alkyl group having 1–20 carbon atoms optionally substituted with at least one halogen atom, an aralkyl group having 7–20 carbon atoms optionally substituted with at least one halogen atom, an aryl group having 6–20 carbon atoms optionally substituted with at least one halogen atom, a substituted silyl group having 1–20 carbon atoms optionally substituted with at least one halogen atom, an alkoxy group having 1–20 carbon atoms optionally substituted with at least one halogen atom, an aralkyloxy group having 7–20 carbon atoms optionally substituted with at least one halogen atom, an aryloxy group having 6–20 carbon atoms optionally substituted with at least one halogen atom, or a di-substituted amino group having 2–20 carbon atoms, provided that $R^1$, $R^2$, $R^3$, $R^4$, $R^5$, and $R^6$ may optionally combine with each other to form a ring, and $R^7$ represents a hydrocarbon group optionally substituted with at least one halogen atom or a tri-substituted silyl group, which comprises reacting a halogenated aryl compound represented by the formula (9)

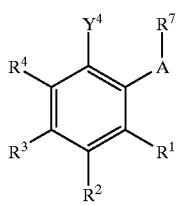
(9)

wherein $Y^4$ is a halogen atom, and A, $R^1$, $R^2$, $R^3$, $R^4$, and $R^7$ are respectively the same as defined above with an organoalkali metal salt or metallic magnesium, then reacting the reaction product with a cyclopentadienylidene compound represented by the formula (4)

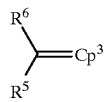
(4)

wherein $Cp^3$ represents a group having a cyclopentadienylidene skeleton, and $R^5$ and $R^6$ are respectively the same as defined above, and
then reacting the resulting reaction product with water.

10. The process for producing a substituted cyclopentadienyl compound according to claim 9, wherein the halogenated aryl compound represented by the formula (9) is produced by reacting a halogenated aryl compound represented by the formula (10)

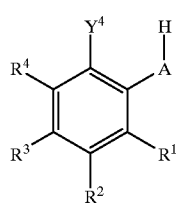
(10)

wherein A, $R^1$, $R^2$, $R^3$, $R^4$, and $Y^4$ are respectively the same as defined above with a halide represented by the formula (11)

$$R^7Y^5 \quad (11)$$

wherein $Y^5$ represents a halogen atom and $R^7$ is as defined above in the presence of a base.

11. A process for producing a substituted cyclopentadienyl compound represented by the formula (2b)

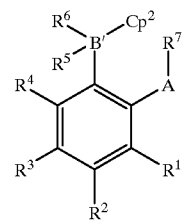
(2b)

wherein $R^1$, $R^2$, $R^3$, $R^4$, $R^5$, and $R^6$ are each independently a hydrogen atom, a halogen atom, an alkyl goup having 1–20 carbon atoms optionally substituted with at least one halogen atom, aralkyl group having 7–20 carbon atoms optionally substituted with at least one halogen atom, an aryl group having 6–20 carbon atoms optionally substituted with at least one halongen atom, a substituted silyl goup having 1–20 carbon atoms optionally substituted with at least one halogen atom, an alkoxy group having 1–20 carbon atoms optionally substituted with at least one halogen atom, an aralkyloxy group having 7–20 carbon atoms optionally substituted with at least one halogen atom, an aryloxy group having 6–20 carbon atoms optionally substituted with at least one halogen atom, or a di-substituted amino goup having 2–20 carbon atoms, provided that $R^1$, $R^2$, $R^3$, $R^4$, $R^5$, and $R^6$ may optionally combine with each other to form a ring, A represents an atom from group 16 of the periodic table of elements, B' represents an element from group 14 of the periodic table of elements other than a carbon atom, $R^7$ represents a hydrocarbon group optionally substituted with at least one halogen atom or a tri-substituted silyl group and $Cp^2$ represents a cyclopentadiene skeleton which comprises reacting a halide compound represented by the formula (5)

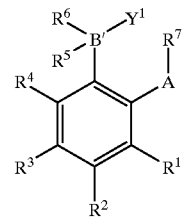
(5)

wherein A, B', $Cp^2$, $R^1$, $R^2$, $R^3$, $R^4$, $R^5$, $R^6$, $R^7$ are respectively the same as defined above, and $Y^1$ represents a halogen atom with a cyclopentadienyl metal salt represented by the formula (6) $M^2Cp^2$ wherein $M^2$ represents an alkali metal atom, and $Cp^2$ is as defined above.

12. The process for producing a substituted cyclopentadienyl compound according to claim 11, wherein the halide compound represented by the formula (5) is produced by reacting a halogenated aryl compound represented by the formula (9)

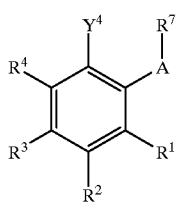
(9)

wherein $Y^4$ is a halogen atom, and A, $R^1$, $R^2$, $R^3$, $R^4$, and $R^7$ are respectively the same as defined above with a dihalide compound represented by the formula (7)

(7)

wherein $Y^1$ is as defined above and $Y^2$ represents a halogen atom, B' is as defined above, and $R^5$ and $R^6$ are respectively the same as defined above in the presence of an organoalkali metal compound or metallic magnesium.

13. The process for producing a substituted cyclopentadienyl compound according to claim 12, wherein the halogenated aryl compound represented by the formula (9) is produced by reacting a halogenated aryl compound represented by the formula (10)

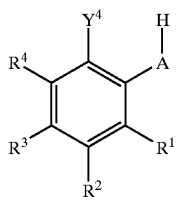
(10)

wherein A, $R^1$, $R^2$, $R^3$, $R^4$, and $Y^4$ are respectively the same as defined above with a halide represented by the formula (11)

$R^7Y^5$ (11)

wherein $Y^5$ represents a halogen atom and $R^7$ is as defined above in the presence of a base.

14. A process for producing a substituted cyclopentadienyl compound represented by the formula (2b)

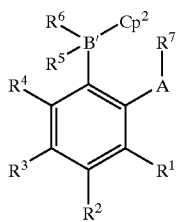
(2b)

wherein $R^1$, $R^2$, $R^3$, $R^4$, $R^5$, and $R^6$ are each independently a hydrogen atom, a halogen atom, an alkyl group having 1–20 carbon atoms optionally substituted with at least one halogen atom, an aralkyl group having 7–20 carbon atoms optionally substituted with at least one halogen, an aryl group having 6–20 carbon atoms optionally substituted with at least one halogen atom, a substituted silyl goup having 1–20 carbon atoms optionally substituted with at least one halogen atom, an alkoxy group having 1–20 carbon atoms optionally substituted with at least one halogen atom, an aralkyloxy group having 7–20 carbon atoms optionally substituted with at least one halogen atom, an aryloxy group having 6–20 carbon atoms optionally substituted with at least one halogen atom, or a di-substituted amino group having 2–20 carbon atoms, provided that $R^1$, $R^2$, $R^3$, $R^4$, $R^5$, and $R^6$ may optionally combine with each other to form a ring, A represents an atom from goup 16 of the periodic table of elements, B' represents an element from group 14 of the periodic table of elements other than carbon atom, $R^7$ represents a hydrocarbon group optionally substituted with at least one halogen atom or a tri-substituted silyl group and $Cp^2$ represents a cyclopentadiene skeleton which comprises reacting a halogenated aryl compound represented by the formula (9)

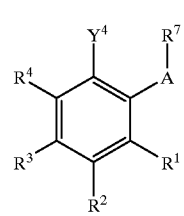
(9)

wherein $Y^4$ represents a halogen atom and A, $R^1$, $R^2$, $R^3$, $R^4$, and $R^7$ are respectively the same as defined above with a halide compound represented by the formula (8)

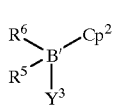
(8)

wherein $Y^3$ represents a halogen atom, and B', $Cp^2$, $R^5$ and $R^6$ are respectively the same as defined above in the presence of an organoalkali metal compound or metallic magnesium.

15. The process for producing a substituted cyclopentadienyl compound according to claim 14 wherein the halogenated arl compound represented said formula (9) wherein $Y^4$ is a halogen atom, and A, $R^1$, $R^2$, $R^3$, $R^4$, and $R^7$ are respectively the same as defined above is produced by reacting a halogenated aryl compound represented by the formula (10)

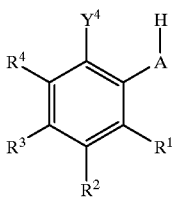

(10)

wherein A, $R^1$, $R^2$, $R^3$, $R^4$, and $Y^4$ are respectively the same as defined above with a halide represented by the formula (11)

$$R^7Y^5 \qquad (11)$$

wherein $Y^5$ represents a halogen atom and $R^7$ is as defined above in the presence of a base.

16. A halide compound represented by the formula (5)

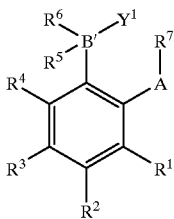

(5)

wherein $R^1$, $R^2$, $R^3$, $R^4$, $R^5$, and $R^6$ are each independently a hydrogen atom, a halogen atom, an alkyl group having 1–20 carbon atoms optionally substituted with at least one halogen atom, an aralkyl group having 7–20 carbon atoms optionally substituted with at least one halogen atom, an aryl group having 6–20 carbon atoms optionally substituted with at least one halogen atom, a substituted silyl group having 1–20 carbon atoms optionally substituted with at least one halogen atom, an alkoxy group having 1–20 carbon atoms optionally substituted with at least one halogen atom, an aralkyloxy group having 7–20 carbon atoms optionally substituted with at least one halogen atom, an aryloxy group having 6–20 carbon atoms optionally substituted with at least one halogen atom, or a di-substituted amino group having 2–20 carbon atoms, provided that $R^1$, $R^2$, $R^3$, $R^4$, $R^5$, and $R^6$ may optionally combine with each other to form a ring A represents an atom from group 16 of the periodic table of elements, $R^7$ represents a hydrocarbon group optionally substituted with at least one halogen atom or a tri-substituted silyl group and B' represents an element from group 14 of the periodic table of elements other than a carbon atom.

17. A process for producing the halide compound according to claim 16, which comprises reacting a halogenated aryl compound represented by the formula (9)

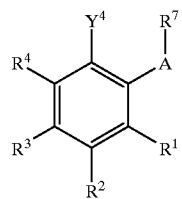

(9)

wherein $Y^4$ is a halogen atom, and A, $R^1$, $R^2$, $R^3$, $R^4$, and $R^7$ are respectively the same as defined above with a dihalide compound represented by the formula (7)

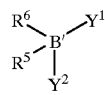

(7)

wherein $Y^1$ is as defined above, $Y^2$ represents a halogen atom, B' is as defined above, and $R^5$ and $R^6$ are respectively the same as defined above in the presence of an organoalkali metal compound or metallic magnesium.

18. The process according to claim 17, wherein the halogenated aryl compound represented said formula (9) wherein $Y^4$ is a haloen atom, and A, $R^1$, $R^2$, $R^3$, $R^4$, and $R^7$ are respectively the same as defined above is produced by reacting a halogenated aryl compound represented by the formula (10)

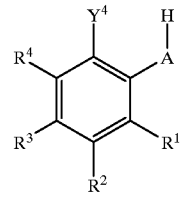

(10)

wherein A, $R^1$, $R^2$, $R^3$, $R^4$, and $Y^4$ are respectively the same as defined above with a halide represented by the formula (11)

$$R^7Y^5 \qquad (11)$$

wherein $Y^5$ represents a halogen atom and $R^7$ is as defined above in the presence of a base.

19. An olefin polymerization catalyst which comprises the transition metal complex according to any of claims 1–4 and a compound (A) described below:

(A) any one of the following compounds (A1)–(A3) or the mixture of two or three thereof, (A1) an organoaluminum compound represented by the formula $E^1{}_aAlZ_{3-a}$ (A2) a cyclic aluminoxane having the structure represented by the formula $\{Al(E^2)\text{—}O\text{—}\}_b$ (A3) a linear aluminoxane having the structure represented by the formula $E^3\{Al(E^3)\text{—}O\text{—}\}_cAlE^3{}_2$ wherein $E^1$–$E^3$ are each a hydrocarbon group with the number of carbon atoms of 1–8, and all $E^1$, all $E^2$ and all $E^3$ may be the same with or different from each other; Z is a hydrogen atom or halogen atom, and all Z may be the same with or different from each other; a is the number specified by $0<a\leq 3$, b is an integer of 2 or more, and c is an integer of 1 or more.

20. An olefin polymerization catalyst which comprises the transition metal complex according to any of claims 1–4 and the following compounds (A) and (B):

(A) any one of the following compounds (A1)–(A3) or the mixture of two or three thereof:
  (A1) an organoaluminum compound represented by the formula $E^1_aAlZ_{3-a}$
  (A2) a cyclic aluminoxane having the structure represented by the formula $\{Al(E^2)\text{—}O\text{—}\}_b$
  (A3) a linear aluminoxane having the structure represented by the formula $E^3\{Al(E^3)\text{—}O\text{—}\}_cAlE^3_2$ wherein $E^1$–$E^3$ are each a hydrocarbon group with the number of carbon atoms of 1–8, and all $E^1$, all $E^2$ and all $E^3$ may be the same with or different from each other; Z is a hydrogen atom or halogen atom and all Z may be the same with or different from each other; a is the number specified by $0<a\leq 3$, b is an integer of 2 or more and c is an integer of 1 or more, (B) any of the following compounds (B1)–(B3):
  (B1) a boron compound represented by the formula $BQ^1Q^2Q^3$,
  (B2) a boron compound represented by the formula $Z^+(BQ^1Q^2Q^3Q^4)^-$,
  (B3) a boron compound represented by the formula $(L\text{-}H)^+(BQ^1Q^2Q^3Q^4)^-$,
wherein B is a boron atom of a tri-valent valence state; $Q^1$–$Q^4$ are each a halogen atom, hydrocarbon group with the number of carbon atoms of 1–20, halogenated hydrocarbon group with the number of carbon atoms of 1–20, substituted silyl group with the number of carbon atoms of 1–20, alkoxy group with the number of carbon atoms of 1–20 or di-substituted amino group with the number of carbon atoms of 2–20, and they may be the same with or different from each other.

21. The olefin polymerization catalyst according to 19 wherein the compound (A) is triethylaluminum, triisobutylaluminum, or methylaluminoxane.

22. A process for producing olefin polymers which comprises using the olefin polymerization catalyst according to any of the claims 19–21.

23. The process for producing olefin polymers according to claim 22 wherein the olefin polymer is ethylene-α-olefin copolymer.

24. The process for producing olefin polymer according to claim 22 wherein the olefin polymer is ethylene-α-olefin copolymer rubber.

25. The process for producing olefin polymers according to claim 22 wherein the olefin polymer is ethylene-α-olefin-nonconjugated diene copolymer rubber.

26. The olefin polymerization catalyst according to claim 20, wherein the compound (A) is triethylaluminum, triisobutylaluminum, or methylaluminoxane.

27. A process for producing olefin polymers which comprises using the olefin polymerization catalyst according to claim 20.

28. A process for producing olefin polymers which comprises using the olefin polymerization catalyst according to claim 21.

29. The process for producing olefin polymers according to claim 27, wherein the olefin polymer is an etbylene-α-olefin copolymer.

30. The process for producing olefin polymers according to claim 28, wherein the olefm polymer is an ethylene-α-olefin copolymer.

31. The process for producing olefin polymers according to claim 21, wherein the olefin polymer is an ethylene-α-olefin copolymer rubber.

32. The process for producing olefin polymers according to claim 27, wherein the olefin polymer is an ethylene-α-olefin copolymer.

33. The process for producing olefin polymers according to claim 25, wherein the olefin polymer is an ethylene-α-olefin copolymer.

34. The process for producing olefin polymers according to claim 22, wherein the olefin polymer is an ethylene-α-olefin-nonconjugated diene copolymer rubber.

35. The process for producing olefin polymers according to claim 27, wherein the olefin polymer is an ethylene-α-olefin-nonconjugated diene copolymer rubber.

36. The process for producing olefin polymers according to claim 28, wherein the olefm polymer is an ethylene-α-olefin-nonconjugated diene copolymer rubber.

37. A halogenated aryl compound represented by the general formula (9):

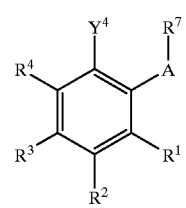

(9)

wherein A is an oxygen atom, $Y^4$ is a bromine atom, $R^1$ represents an alkyl group having 1 to 20 carbon atoms, $R^3$ represents an alkyl or alkoxy group having 1 to 20 carbon atoms, $R^2$ and $R^4$ represent a hydrogen atom and $R^7$ represents an allyl group.

38. The halogenated aryl compound according to claim 37, wherein $R^1$ represents a t-butyl group and $R^3$ represents a methyl group.

39. The halogenated aryl compound according to claim 37, wherein $R^1$ and $R^3$ represent a methyl group.

40. The halogenated aryl compound according to claim 37, wherein $R^1$ represents a t-butyl group and $R^3$ represents a methoxy group.

* * * * *